(12) United States Patent
Makrigiorgos et al.

(10) Patent No.: US 11,884,970 B2
(45) Date of Patent: Jan. 30, 2024

(54) DENATURATION-ENHANCED DNA MUTATION TESTING FOR LIMITED BIOLOGICAL SPECIMENS

(71) Applicant: Dana-Farber Cancer Institute, Inc., Boston, MA (US)

(72) Inventors: Gerassimos Makrigiorgos, Chestnut Hill, MA (US); Cloud P. Paweletz, Boston, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 94 days.

(21) Appl. No.: 17/057,936

(22) PCT Filed: May 24, 2019

(86) PCT No.: PCT/US2019/033876
§ 371 (c)(1),
(2) Date: Nov. 23, 2020

(87) PCT Pub. No.: WO2019/226970
PCT Pub. Date: Nov. 28, 2019

(65) Prior Publication Data
US 2021/0214778 A1 Jul. 15, 2021

Related U.S. Application Data

(60) Provisional application No. 62/737,033, filed on Sep. 26, 2018, provisional application No. 62/676,082, filed on May 24, 2018.

(51) Int. Cl.
*C12Q 1/68* (2018.01)
*C12Q 1/6848* (2018.01)
*C12Q 1/6806* (2018.01)

(52) U.S. Cl.
CPC ......... *C12Q 1/6848* (2013.01); *C12Q 1/6806* (2013.01); *C12Q 2600/156* (2013.01)

(58) Field of Classification Search
CPC .............. C12Q 1/6848; C12Q 1/6806; C12Q 2600/156; C12Q 1/6844
See application file for complete search history.

(56) References Cited

U.S. PATENT DOCUMENTS 9,896,717 B2  2/2018  Hodges et al.
2009/0239308 A1  9/2009  Dube et al.
(Continued)

FOREIGN PATENT DOCUMENTS

WO  WO 2010/018465 A2  2/2010
WO  WO 2014/186147 A2  11/2014
(Continued)

OTHER PUBLICATIONS

Racki et al. (Anal Bioanal Chem, 2014, 406:661-667) (Year: 2014).*
(Continued)

*Primary Examiner* — Stephanie K Mummert
(74) *Attorney, Agent, or Firm* — Mueting Raasch Group

(57) ABSTRACT

Disclosed herein are methods to improve the efficiency of absolute quantification of nucleic acid targets such as digital PCR and digital isothermal amplification, and/or reduce the amount of nucleic acid sample required to determine the absolute quantity of target sequences in the sample.

21 Claims, 29 Drawing Sheets

(56) References Cited

U.S. PATENT DOCUMENTS

2011/0183330 A1 7/2011 Lo et al.
2016/0275240 A1* 9/2016 Huelga ............... C12Q 1/6806

FOREIGN PATENT DOCUMENTS

WO WO 2016/170109 A1 10/2016
WO WO 2017/079696 A1 5/2017

OTHER PUBLICATIONS

Mazutis et al. (Anal Chem, 2009, vol. 81, p. 4813-4821) (Year: 2009).*
Duewer et al. (Anal Bioanal Chem, 2015, 407:9061-9069) (Year: 2015).*
Bhat et al. (Analyst 2011, 136(4):724-32, IDS reference) (Year: 2011).*
Bhat et al. (Anal Chem, 2010, 82, 7185-7192) (Year: 2010).*
Gregory et al. (Nucleic Acids Research, 2016, 44(3):e22 p. 1-11) (Year: 2016).*
Castellanos-Rizaldos et al., Enhanced ratio of signals enables digital mutation scanning for rare allele detection. J Mol Diagn. May 2015;17(3):284-92. doi: 10.1016/j.jmoldx.2014.12.003. Epub Mar. 13, 2015.
Guha et al., Differential strand separation at critical temperature: a minimally disruptive enrichment method for low-abundance unknown DNA mutations. Nucleic Acids Res. Feb. 1, 2013;41(3):e50. doi: 10.1093/nar/gks1250. Epub Dec. 20, 2012.
Herrmann et al., Amplicon DNA melting analysis for mutation scanning and genotyping: cross-platform comparison of instruments and dyes. Clin Chem. Mar. 2006;52(3):494-503. doi: 10.1373/clinchem.2005.063438. Epub Jan. 19, 2006.
Hindson et al., Absolute quantification by droplet digital PCR versus analog real-time PCR. Nat Methods. Oct. 2013;10(10):1003-5. doi: 10.1038/nmeth.2633. Epub Sep. 1, 2013.
Hindson et al., High-throughput droplet digital PCR system for absolute quantitation of DNA copy number. Anal Chem. Nov. 15, 2011;83(22):8604-10. doi: 10.1021/ac202028g. Epub Oct. 28, 2011.
Huggett et al., Considerations for digital PCR as an accurate molecular diagnostic tool. Clin Chem. Jan. 2015;61(1):79-88. doi: 10.1373/clinchem.2014.221366. Epub Oct. 22, 2014.
Huggett et al., The digital MIQE guidelines: Minimum Information for Publication of Quantitative Digital PCR Experiments. Clin Chem. Jun. 2013;59(6):892-902. doi: 10.1373/clinchem.2013.206375. Epub Apr. 9, 2013.
Laurent-Puig et al., Clinical relevance of KRAS-mutated subclones detected with picodroplet digital PCR in advanced colorectal cancer treated with anti-EGFR therapy. Clin Cancer Res. Mar. 1, 2015;21(5):1087-97. doi: 10.1158/1078-0432.CCR-14-0983. Epub Sep. 23, 2014.
Li et al., s-RT-MELT for rapid mutation scanning using enzymatic selection and real time DNA-melting: new potential for multiplex genetic analysis. Nucleic acids res. 2007;35(12):e84.
Schuler et al., Digital droplet LAMP as a microfluidic app on standard laboratory devices. Anal. Methods, 2016,8:2750-2755.
Taly et al., Multiplex picodroplet digital PCR to detect KRAS mutations in circulating DNA from the plasma of colorectal cancer patients. Clin Chem. Dec. 2013;59(12):1722-31. doi: 10.1373/clinchem.2013.206359. Epub Aug. 12, 2013.
Vogelstein et al., Digital PCR. Proc Natl Acad Sci U S A. Aug. 3, 1999;96(16):9236-41. doi: 10.1073/pnas.96.16.9236.
Whale et al., Methods for applying accurate digital PCR analysis on low copy DNA samples. PLoS One. 2013;8(3):e58177. doi: 10.1371/journal.pone.0058177. Epub Mar. 5, 2013.
Bhat et al., Effect of sustained elevated temperature prior to amplification on template copy number estimation using digital polymerase chain reaction. Analyst. Feb. 21, 2011;136(4):724-32. doi: 10.1039/c0an00484g. Epub Nov. 25, 2010.
Day et al., Digital PCR strategies in the development and analysis of molecular biomarkers for personalized medicine. Methods. Jan. 2013;59(1):101-7. doi: 10.1016/j.ymeth.2012.08.001. Epub Aug. 19, 2012.
Postel et al., Droplet-based digital PCR and next generation sequencing for monitoring circulating tumor DNA: a cancer diagnostic perspective. Expert Rev Mol Diagn. Jan. 2018;18(1):7-17. doi: 10.1080/14737159.2018.1400384. Epub Nov. 13, 2017.
International Search Report and Written Opinion dated Oct. 10, 2019 for International Application No. PCT/US2019/33876.
International Preliminary Report on Patentability dated Dec. 3, 2020 for International Application No. PCT/US2019/33876.
[No Author Listed], Tm Calculator, version 1.15.0. New England Biolabs [online]. Retrieved on Mar. 7, 2023. http://tmcalculator.neb.com/#!/main. Published Mar. 18, 2019. 1 Page.
Adalsteinsson et al., Scalable whole-exome sequencing of cell-free DNA reveals high concordance with metastatic tumors. Nat Commun. Nov. 6, 2017;8(1):1324. doi: 10.1038/s41467-017-00965-y.
Amicarelli et al., FLAG assay as a novel method for real-time signal generation during PCR: application to detection and genotyping of KRAS codon 12 mutations. Nucleic Acids Res. 2007;35(19):e131. doi: 10.1093/nar/gkm809. Epub Oct. 11, 2007.
Bernard et al., Real-time PCR technology for cancer diagnostics. Clin Chem. Aug. 2002;48(8):1178-85.
Bettegowda et al., Detection of circulating tumor DNA in early- and late-stage human malignancies. Sci Transl Med. Feb. 19, 2014;6(224):224ra24. doi: 10.1126/scitranslmed.3007094.
Castellanos-Rizaldos et al., Single-tube, highly parallel mutation enrichment in cancer gene panels by use of temperature-tolerant COLD-PCR. Clin Chem. Jan. 2015;61(1):267-77. doi: 10.1373/clinchem.2014.228361. Epub Oct. 8, 2014.
Chen et al., Personal omics profiling reveals dynamic molecular and medical phenotypes. Cell. Mar. 16, 2012;148(6):1293-307. doi: 10.1016/j.cell.2012.02.009.
Diehl et al., Circulating mutant DNA to assess tumor dynamics. Nat Med. Sep. 2008;14(9):985-90. doi: 10.1038/nm.1789. Epub Jul. 31, 2007.
Diehl et al., Detection and quantification of mutations in the plasma of patients with colorectal tumors. Proc Natl Acad Sci U S A. Nov. 8, 2005;102(45):16368-73. doi: 10.1073/pnas.0507904102. Epub Oct. 28, 2005.
Galbiati et al., Full COLD-PCR protocol for noninvasive prenatal diagnosis of genetic diseases. Clin Chem. Jan. 2011;57(1):136-8. doi: 10.1373/clinchem.2010.155671. Epub Oct. 25, 2010.
Gevensleben et al., Noninvasive detection of HER2 amplification with plasma DNA digital PCR. Clin Cancer Res. Jun. 15, 2013;19(12):3276-84. doi: 10.1158/1078-0432.CCR-12-3768. Epub May 1, 2013.
Gill et al., Nucleic acid isothermal amplification technologies: a review. Nucleosides Nucleotides Nucleic Acids. Mar. 2008;27(3):224-43. doi: 10.1080/15257770701845204.
How et al., Sensitive detection of KRAS mutations using enhanced-ice-COLD-PCR mutation enrichment and direct sequence identification. Hum Mutat. Nov. 2013;34(11):1568-80. doi: 10.1002/humu.22427. Epub Sep. 17, 2013.
Ladas et al., Enhanced detection of microsatellite instability using pre-PCR elimination of wild-type DNA homo-polymers in tissue and liquid biopsies. Nucleic Acids Res. Jul. 6, 2018;46(12):e74. doi: 10.1093/nar/gky251.
Li et al., Antiprimer quenching-based real-time PCR and its application to the analysis of clinical cancer samples. Clin Chem. Apr. 2006;52(4):624-33. doi: 10.1373/clinchem.2005.063321. Epub Feb. 9, 2006.
Li et al., Coamplification at lower denaturation temperature-PCR increases mutation-detection selectivity of TaqMan-based real-time PCR. Clin Chem. Apr. 2009;55(4):748-56. doi: 10.1373/clinchem.2008.113381. Epub Feb. 20, 2009.
Li et al., Replacing PCR with COLD-PCR enriches variant DNA sequences and redefines the sensitivity of genetic testing. Nat Med. May 2008;14(5):579-84. doi: 10.1038/nm1708. Epub Apr. 13, 2008.
Li et al., Two-round coamplification at lower denaturation temperature-PCR (COLD-PCR)-based sanger sequencing identifies a novel

(56) References Cited

OTHER PUBLICATIONS spectrum of low-level mutations in lung adenocarcinoma. Hum Mutat. Nov. 2009;30(11):1583-90. doi: 10.1002/humu.21112.
Liu et al., Methylation-sensitive enrichment of minor DNA alleles using a double-strand DNA-specific nuclease. Nucleic Acids Res. Apr. 7, 2017;45(6):e39. doi: 10.1093/nar/gkw1166.
Lo et al., Digital PCR for the molecular detection of fetal chromosomal aneuploidy. Proc Natl Acad Sci U S A. Aug. 7, 2007;104(32):13116-21. doi: 10.1073/pnas.0705765104. Epub Jul. 30, 2007.
Mauger et al., Multiplexing of E-ice-COLD-PCR Assays for Mutation Detection and Identification. Clin Chem. Aug. 2016;62(8):1155-8. doi: 10.1373/clinchem.2016.258830. Epub Jun. 22, 2016.
Milbury et al., Ice-COLD-PCR enables rapid amplification and robust enrichment for low-abundance unknown DNA mutations. Nucleic Acids Res. Jan. 2011;39(1):e2. doi: 10.1093/nar/gkq899. Epub Oct. 11, 2010.
Milbury et al., PCR-based methods for the enrichment of minority alleles and mutations. Clin Chem. Apr. 2009;55(4):632-40. doi: 10.1373/clinchem.2008.113035. Epub Feb. 6, 2009.
MILBURY et al., COLD-PCR enrichment of rare cancer mutations prior to targeted amplicon resequencing. Clin Chem. Mar. 2012;58(3):580-9. doi: 10.1373/clinchem.2011.176198. Epub Dec. 21, 2011.
Murphy et al., NRAS mutations with low allele burden have independent prognostic significance for patients with lower risk myelodysplastic syndromes. Leukemia. Oct. 2013;27(10):2077-81. doi: 10.1038/leu.2013.160. Epub May 27, 2013.
Narayan et al., Ultrasensitive measurement of hotspot mutations in tumor DNA in blood using error-suppressed multiplexed deep sequencing. Cancer Res. Jul. 15, 2012;72(14):3492-8. doi: 10.1158/0008-5472.CAN-11-4037. Epub May 10, 2012.
Newman et al., An ultrasensitive method for quantitating circulating tumor DNA with broad patient coverage. Nat Med. May 2014;20(5):548-54. doi: 10.1038/nm.3519. Epub Apr. 6, 2014.
Newton et al., Analysis of any point mutation in DNA. The amplification refractory mutation system (ARMS). Nucleic Acids Res. Apr. 11, 1989;17(7):2503-16. doi: 10.1093/nar/17.7.2503.
Oxnard et al., Noninvasive detection of response and resistance in EGFR-mutant lung cancer using quantitative next-generation genotyping of cell-free plasma DNA. Clin Cancer Res. Mar. 15, 2014;20(6):1698-1705. doi: 10.1158/1078-0432.CCR-13-2482. Epub Jan. 15, 2014.
Pekin et al., Quantitative and sensitive detection of rare mutations using droplet-based microfluidics. Lab Chip. Jul. 7, 2011;11(13):2156-66. doi: 10.1039/c1lc20128j. Epub May 19, 2011.
Quan et al., dPCR: A Technology Review. Sensors (Basel). Apr. 20, 2018;18(4):1271. doi: 10.3390/s18041271.
Roschewski et al., Circulating tumour DNA and CT monitoring in patients with untreated diffuse large B-cell lymphoma: a correlative biomarker study. Lancet Oncol. May 2015;16(5):541-9. doi: 10.1016/S1470-2045(15)70106-3. Epub Apr. 1, 2015.
Sanchez et al., Linear-after-the-exponential (LATE)-PCR: an advanced method of asymmetric PCR and its uses in quantitative real-time analysis. Proc Natl Acad Sci U S A. Feb. 17, 2004;101(7):1933-8. doi: 10.1073/pnas.0305476101. Epub Feb. 9, 2004. Erratum.
Schwaederle et al., Use of Liquid Biopsies in Clinical Oncology: Pilot Experience in 168 Patients. Clin Cancer Res. Nov. 15, 2016;22(22):5497-5505. doi: 10.1158/1078-0432.CCR-16-0318. Epub May 16, 2016.
Song et al., Elimination of unaltered DNA in mixed clinical samples via nuclease-assisted minor-allele enrichment. Nucleic Acids Res. Nov. 2, 2016;44(19):e146. doi: 10.1093/nar/gkw650. Epub Jul. 18, 2016.
Sun et al., Detection of tumor mutations in the presence of excess amounts of normal DNA. Nat Biotechnol. Feb. 2002;20(2):186-9. doi: 10.1038/nbt0202-186.
Sykes et al., Quantitation of targets for PCR by use of limiting dilution. Biotechniques. Sep. 1992;13(3):444-9.
Tadmor et al., Probing individual environmental bacteria for viruses by using microfluidic digital PCR. Science. Jul. 1, 2011;333(6038):58-62. doi: 10.1126/science.1200758.
Thierry et al., Clinical validation of the detection of KRAS and BRAF mutations from circulating tumor DNA. Nat Med. Apr. 2014;20(4):430-5. doi: 10.1038/nm.3511. Epub Mar. 23, 2014.
Thomas et al., Sensitive mutation detection in heterogeneous cancer specimens by massively parallel picoliter reactor sequencing. Nat Med. Jul. 2006; 12(7):852-5. doi: 10.1038/nm1437. Epub Jun. 25, 2006. Erratum.
Tyagi et al., Molecular beacons: probes that fluoresce upon hybridization. Nat Biotechnol. Mar. 1996;14(3):303-8. doi: 10.1038/nbt0396-303.
Wang et al., Quantifying EGFR alterations in the lung cancer genome with nanofluidic digital PCR arrays. Clin Chem. Apr. 2010;56(4):623-32. doi: 10.1373/clinchem.2009.134973. Epub Mar. 5, 2010.
Whale et al., Comparison of microfluidic digital PCR and conventional quantitative PCR for measuring copy number variation. Nucleic Acids Res. Jun. 2012;40(11):e82. doi: 10.1093/nar/gks203. Epub Feb. 28, 2012.
Wu et al., Continuously tunable nucleic acid hybridization probes. Nat Methods. Dec. 2015;12(12):1191-6. doi: 10.1038/nmeth.3626. Epub Oct. 19, 2015.
Wu et al., Multiplexed enrichment of rare DNA variants via sequence-selective and temperature-robust amplification. Nat Biomed Eng. 2017;1:714-723. doi: 10.1038/s41551-017-0126-5. Epub Sep. 4, 2017. Erratum.
Zhang et al., Copy number variation in human health, disease, and evolution. Annu Rev Genomics Hum Genet. 2009;10:451-81. doi: 10.1146/annurev.genom.9.081307.164217.

\* cited by examiner anchor-tail1 and anchor-tail 2: low conc (eg 0.001-0.010 uM)

tail1 and tail 2 – high conc (eg 0.1-1uM)

Reverse primer OR blocker reverse primer – high conc 0.1uM-1uM

| Sample | Copy genotype | Concentration fold-change |
|---|---|---|
| 10 ng | WT | 1.84 |
| 5 ng | WT | 1.89 |
| 2.5 ng | WT | 1.85 |
| 1.25 ng | WT | 1.99 |
| 10 ng | MT | 2.02 |
| 5 ng | MT | 2.29 |
| 2.5 ng | MT | 1.72 |
| 1.25 ng | MT | 2.07 |

| Assay | Sample | Concentration fold-change |
|---|---|---|
| BRAF V600E | gDNA | 1.91 |
| | cfDNA | 1.74 |
| | End repaired cfDNA | 1.94 |
| EGFR L858R | gDNA | 1.95 |
| | cfDNA | 1.67 |
| | End repaired cfDNA | 1.96 |

Figure 19C

DENATURATION-ENHANCED DNA MUTATION TESTING FOR LIMITED BIOLOGICAL SPECIMENS

RELATED APPLICATIONS

This application is a national stage filing under 35 U.S.C. § 371 of International PCT Application PCT/US2019/033876, filed May 24, 2019, which claims the benefit under 35 U.S.C. § 119(e) from U.S. provisional application No. 62/676,082, filed May 24, 2018, and U.S. provisional application No. 62/737,033, filed Sep. 26, 2018, each of which is incorporated by reference herein in its entirety.

GOVERNMENT INTEREST

This invention was made with government support under R33 CA217652 and R01 CA221874 awarded by the National Institutes of Health. The government has certain rights in the invention.

BACKGROUND OF THE INVENTION

Digital polymerase chain reaction (dPCR) is an example of a method of absolute quantification (i.e. without the need of a standard) of a target sequence in a sample of nucleic acid (e.g., DNA or RNA). In dPCR, the initial sample mix is partitioned into a large number of individual partitions (e.g., droplets or wells) prior to the amplification step, resulting in either 1 or 0 target sequences being present in each well. Following PCR amplification, the number of positive versus negative reactions or reaction compartments (i.e., the number of partitions having versus not having the target sequence, respectively) is determined and the absolute quantification of target in the original unpartitioned sample is calculated using mathematical models (e.g., Poisson statistics). Any other amplification methods (e.g., isothermal amplification) applied on each compartment can provide similar absolute quantification.

Digital methods of absolute quantification (e.g., dPCR) are powerful methods having advantages of both sensitivity and reproducibility, thus making an attractive method for various applications including, but not limited to, mutation detection in clinical samples, gene copy-number analysis in cancer, and prenatal-screening.

SUMMARY OF THE INVENTION

While interest in absolute nucleic acid target quantification methodologies such as dPCR technology (e.g., digital-droplet PCR (ddPCR)) are burgeoning, the technologies are compromised by sub-sampling errors, and quantitative limitation of input nucleic acid (e.g., DNA from clinical samples). The paucity of starting material acts as a 'glass ceiling' since, irrespective of how sensitive dPCR techniques are, detection limits cannot be improved past DNA input limitations.

Provided herein is a method of improving the sensitivity of absolute nucleic acid quantification methods (e.g., dPCR), which is based, at least in part, on the recognition that although absolute nucleic acid quantification methods (e.g., dPCR) amplify individual double-stranded nucleic acid (e.g., double-stranded DNA) in distinct reaction compartments and obtain signal readout from each compartment to reveal and quantify particular target nucleic acid sequences (e.g., mutant target nucleic acid sequences), the information contained in the double-stranded nucleic acid is redundant, as each nucleotide of the nucleic acid target appears in both the sense and antisense strands of the original nucleic acid molecule. The approach disclosed herein for enhancing the information obtained from absolute nucleic acid quantification methods (e.g., dPCR, or digital isothermal amplification) involves denaturing input double-stranded nucleic acid into single strands, and performing digital amplification methods (e.g., dPCR, or digital isothermal amplification) on the single strands, effectually doubling the amount of input nucleic acid from which information can be extracted. The denaturing of double-stranded nucleic acid to single-stranded nucleic acid thus effectually increases the sensitivity of a detection assay, while providing essentially the same result of detection.

Accordingly, provided herein is a method comprising
  (a) denaturing a double-stranded nucleic acid in a sample to form single-stranded nucleic acid, wherein the double-stranded nucleic acid comprises a target sequence;
  (b) partitioning the sample of formed single-stranded nucleic acid into a multitude of compartments, wherein a vast majority of the compartments contain either one or none single-stranded nucleic acid comprising the target sequence; and
  (c) assaying for the target in each of the compartments (e.g., by performing amplification reactions in each of the compartments to amplify nucleic acids comprising the target when present in a compartment).

In some embodiments, a "majority of the compartments" is the fraction of total number of compartments that may not contain more than one single-stranded nucleic acids comprising the target sequence so that Poisson's distribution can be assumed to be applicable to the distribution of targets in the compartments. In some embodiments, a "majority of the compartments" means at least 95% of the compartments (e.g., at least 95%, at least 98%, at least 99%, at least 99.9%, at least 99.99%, or at least 99.999% of the compartments). In some embodiments, a minority (e.g., 5%, 4%, 3%, 2%, 1%, 0.5%, 0.1%, 0.01%, or 0.001% or less) of the compartments contain more than one single-stranded nucleic acids comprising the target sequence (e.g., 2, 3, 4, 5, or 6). Stated differently, in step (b) above, the sample is partitioned such that the partitions containing a target strand will contain only a single target strand. This permits digital PCR quantitative calculations.

In some embodiments, assaying for the target in each of the compartments comprises subjecting each of the compartments to amplification conditions, in some embodiments including primers for the target, thereby amplifying target nucleic acid in compartments in which a target is present. In some embodiments, assaying for the target in each of the compartments comprises subjecting the compartments to an isothermal amplification reaction to amplify target nucleic acid in compartments in which they are present. In some embodiments, a method further comprising adding one or more of the following isothermal amplification regents to the sample: a nicking nuclease (e.g., a DNA-nicking nuclease), a strand-displacing polymerase, deoxynucleotide triphosphates (dNTPs). In some embodiments of any one of the methods disclosed herein which utilizes isothermal amplification as a method of detection of target in compartments containing a target, the introduction of amplification reagents is under inactive state conditions (e.g., by introducing and maintaining amplification reagents at 0-4° C.), which are then activated once the sample is partitioned. Amplification enzymes may also be maintained to be inactive by addition of thermolabile-reagents (e.g., antibodies, aptamers or other chemical reagents) that keep the enzymes inactive until the temperature is increased to a certain level.

In some embodiments, assaying for the target in each of the compartments comprises subjecting the compartments to polymerase chain reaction (PCR), thereby amplifying target nucleic acid in those compartments containing a target. In some embodiments, a method further comprising adding one or more of the following PCR reagents to the sample: forward and reverse primers, a polymerase, hydrolysis probes, and deoxynucleotide triphosphates (dNTP). In some embodiments, one or more amplification reagents (e.g., PCR or isothermal amplification reagents) are added to the sample prior to denaturing the double-stranded nucleic acid.

In some embodiments, denaturing of the double-stranded nucleic acid is performed by exposing the sample to a temperature of at least 95° C.

In some embodiments, compartments are micro well plates, capillaries, oil-in-water emulsion droplets, nanofluidic devices, or arrays of miniaturized chambers. In some embodiments, the compartments are oil-in-water emulsion droplets.

In some embodiments, single stranded nucleic acid is converted to double-stranded nucleic acid before performing PCR. In some embodiments, PCR that is performed on each compartment comprises:
 (a) activating a polymerase;
 (b) denaturing the nucleic acid present in a compartment;
 (c) annealing of target primers to single-stranded nucleic acid target if present in a compartment;
 (d) extending the primers to form double-strand nucleic acid; and
 (e) repeating steps (b)-(d) at least once, and preferably through many cycles.

In some embodiments, a polymerase is activated by exposing the compartment to a temperature of 90-97° C. for 0.1-10 minutes. In some embodiments, denaturing the nucleic acid comprises exposing the compartment to a temperature of 90-98° C. for 2-120 seconds. In some embodiments, annealing or primers to single-stranded nucleic acid extending the primers to form double-strand nucleic acid comprises exposing the compartment to a temperature of 50-70° C. for 5 seconds to 2 minutes.

In some embodiments, any one of the methods disclosed herein further comprises reducing the damage of single-stranded nucleic acid prior to performing amplification of the target nucleic acid. In some embodiments, reducing damage of formed single-stranded nucleic acid comprises: partially activating a polymerase by exposing each compartment to a temperature of 90-97° C. for 0.1-2 minutes; and generating double-stranded nucleic acid by performing 2-8 cycles of PCR also involving temperature 90-97° C. for 0.1-2 minutes.

Amplification initially using just a sense or antisense nucleic acid strand in a reaction compartment (also referred to herein as a "partition") is expected to double the number of positive compartments (i.e. compartments showing the presence of a target nucleic acid) as when the compartments initially include double-stranded molecules, provided the sense and antisense strands of the double-stranded molecule are of equal size (e.g., blunt-ended DNA). However, sometimes, the input nucleic acid to be analyzed by digital PCR is randomly fragmented with largely complementary strands of unequal length (e.g., as that found typically in cell-free circulating DNA), such that there is substantial non-overlap of sequence between the sense and antisense strands. This can result in primers not being able to prime equally on both strands, and the result may be less than a doubling of the dPCR signal. End-repair of double-stranded nucleic acid ensures that the double-stranded nucleic acid has blunt ends, and therefore, a sense and antisense strand of equal length. Accordingly, provided herein is a method that combines end-repair of double-stranded nucleic acid fragments with denaturing double-stranded (dsDNA) to single-stranded (ssDNA) prior to implementing a method of absolute quantification of one or more target nucleic acids (e.g., dPCR, or digital isothermal amplification). Accordingly, in some embodiments, any one of the methods disclosed herein further comprises producing blunt ends on double-stranded nucleic acid. In some embodiments, producing the blunt ends comprises treatment with end-repair enzyme. In some embodiments, an end-repair enzyme is a T7 DNA polymerase, a T4 DNA polymerase, or a Klenow fragment. Other such enzymes are known to those skilled in the art. In some embodiments, an end-repaired double-stranded nucleic acid is separated or purified from the repair enzyme after it has been end-repaired. In some embodiments, an end-repaired double-stranded nucleic acid is separated or purified from the repair enzyme after it has been end-repaired and prior to denaturing it to form single-stranded nucleic acid. In some embodiments, producing the blunt ends on a double-stranded nucleic acid and denaturing the double-stranded nucleic acid are carried out in the same reaction vessel. In some embodiments, any one of the methods disclosed herein comprise end-repair of double-stranded nucleic acid and inactivating the end-repair enzyme once end-repair has been performed. In some embodiments, end-repair enzyme inactivation comprises exposing the sample to a temperature of at least 65° C. for a period of time that reduces the activity of the enzyme by at least 90%. In some embodiments, end-repair enzyme inactivation comprises exposing the sample to a temperature of at least 65° C. for 2-60 minutes.

In some embodiments, a sample of double-stranded nucleic acid is genomic DNA or cDNA. In some embodiments, genomic DNA is cell-free circulating DNA. In some embodiments, genomic DNA is obtained from a biological sample. In some embodiments, a biological sample is serum, plasma, blood, urine, solid tissue, feces, skin, hair, a buccal swab, or a pulmonary brushing.

In some embodiments, the size of amplicons formed during PCR in compartments containing a target 50-120 bp (inclusive). It will be understood that these are not absolute upper and lower limits, but rather a practical working range. In one embodiment, the amplicons formed during PCR in compartments containing a target are 70-110 bp). In some embodiments, double-stranded nucleic acid is provided at a concentration of 0.01-100 ng/µl. In some embodiments, double-stranded nucleic acid is provided in a quantity of 1-100 ng.

In some embodiments, any one of the methods described herein comprises determining the quantity of single-stranded target sequences in the sample by assuming a mathematical correlation (e.g., a Poisson model) based on the number of compartments containing a target. The use of Poisson distribution models to determine the quantity of target in a sample using digital PCR is routinely applied by those skilled in the art.

In some embodiments, a mathematical correlation is a Poisson distribution. Some embodiments of any one of the methods disclosed herein further comprises determining the quantity of double-stranded target sequences in the sample by assuming that that quantity of double-stranded target is half that of single-stranded target, and dividing the estimated quantity of single-stranded target sequences by two. It is important to know the quantity of starting material as will be appreciated by those skilled in the art.

In some embodiments, a sample of formed single-stranded nucleic acid is divided into two or more reactions to measure two or more target sequences. In some embodiments, denaturing the double-stranded nucleic acid to form single-stranded nucleic acid results in 1.9-2 fold increase in the number of compartments in which a target is identified compared to PCR performed on double-stranded nucleic acid without denaturing the double-stranded nucleic acid prior to performing PCR. In other words, if a certain amount of double stranded DNA is required for an accurate measurement, then if that DNA is melted into single strands, one effectively doubles the amount of nucleic acid and, for example, two distinct reactions for different targets can be carried out. Conversely, if DNA is melted into single strands, then only one half as much material is needed to achieve the same degree of accuracy. In some embodiments, assaying by denaturing the double-stranded nucleic acid to form single-stranded nucleic acid and then compartmentalizing results in 1.9-2 fold increase in the number of compartments in which a target is identified compared to the number of compartments in which a target is identified when assaying the same amount of double-stranded nucleic acid under the same conditions but compartmentalizing without denaturing the double-stranded nucleic acid. In some embodiments, the double-stranded nucleic acid to be assayed is cell-free circulating DNA and the size of amplicons formed by isothermal amplification or PCR is 50-110 bp. In some embodiments of a method wherein the double-stranded nucleic acid is cell-free circulating DNA, assaying by denaturing the double-stranded nucleic acid to form single-stranded nucleic acid and then compartmentalizing results in a 1.6-1.7 fold increase in the number of compartments in which a target is identified compared to the number of compartments in which a target is identified when assaying the same amount of double-stranded nucleic acid under the same conditions but compartmentalizing without denaturing the double-stranded nucleic acid.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

FIG. 1A illustrates ddPCR, wherein two droplets can be identified as having targets, as compared to denaturation-enhanced digital-droplet PCR (dddPCR), wherein there are four droplets identified to have targets. Testing of BRAF using non-denatured DNA (first three bars) generates half the target-positive droplets ('events') as compared to using the same DNA immediately after denaturation (last three bars). FIG. 1B shows the effect of heat-denaturation of genomic DNA (gDNA) in PCR mastermix in ddPCR for BRAF V600E. The denaturation of the gDNA into the reaction mix almost doubled the number of positive counts in ddPCR, which are more than when denaturation of DNA was done before mixing with the ddPCR reagents. The number of total events was not affected by generating droplets with warmer reaction mixtures. FIG. 1C also shows effect of heat-denaturation of genomic DNA (gDNA) in PCR mastermix in ddPCR for BRAF V600E.

FIG. 9A shows that dddPCR incorporates a DNA denaturation step prior to droplet generation. A mixture of fragmented genomic DNA, primers, hydrolysis probes and ddPCR buffer is heated to denature the template, following which ssDNA molecules are partitioned into different droplets. Compared with standard ddPCR, data-positive droplets are doubled using dddPCR. FIG. 9B shows the use of end-repair to blunt the DNA strands in the case of DNA fragments having overhangs (e.g., as that found in circulating DNA). The two strands become blunted, leading to doubling of the positive droplets following dddPCR. Without end-repair the ratio of dddPCR/ddPCR data-positive droplets is less than 2 because primers may not bind to shorter DNA fragments. End-repair and denaturation are carried out sequentially in a single tube reaction. DNA fragments with gray bases (and marked with"x") represent mutated DNA.

FIG. 10A shows data for a sample having 0.5% mutations. FIG. 10B shows data for a sample having 1% mutations.

FIG. 11A shows a clustering pattern of a 5% mutant sample after ddPCR and dddPCR on the 2D-plots.

FIG. 11B shows the number of events (droplets) wherein target is detected for standard ddPCR with no denaturation, and 1-3 rounds of denaturation prior to ddPCR. FIG. 11C shows cycling protocols for 1, 2, and 3 rounds of denaturation prior to droplet formation.

FIG. 11D shows copies concentration after standard ddPCR, dddPCR protocol and 2 or 3 rounds of denaturation prior to ddPCR.

FIG. 12A is a demonstration of this concept. FIG. 12B shows ddPCR and dddPCR data for BRAF V600E using 10 ng of HTB-19 cell line gDNA serially diluted into wild type DNA (WT). Outer bars represent the standard error of the mean for the replicates; the inner error bar is the 95% confidence interval for the Poisson distribution. Each sample is composed of 4 merged replicates. RSE=relative standard error.

FIG. 14A shows data for standard cycling includes 10 minutes at 95° C. for polymerase activation before 50 cycles of amplification.

FIG. 14B shows data for cycling with delayed polymerase activation including 2 minutes at 95° C. followed by 3 cycles of amplification, then 10 minutes at 95° C. followed by 50 cycles of PCR. The outer bars represent the standard error of the mean for the replicates; the inner error bar is the 95% confidence interval for the Poisson distribution. Each sample is composed by 4 merged replicates.

FIG. 15A shows data for gDNA harboring the BRAF p.V600E mutation at 10% abundance, which was serially diluted in water and 10, 5, 2.5 and 1.25 ng of input was used in each reaction. The samples were analyzed in duplicates and the concentration measurements represent the merged wells for each sample. FIG. 15B shows the concentration fold-change (dddPCR/ddPCR) for wild-type and mutant copies.

FIG. 16A is a demonstration of this concept. FIG. 16B and FIG. 16C show the analysis of gDNA HD728 serially diluted in WT DNA using 30 ng (ddPCR, non-denatured), or split in two 15 ng samples (dddPCR, denatured) as DNA input: BRAF V600E and NRAS Q61K screened, respectively. Undiluted gDNA HD728 contains BRAF V600E and NRAS Q61K mutations at 8% and 5% allelic frequencies, respectively. Error bars represent the 95% confidence interval for the Poisson distribution. The dddPCR results represent merged wells for 2 replicates.

FIG. 18A shows the comparison between number of copies per µL of reaction obtained by ddPCR and dddPCR using a BRAF V600E assay. Different input of WT cfDNA and 5 ng input of end-repaired cfDNA were analyzed along with WT gDNA as control. FIG. 18B shows that a SNP rs1050171 assay was used to perform end-repair followed by dddPCR, using cfDNA with 5% of allele A. FIGS. 18C, 18D show that the concentration fold-change was calculated by dividing dddPCR by ddPCR values. End-repair and dddPCR were performed sequentially in a single tube reaction. The error bars represent the range of fold change among replicas.

FIGS. 19A-19C show end-repair and dddPCR performed in separated steps. A high amount of cfDNA (150 ng) was blunted with end repair enzyme mix, purified and then added to a ddPCR or dddPCR reaction. FIG. 19A shows data foir10 ng of end-repaired purified cfDNA and 10 ng of gDNA tested for BRAF V600E assay. FIG. 19B shows data for 3 ng of end repaired purified cfDNA tested for EGFR L858R. FIG. 19C shows that the concentration fold change (dddPCR/ddPCR) for cfDNA was lower than 2 for both assays, however the ratio ~2 is restored after cfDNA blunting, achieving similar ratios to that obtained for large-fragments of gDNA.

DETAILED DESCRIPTION OF THE INVENTION

Figure 1A:
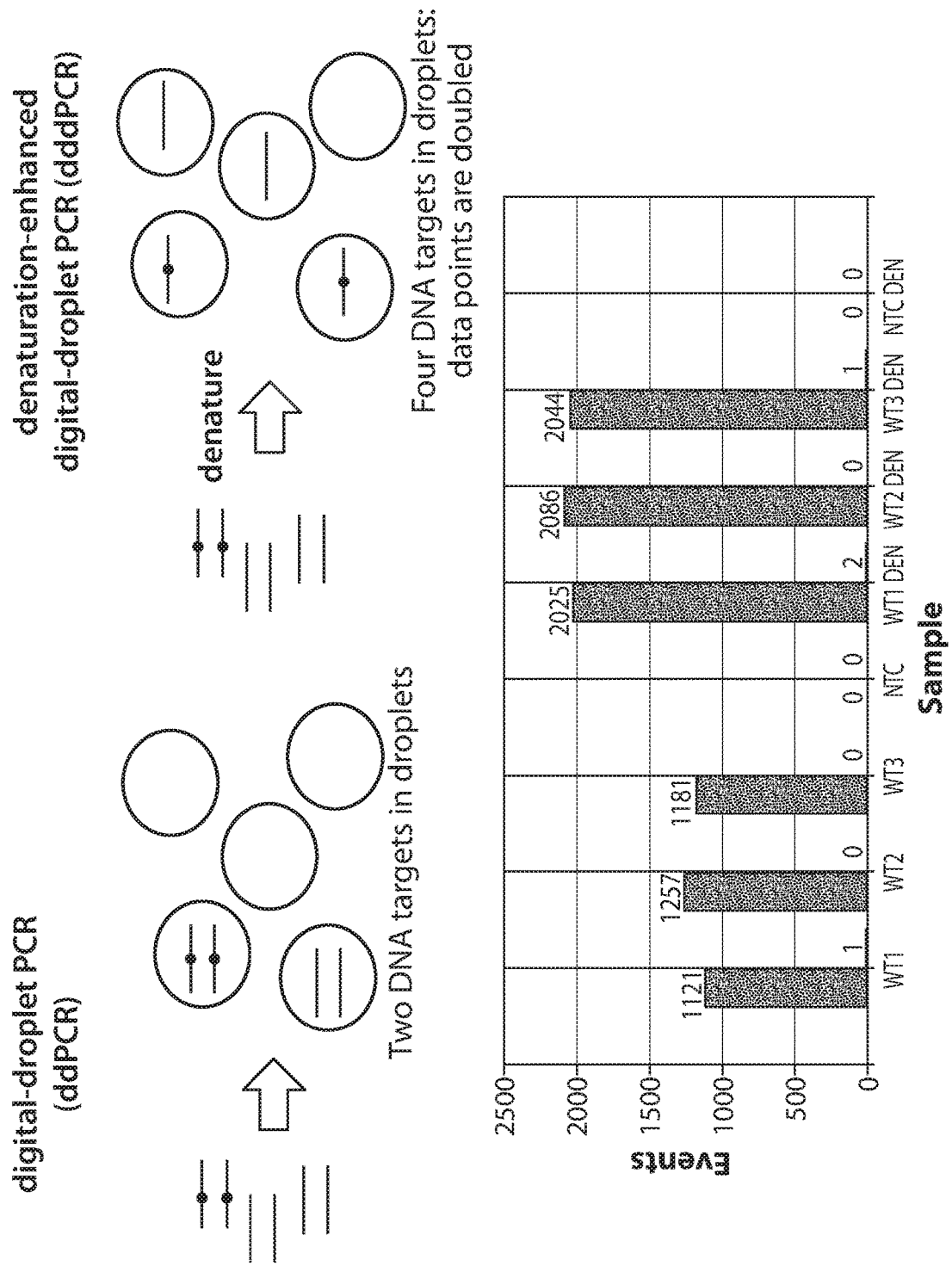
FIGS. 1A-1C show that denaturation of dsDNA prior to droplet formation doubles the data obtained during digital-droplet PCR (ddPCR).

In the era of personalized medicine, molecular analysis of small input clinical samples such as liquid biopsy-obtained circulating DNA, or of a specimen of a solid tumor are of great interest due to their broad potential as clinically significant biomarkers of disease. While real time PCR (1-6), mutation/methylation enrichment (7-14) and sequencing technologies (15-18) are widely used for detecting DNA alterations in liquid biopsies, interest in digital PCR (19) is rising rapidly in view of robust quantitative aspects of the technology and the emergence of commercial droplet digital PCR (ddPCR) platforms (11, 20-23). ddPCR has been implemented in diverse fields such as cancer biomarkers (24), viral load detection, prenatal screening, organ donor rejection, or library assessment for next generation sequencing (25,26). Detection of emerging resistance or minimal residual disease via ddPCR in liquid biopsies is also growing rapidly (27).

Despite progress, absolute quantification of nucleic acid targets using a digital approach (e.g., ddPCR technology) is restricted by the inherent problems associated with limited number of input DNA copies available for analysis (28). When just a few nanograms of circulating DNA are analyzed, the information obtained is affected by statistical sampling errors and the number of clinically relevant targets that can be analyzed is reduced. The paucity of starting material acts as a 'glass ceiling' in liquid biopsies since, irrespective how sensitive ddPCR techniques are, detection limits cannot be improved past the DNA input limitations. While pre-amplification of DNA can be applied to increase the material prior to ddPCR, this spoils absolute quantification and introduces a number of additional experimental problems (29).

Absolute Quantification of Nucleic Acid Target Sequences and Digitality

As referred to herein, "absolute quantification" of a nucleic acid target sequence (also referred to herein as a "target sequence" or "target") is the quantification of a target sequence in a sample of nucleic acid without the use of a reference sample the quantity of target sequence in which is known, or assumed. Typically, methods of quantifying a target sequence in a test sample of nucleic acid is done by comparing the output signal (e.g., fluorescence in real-time PCR) from the test sample to the output signal of a series of dilutions of a reference sample. While the quantity of target obtained by such methods is numerical, they are relative or semi-quantitative, rather than absolute, since they depend on the comparison to a reference sample. On the other hand, absolute quantification of a target sequence does not rely on comparison to a particular target in a reference sample.

As used herein, a "target" or "target sequence" is one or more base pairs in a nucleic acid that is desired to be detected, identified, and/or quantified. A target may be a wild-type sequence. In some embodiments, a target is a sequence that has copy number variation in a sample from a subject compared to samples from a control subject population. In some embodiments, copy number variation in a subject is linked to disease states and can be used to diagnose a condition in a subject or check the progress of a condition in a subject. Zhang et al. discuss examples of copy number variation of certain DNA targets and disease (Annu Rev Genomics Hum Genet. 2009; 10: 451-481), which is incorporated herein by reference in its entirety.

In some embodiments, a target sequence is a sequence to be identified or detected in a sample of nucleic acid from a subject of a first species that has been infected by a second species. In some embodiments, the identification of the target provides clues of the identity of the second species. A non-limiting example of this is detection of viral nucleic acid (e.g., Reoviridae) in a biological sample from a human subject.

In some embodiments, a target sequence is a mutant sequence (e.g., a single nucleotide polymorphism). In some embodiments, a "mutant sequence" refers to a nucleic acid that is less prevalent in nucleic acid samples from a particular population of subjects (e.g., adult male humans). In some embodiments, "mutant sequence" refers to a nucleic acid that is less prevalent in a nucleic acid sample than a corresponding wild type sequence. A "wild-type" sequence may be the more prevalent sequence in a particular population of subjects. The mutant target sequence typically makes-up less than 50% of the total amount of wild type sequence+mutant sequence in a sample. The mutant target sequence may be expressed at the RNA and/or DNA level 1: 10, 1: 15, 1:20, 1:25X, 1:30, 1:35, 1:40, 1:45, 1:50, 1:60, 1:70, 1:80, 1:90, 1: 100, 1: 150, 1:200× or less than the wild type sequence.

In some embodiments, a sample of double-stranded nucleic acid is DNA. In some embodiments, a double-stranded nucleic acid sample is RNA (e.g., double-stranded viral RNA). In some embodiments, a sample of double-stranded nucleic acid is genomic DNA or cDNA. In some embodiments, genomic DNA is cell-free circulating DNA. In some embodiments, a genomic DNA is obtained from a biological sample (e.g., blood, serum, plasma, urine, solid tissue, skin, hair, a buccal swab, a pulmonary brushing, or stool sample).

One way of performing absolute quantification of a target sequence is to perform a method of target identification/detection (e.g., real-time PCR, isothermal amplification, or sequencing) with digitality, or in a digital way. As referred to herein, a "digital" way of performing nucleic acid detection means to separate a sample of nucleic acid in which a target is to be detected into numerous partitions or compartments such that there is, on average, no more than one target-comprising nucleic acid in a compartment, and then performing an assay on each compartment to detect those containing a target. A majority of the compartments contain either one or none single-stranded nucleic acids comprising the target sequence such that Poisson's distribution can be assumed to be applicable to the distribution of targets in the compartments. Partitioning a sample in this way provides a means to absolutely quantify the target in the sample by using a mathematical correlation that provides a relation between the fraction of total partitions in which a target has been detected with the number of target copies per partition. Digital PCR (dPCR) is one example of a digital absolute quantification method.

As an example of dPCR, droplet dPCR technology is a dPCR method utilizing a water-oil emulsion droplet system. Droplets are formed in a water-oil emulsion to form the partitions that separate the template DNA molecules. The droplets serve essentially the same function as individual test tubes or wells in a plate in which the PCR reaction takes place, albeit in a much smaller format. The massive sample partitioning is a key aspect of the ddPCR technique. The Droplet Digital PCR System partitions nucleic acid samples into thousands of nanoliter-sized droplets, and PCR reaction conditions are carried out within each droplet, thereby amplifying a target-comprising nucleic acid when present in a compartment. This technique has a smaller sample requirement than other commercially available digital PCR systems, reducing cost and preserving precious samples.

ddPCR technology uses a combination of microfluidics and surfactant chemistries to divide PCR samples into water-in-oil droplets (Hindson et al. 2011). The droplets support PCR amplification of the template molecules they contain and use reagents and workflows similar to those used for most standard TaqMan probe-based assays. Following PCR, each droplet is analyzed or read to determine the fraction of target-positive droplets in the original sample. These data are then analyzed using mathematical models (e.g., Poisson statistics) to determine the target DNA template concentration in the original sample.

Droplet Digital PCR surpasses the performance of earlier digital PCR techniques by resolving the previous lack of scalable and practical technologies for digital PCR implementation. Serial dilution is laborious and introduces the possibility of pipetting error; competing chip-based systems rely on complex fluidics schemes for partitioning. Droplet Digital PCR addresses these shortcomings by massively partitioning the sample in the fluid phase in one step. The creation of tens of thousands of droplets means that a single sample can generate tens of thousands of data points rather than a single result, bringing the power of statistical analysis inherent in digital PCR into practical application.

Herein, "digital droplet PCR" and "droplet digital PCR" are used interchangeably. The following references provide more information about dPCR and ddPCR, each of which is incorporated herein by reference in their entirety:
1. Chen, R. et al. Cell 148, 1293-1307 (2012).
2. Tadmor, A. D., Ottesen, E. A., Leadbetter, J. R. & Phillips, R. Science 333, 58-62 (2011).
3. Wang, J. et al. Clin. Chem. 56, 623-632 (2010).
4. Lo, Y. M. et al. Proc. Natl. Acad. Sci. USA 104, 13116-13121 (2007).
5. Sykes, P. J. et al. Biotechniques 13, 444-449 (1992).
6. Vogelstein, B. & Kinzler, K. W. Proc. Natl. Acad. Sci. USA 96, 9236-9241 (1999).
7. Whale, A. S. et al. Nucleic Acids Res. published online, doi:10.1093/nar/gks203 (28 Feb. 2012).
8. Pekin, D. et al. Lab Chip 11, 2156-2166 (2011).
9. Patent publications US20110183330A1, US20090239308A1, WO2010018465A2, WO2016170109A1, WO2014186147A3, U.S. Pat. No. 9,896,717B2, which describe digital PCR and variations thereof. The methods disclosed herein are applicable to digital PCR as well as variations thereof.

Sensors (Basel). 2018 Apr. 20; 18(4)), which is herein incorporated by reference in its entirety, and attached herewith as Exhibit 1, provides a detailed explanation of digital PCR.

A non-limiting example of ddPCR follows. A PCR solution is made similarly to a standard real-time PCR (e.g., with TaqMan assay reagents, which consists of template DNA (or RNA), fluorescence-quencher probes, primers, and a PCR master mix, which contains DNA polymerase, dNTPs, $MgCl_2$, and reaction buffers at optimal concentrations). The PCR reaction mixture or solution is then divided into smaller reactions or partitions such that compartments containing the target contain only a single copy of the target, and PCR is then run on each partition individually. After multiple PCR amplification cycles, the samples are checked for signal (e.g., fluorescence) with a binary readout of "0" or "1." The fraction of total partitions with a detected target is recorded, which is equal to the number of partitions in which target was detected divided by the total number of partitions. The partitioning of the sample allows estimation of the number of different molecules by assuming that the molecule population follows the Poisson distribution, thus accounting for the possibility of multiple target molecules inhabiting a single partition. Using Poisson's law of small numbers, the distribution of target molecule within the sample can be accurately approximated allowing for a quantification of the target strand in the PCR product. Poisson distribution of the copies of target molecule per droplet (CPD) based on the fraction of fluorescent droplets (p), is represented by the function $CPD=-\ln(1-p)$. This model simply predicts that as the number of samples containing at least one target molecule increases, the probability of the sample containing more than one target molecule increases. In conventional PCR, the number of PCR amplification cycles is proportional to the starting copy number. In dPCR, however, the number of amplification cycles does not depend on the initial sample amount, eliminating the reliance on uncertain exponential data to quantify target nucleic acids and therefore provides absolute quantification.

Such digitality can be applied to any method (e.g., real-time PCR, isothermal amplification methods, or sequencing) of detecting one or more target sequences to obtain absolute quantification. Partitioning or compartmentalization of a sample of nucleic acid may be achieved in several ways, and such methods are known in the art (see e.g., Sensors (Basel). 2018 Apr. 20; 18(4)), attached herewith as Exhibit 1 A partitioning platform may be active or passive. Active platforms are microfluidic devices that rely on microfluidic valves for partitioning of a sample. Passive partitioning uses fluidic effects to create sub-volumes and does not rely on mechanical methods. Some non-limiting examples of forming compartments of nucleic acids are separation into microwell plates, capillaries, oil-in-water emulsion droplets, nanofluidic devices, or arrays of miniaturized chambers.

Denaturation-Enhanced Absolute Quantification by Digital Methods

A simple approach is described herein to enhance the information obtained via digital PCR technology when analyzing limited input DNA samples for mutations. As of its inception (19), digital PCR amplifies individual double stranded DNA molecules in distinct reaction compartments, then obtains signal readout from each compartment to reveal and quantify DNA mutations (30). Yet the information contained in double stranded DNA is redundant, as each mutated base appears in both sense and antisense strands of the original molecule. It was hypothesized (pursuant to making the invention) that by applying complete denaturation of double stranded DNA prior to droplet formation in ddPCR, one might double the number of positive droplets obtained from a given DNA amount and thereby enhance ddPCR analysis of clinical samples. This was found, surprisingly, to consistently be the case.

Accordingly, provided herein is a method of enhancing absolute quantification of a target sequence using digital techniques. In some embodiments, a method of enhancing absolute quantification of a target sequence comprises denaturing a sample of double-stranded nucleic acid to form single-stranded nucleic acid, and performing absolute quantification on the single-stranded nucleic acid. In some embodiments, absolute quantification is achieved by digitally applying a method of detecting a target. In some embodiments, a method of enhancing absolute quantification of a target sequence comprises denaturing a sample of double-stranded nucleic acid to form single-stranded nucleic acid, and performing digital absolute quantification on the single-stranded nucleic acid. In some embodiments, a method comprises denaturing a sample of double-stranded nucleic acid to form single-stranded nucleic acid, partitioning the sample of formed single-stranded nucleic acid into a multitude of compartments (or partitions), wherein a vast majority of the compartments contain either no target sequence or one single-stranded target sequence, and assaying for the target in each of the compartments. In some embodiments, limited dilution is applied to a sample of single-stranded nucleic acid formed by denaturing a sample of double-stranded nucleic acid before performing a method (or an assay) to detect a target in each compartment.

In some embodiments, a method of enhancing absolute quantification of a target sequence comprises (a) denaturing a double-stranded nucleic acid in a sample to form single-stranded nucleic acid, wherein the double-stranded nucleic acid comprises a target sequence; (b) partitioning the sample of formed single-stranded nucleic acid into a multitude of compartments, wherein any compartment containing a target single-stranded nucleic acid contains no more than one such target single-stranded nucleic acid; and (c) detecting the number of compartments containing the target sequence.

In some embodiments, assaying for the target sequence in each of the compartments comprises performing amplification reactions in each of the compartments, thereby amplifying target-comprising single-stranded nucleic acids if present in a compartment. In some embodiments, assaying for a target comprises running or performing sequencing reactions in each of the compartments.

In some embodiments, an amplification reaction in a compartment comprises PCR. Accordingly, in some embodiments, a method of enhancing absolute quantification of a target sequence in sample of double-stranded nucleic acid as disclosed herein further comprises adding one or more PCR reagents (e.g., forward and reverse primers, a polymerase, hydrolysis probes, and deoxynucleotide triphosphates (dNTP)) to the sample. In some embodiments, PCR reagents are added to the sample containing double-stranded nucleic acid prior to denaturing the double-stranded nucleic acid to single-stranded nucleic acid. In some embodiments, PCR reagents are added to a sample of nucleic acid after double-stranded nucleic acid has been denatured to single-stranded nucleic acid.

In some embodiments, PCR that is performed on each compartment comprises:
(a) activating a polymerase;
(b) denaturing nucleic acid, or applying denaturing conditions so as to denature nucleic acid if present in a compartment;
(c) annealing of primers to single-stranded nucleic acid present in a compartment, or applying a temperature that allows primers to anneal to single-stranded nucleic acid;
(d) extending those primers that anneal to form double-stranded nucleic acid; and
(e) repeating steps (b) to (d) at least once (e.g., 1, 2, 3, 4, 5, 6, 7, 8, 9, 10, 20, or 30 or more times).

In some embodiments, steps (b) to (d) are repeated at least 9 times. In some embodiments, steps (b) to (d) is repeated at least 19 times. In some embodiments, steps (b) to (d) are repeated at least 39 times. In some embodiments, steps (b) to (d) are repeated at least 49 times. In some embodiments, steps (b) to (d) are repeated 1-100 times (e.g., 1-10, 1-30, 1-50, 5-20, 10-30, 10-50, 20-100, 30-100, 40-100, 50-100, 40-60, 40-60, 60-80, or 80-100 times).

In some embodiments, the polymerase is activated by heating it. Commercially available polymerases are provided with optimal activation conditions that can be used to activate a polymerase. Moreover, conditions for activation of polymerases that are not commercially available are also known in the art (see e.g., www.neb.com/products/per-qper-and-amplification-technologies/onetaq-dna-polymerases/onetaq-dna-polymerases). In some embodiments, a polymerase for PCR is activated by exposing the compartment in which the polymerase is present to a temperature of 90-97° C. (e.g., 90-92, 90-94, 90-95, 90-97, 92-97, 94-96, or 95-97° C.) for 0.1-10 (e.g., 0.1-10, 0.1-5, 0.1-2, 0.1-1, 0.1-0.5, 0.5-10, 1-10, 2-10, 3-8, 4-6, 5-10, 5-6, 6-10, 7-10, 8-10, or 9-10) minutes.

In some embodiments, the denaturation step or condition in the PCR of each compartment comprises exposing the compartment to a temperature of 90-98° C. (e.g., 90-98, 90-92, 90-94, 90-96, 90-91, 91-95, 94-96, 94-98, 94-95, 95-98, 95-97, or 96-98° C.) for 2-120 (e.g., 2-120, 2-5, 2-10, 2-20, 2-30, 2-40, 2-50, 2-60, 2-90, 5-10, 5-30, 5-60, 5-90, 5-120, 10-120, 10-30, 10-60, 10-90, 20-120, 2-60, 20-30, 30-120, 30-60, 30-90, 60-90, 60-120, or 90-120) seconds. It is to be understood that "exposing the compartment" to a particular temperature means to expose the contents of the compartment to that particular temperature.

In some embodiments of any one of the methods disclosed herein wherein a target is assayed in a compartment using PCR, primer annealing and extension comprises exposing the compartment to a temperature of 50-70° C. (e.g., 50-70, 50-55, 50-60, 55-60, 60-70, 60-65, 65-70, or 55-65° C.) for 5-120 (e.g., 2-120, 2-5, 2-10, 2-20, 2-30, 2-40, 2-50, 2-60, 2-90, 5-10, 5-30, 5-60, 5-90, 5-120, 10-120, 10-30, 10-60, 10-90, 20-120, 2-60, 20-30, 30-120, 30-60, 30-90, 60-90, 60-120, or 90-120) seconds. The annealing temperature of the primers will depend on the length and sequence of the primers. The annealing temperature of the primers to complementary sequence can be calculated based on the sequence using algorithms (e.g., http://tmcalculator.neb.com/#!/main) and are also provided by vendors who manufacture primers and sell them. Primers used in the amplification of any one of the method disclosed herein are similar to primers used in standard PCR or digital PCR. Primers are designed so that their length is long enough for adequate specificity and short enough for primers to bind easily to the template at the annealing temperature. In some embodiments, primers are 12-30 bp (e.g., 12-30, 14-28, 16-24, or 18-22 bp) long. In some embodiments, primers are 18-22 bp (e.g., 18, 19, 20, 21, or 22 bp) long.

dPCR may be performed using either DNA intercalating dyes or hydrolysis-based probes, both of which are known in the art (see e.g., Exhibit 1).

Multiplexed dPCR is also contemplated herein in which more than one target (e.g., 1, 2, 3, 4, 5, 6, 7, 8, 9, 10, 11, 12 or more targets) is assayed for in each compartment. In this embodiment, the same parameters would apply, that is if a compartment contained a target, it would contain only one target. Variations of PCR (e.g., multiplexed PCR, nested PCR, or co-amplification at lower denaturation temperature-PCR or variations thereof) are also contemplated herein.

In some embodiments, a polymerase for PCR is deactivated after completion of the PCR reactions. In some embodiments, a polymerase is deactivated by exposing a compartment to a temperature that will denature the polymerase, for example, exposure to a temperature of at least 90-98° C. (e.g., 90-98, 90-92, 90-94, 90-96, 90-91, 91-95, 94-96, 94-98, 94-95, 95-98, 95-97, or 96-98° C.) for 2-300 seconds (2-300, 2-5, 2-10, 2-20, 2-30, 2-60, 2-120, 2-180, 2-240, 5-10, 5-20, 5-30, 5-60, 5-120, 5-18-, 5-240, 5-300, 10-20, 10-30, 30-60, 30-120, 60-120, 60-180, 60-240, 60-300, 120-180, 120-240, 120-300, or 180-300 seconds).

In some embodiments, assaying for a target in a compartment comprises an isothermal amplification techniques. To circumvent the need to cycle temperatures, various isothermal DNA amplification techniques (e.g., transcription mediated amplification, nucleic acid sequence-based amplification, signal mediated amplification of RNA technology, strand displacement amplification, rolling circle amplification, loop-mediated isothermal amplification of DNA, isothermal multiple displacement amplification, helicase-dependent amplification, single primer isothermal amplification, and circular helicase-dependent amplification) have been developed, and may be used in any one of the methods disclosed herein. Gill and Ghaemi discuss various isothermal amplification methods in Nucleosides, Nucleotides, and Nucleic Acids, 27:224-243, 2008, which is incorporated by reference herein in its entirety. In some embodiments, an isothermal amplification method comprises:

(a) forming a reaction mixture comprising:
  the input dsDNA,
  a nicking nuclease active at a temperature T, wherein the nicking nuclease incorporates random single-stranded breaks into dsDNA,
  a strand-displacing polymerase active at the temperature T, wherein the strand-displacing polymerase recognizes a single-stranded break in dsDNA, and, in the presence of nucleotide triphosphates, extends the single strand having the break and displaces the ssDNA fragment that is 3' relative to the break, and
  deoxynucleotide triphosphates (dNTPs), wherein the dNTPs comprise one or more the following dNTPs: deoxyadenosine triphosphate (dATP), deoxythymidine triphosphate (dTTP); deoxycytosine triphosphate (dCTP), and deoxyguanosine triphosphate (dGTP); and
(b) subjecting the reaction mixture to the temperature T under which both the nicking nuclease and the strand-displacing polymerase are active, thereby forming the probes.

Accordingly, in some embodiments, a method of enhancing absolute quantification of a target sequence in sample of double-stranded nucleic acid as disclosed herein further comprises adding one or more reagents for isothermal amplification (e.g., a nicking nuclease, a strand-displacing polymerase, and deoxynucleotide triphosphates (dNTPs)) reagents to the sample. In some embodiments, reagents for isothermal amplification are added to the sample before double-stranded nucleic acid is denatured to form single-stranded nucleic acid. In some embodiments, reagents for isothermal amplification are added to the sample after double-stranded nucleic acid is denatured to form single-stranded nucleic acid.

When amplification methods are used for assaying for a target, size of amplicons formed in each of the compartments is 15-1000 bp (e.g., 15-1000, 15-100, 20-1000, 20-800, 20-500, 20-400, 20-200, 20-100, 50-100, 50-200, 50-400, 50-500, 50-600, 50-110, 50-120, 78-111, 70-200, 80-150, 100-200, 120-180, or 150-200, bp). In some embodiments, an amplicon is 50-120 (e.g., 50-110, 50-120, 70-110, or 80-100 bp). In some embodiments, the concentration of double-stranded nucleic acid in a sample is 0.01-100 ng/µl (e.g., 0.01-0.1, 0.1-1, 1-10, 10-100, 0.01-1, 0.01-10, 0.1-10, or 1-100 ng/µl). In some embodiments, the concentration of double-stranded nucleic acid in a sample is 1-100 ng (e.g., 1-10, 10-100, 10-20, 20-30, 20-40, 30-50, 40-60, 50-70, 50-80, 50-100, 60-100, 80-100, or 90-100 ng).

Any one of the methods disclosed herein may further comprise determining the quantity of single-stranded nucleic acid target sequences in a sample by (1) assuming a mathematical correlation (e.g., Poisson's distribution) between the fraction of total number of compartments wherein a target is identified and the number of target sequences per compartment, (2) estimating the number of target sequences par compartment using the mathematical correlation, and (3) calculating the quantity of single-stranded target sequences in the sample by multiplying the number of target sequences per compartment and the total number of compartments. The quantity (e.g., in number or mass) of double-stranded target sequences in the original sample would be half the quantity (e.g., in number or mass) of the calculated single-stranded target sequences.

In some embodiments, initially denaturing double-stranded nucleic acid to form single-stranded nucleic acid in compartments results in 1.9-2 fold increase in the number of compartments in which a target is identified (i.e. positive compartments) compared to the prior art circumstance where each compartment initially contained the corresponding double-stranded nucleic acid. In some embodiments, denaturing double-stranded nucleic acid to form single-stranded nucleic acid results in 1.9-2 fold increase in the number of compartments in which a target is identified (i.e. positive compartments) compared to when assaying for target is done under the same conditions but without denaturing double-stranded nucleic acid to form single-stranded nucleic acid. In some embodiments, denaturing double-stranded nucleic acid to form single-stranded nucleic acid in compartments results in 1.5-2 fold (e.g., 1.4-2 fold, 1.5-2 fold, 1.6-2 fold, 1.7-2 fold, 1.8-2 fold, or 1.9-2 fold) increase in the number of compartments in which a target is identified (i.e. positive compartments) compared when assaying is performed without converting double-stranded nucleic acid to single-stranded nucleic acid under the same conditions. In some embodiments, initially denaturing double-stranded nucleic acid to form single-stranded nucleic acid in compartments results in more than 1.4 fold (e.g., more than 1.4 fold, more than 1.5 fold, more than 1.6 fold, more than 1.7 fold, more than 1.8 fold, more than 1.9 fold, or more than 1.95 fold) increase in the number of compartments in which a target is identified (i.e. positive compartments) compared when assaying is performed without converting double-stranded nucleic acid to single-stranded nucleic acid under the same conditions.

It is to be understood that if a sample of double-stranded nucleic acid comprises a mixture of double stranded DNA molecules and single stranded DNA molecules, then by denaturing the double-stranded nucleic acid in the sample as described herein will lead to an increase somewhere in between 1.0-2.0 (e.g., 1, 1.1, 1.2, 1.3, 1.4, 1.5, 1.6, 1.7, 1.8, 1.9, 2, 1.0-2.0, 1.2-1.8, 1.0-1.5) fold increase in the number of compartments in which a target is identified compared to assaying (e.g., using PCR) without denaturing the double-stranded nucleic acid prior to performing PCR. The exact fold increase will depend on the fraction of DNA molecules that are single stranded relative to double stranded. Thus, for example, if half the molecules are double stranded and half are single stranded, then the fold increase in target-positive compartments by denaturing the double-stranded nucleic acid will be 1.5 fold, since half the molecules (dsDNA) will give a 2-fold increase and the other half (ssDNA) will give no increase.

Methods of Denaturation

As disclosed herein, denaturing of double-stranded nucleic acid means the separation of sense and antisense strands to form single-stranded nucleic acid. Methods of denaturing nucleic acid is known in the art. Some non-limiting examples by which double-stranded nucleic acid may be denatured are by application of heat, i.e. thermal denaturation (e.g., by heating to a temperature of at least 95° C.), pH-based denaturation via exposure to NaOH, exposure to organic buffers such as formamide, DMSO and other compounds such as salt, and exposure to enzymes (e.g., helicases) that denature the DNA. The stronger the concentrations of denaturing reagent or parameter (e.g., NaOH or heat), the shorter the time required for the nucleic acid to be denatured. The length of the nucleic acid can also affect the length of the denaturing treatment that is needed. For example, heating at 95° C. may take longer to denature a sample of nucleic acid compared to heating the same sample to temperature of 99° C.

It should be noted that if a sample of double-stranded DNA is denatured after the addition of assay reagents (e.g., PCR reagents), the denaturing conditions should be compatible with the retention of activity of the assay reagents (e.g., enzymes such as polymerases, and nicking enzymes). If activity of assay reagents is not compatible with the denaturing conditions, the assay reagents are either added or supplemented after the denaturation step.

Blunt End Repair

As described above and exemplified in the Examples below, amplification using only a sense or only an anti-sense DNA strand in a droplet is likely to produce the same number of positive droplets as the corresponding double stranded molecule, provided the two strands are of equal size to begin with (blunt-ended DNA, see e.g., FIG. 9A). If, on the other hand, DNA is randomly fragmented with unequal strands (i.e. has overhangs), as in cell-free circulating DNA, then placing each strand in a separate droplet may not double the detection (e.g., ddPCR) signal, since the shorter strand may not bind the amplification reagents (e.g., primers for PCR). Accordingly, any one of the methods disclosed herein may comprise end-repair of double-stranded nucleic acid fragments prior to denaturation to form single-stranded nucleic acid. End-repair means an extension of a first strand which has a shorter end compared to the second strand to which is it partially complementary so that the overhang on the second strand becomes shorter or disappears entirely.

In some embodiments, producing blunt ends comprises treating double-stranded nucleic acid with end-repair enzyme (e.g., a T7 DNA polymerase, a T4 DNA polymerase, or a Klenow fragment). In some embodiments, an end-repair enzyme is separated from double-stranded nucleic acid fragments the ends of which have been repaired by filtration or size-exclusion. In some embodiments, an end-repair enzyme can be separated from double-stranded fragments by affinity purification using either a tag (e.g., c-myc, or Flag tag) on the enzyme or a tag or index on the double-stranded nucleic acid fragments.

In some embodiments, the end-repair step and the denaturing step are carried out in the same reaction vessel. In some embodiments, end repair of double-stranded nucleic acid fragments and denaturing them to form single-stranded nucleic acid is performed in the same reaction vessel without purifying out or removing an end-repair enzyme.

In some embodiments, an end-repair enzyme is inactivated rather than being removed. In some embodiments, an end-repair enzyme is inactivated by denaturation. In some embodiments, the denaturation of the end-repair enzyme comprises the same steps as denaturation of double-stranded nucleic acid. In some embodiments, end-repair enzyme inactivation comprises exposing an enzyme to a temperature of at least 65° C. (e.g., at least 65° C., at least 68° C., at least 70° C., at least 80° C., at least 85° C., at least 90° C., or at least 95° C. or more) for a period of time that reduces the activity of the enzyme by at least 50% (e.g., at least 50%, at least 60%, at least 70%, at least 80%, at least 90%, at least 95%, at least 98%, at least 99%, or at least 99.9% or more). In some embodiments, an end-repair enzyme is held to a temperature of at least 65° C. for 0.1 minutes to 60 minutes (e.g., 0.1-30, 0.1-1, 0.5-1, 1-2, 1-5, 2-5, 5-10, 2-10, 10-15, 15-30, 10-30, 1-60, 5-60, 10-60, 15-40, 20-40, 30-50, 30-40, 30-60, 45-60, or 50-60 minutes).

Limiting the Damage of Single-Stranded Nucleic Acid

Double-stranded nucleic acids are generally more stable than single-stranded nucleic acids. Therefore, denaturing double-stranded nucleic acids to form single-stranded nucleic acid makes the nucleic acid susceptible to degradation. In order to reduce the chance of degradation of single-stranded nucleic acid once formed, any one of the methods disclosed herein may reducing the delay between formation of single-stranded nucleic acid and partitioning of the nucleic acid into compartments, and/or reducing the delay between partitioning of the single-stranded nucleic acid and assaying for a target in each compartment. In some embodiments, once single-stranded nucleic acid is partitioned into compartments, the single-stranded nucleic acid is, without delay, converted to double-stranded nucleic acid to avoid degradation. In some embodiments, to quickly convert the single-stranded nucleic acid to double-stranded nucleic acid, the polymerase for PCR is activated partially (e.g., so that activity of the polymerase is less than 90%, less than 80%, less than 70%, less than 60%, less than 50%, less than 40%, less than 30%, less than 20%, or less than 10% of complete or highest possible activity of the polymerase) by exposing the compartment to its activation temperature (e.g., 90-97° C.) for a short period of time, e.g., no more than 0.1-2 minutes (e.g., 0.1-0.2, 0.1-0.3, 0.1-4, 0.1-0.5, 0.1-0.6, 0.1-0.7, 0.1-0.8, 0.1-0.9, 0.1-1, 0.2-0.5, 0.4-0.8, 0.4-1, 0.8-1.2, 1-1.2, 1-1.5, 1-2, 1.2-2, 1.4-2, 1.5-2, 1.6-2, 1.8-2, or 0.5-1.5 minutes). In some embodiments, such a quick activation of a polymerase is followed by 2-8 cycles of denaturation and primer annealing and extension to convert partitioned single-stranded nucleic acid to double stranded nucleic acid. In some embodiments, quick formation of double-stranded nucleic acid in this way is followed by a longer and more complete activation of a polymerase and more cycles of denaturation and primer annealing and extension.

Single Target Analyses

In some embodiments, any one of the methods disclosed herein is used to analyze a single target. In some embodiments of applying any one of the methods disclosed herein to analyzing a single target in a sample of double-stranded nucleic acid, half of a given sample or aliquot of a given sample can be used to detect a target. This is because the denaturation of double-stranded nucleic acid to single stranded nucleic acid doubles the quantity of target that can be analyzed. If instead of using only half of the sample for analysis, the entire sample is used for analysis after forming single strands of nucleic acid, the error associated with the estimation of target quantity is reduced. If any one of the methods disclosed herein is used to detect a mutation, the confidence in calling the mutation is increased because the confidence internal is decreased (e.g., by 2-10%, 2-20%, 5-10%, 10-20%, 20-50%, 40-60% 50-90%, 60-80%, 80-90%, or more than 90%).

Figure 4:
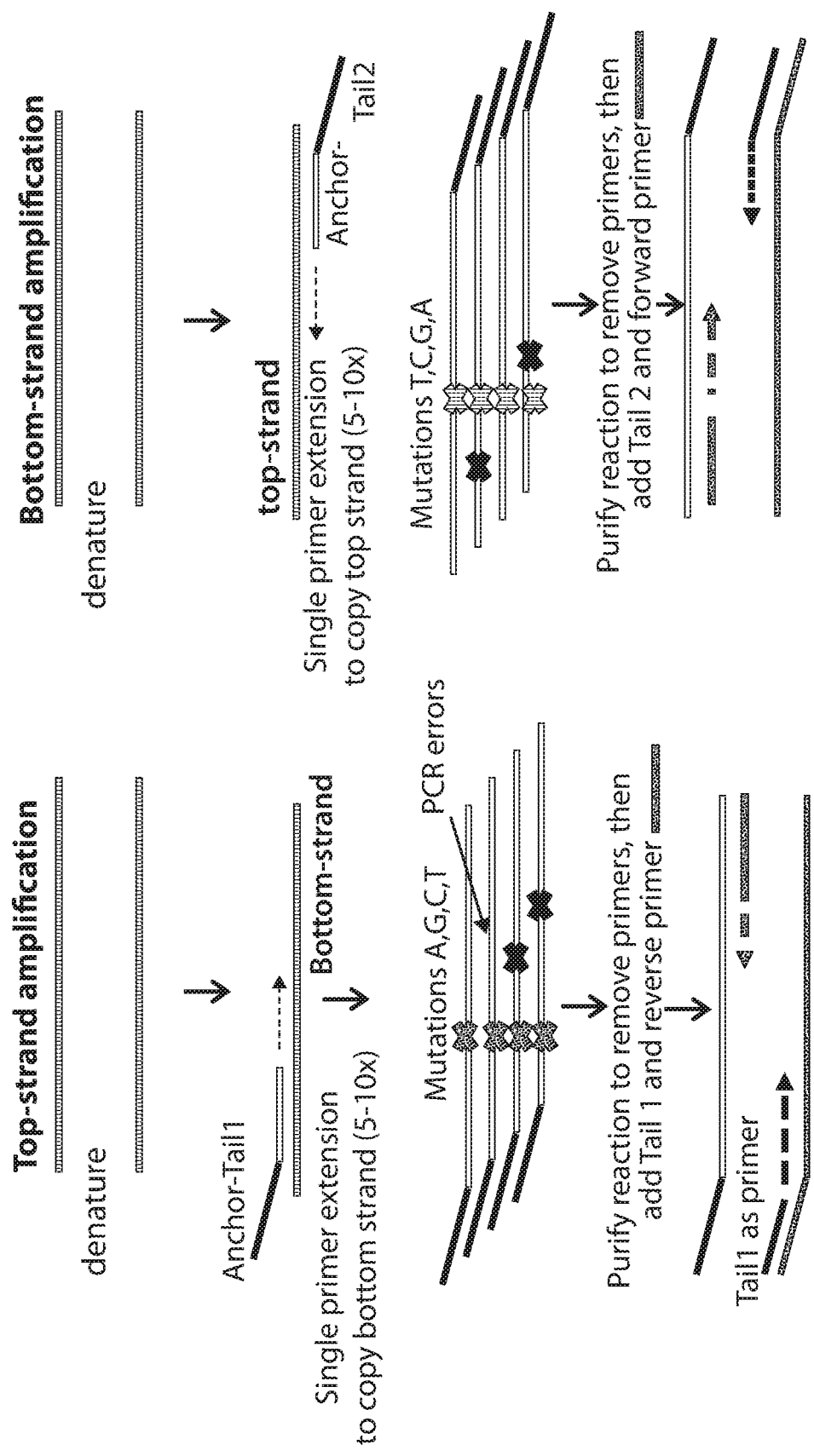
FIG. 4 shows top and bottom strand ddPCR/qPCR/sequencing (TaB-PCR) for amplifying separately the top or the bottom strand directly from genomic DNA. The two products can be used for library generation using different sample index, then mixed and sequenced together. Genomic DNA, Formalin-fixed paraffin embedded (FFPE) or circulating DNA are split in two halves, and two distinct reactions are performed, one for either the top or bottom strand. Errors are distinguished from top strand synthesis vs. errors from bottom strand synthesis. The presence of top strand mutations and simultaneous presence of bottom strand mutations are checked by running two reactions in parallel. 'Mutations' (errors) are sequenced, compared and eliminated if not present in both reactions.

In some embodiments, a single target may be analyzed by denaturing double-stranded nucleic acid into single-stranded nucleic acid, splitting the formed single-strands into two aliquots, and then detecting the target in the sense strand in the first aliquot and the antisense strand in the second aliquot (as shown in FIG. 4). This way, if a mutation is not called in both the sense and antisense strands, it can be discarded as noise or detection (e.g., PCR) error. In this way, any of the methods disclosed herein can be used to increase the confidence of calling a mutation in a sample.

Multiple Target Analyses and Separate Analyses of Sense and Antisense Strands

In some embodiments, a sample of double-stranded nucleic acid is aliquoted, either before or after converting to single strands, and each aliquot is used to detect a different target. This can be done because denaturing double-stranded nucleic acid to form single-stranded nucleic acid increases the effective amount of target that can be detected in a sample.

Figure 5:
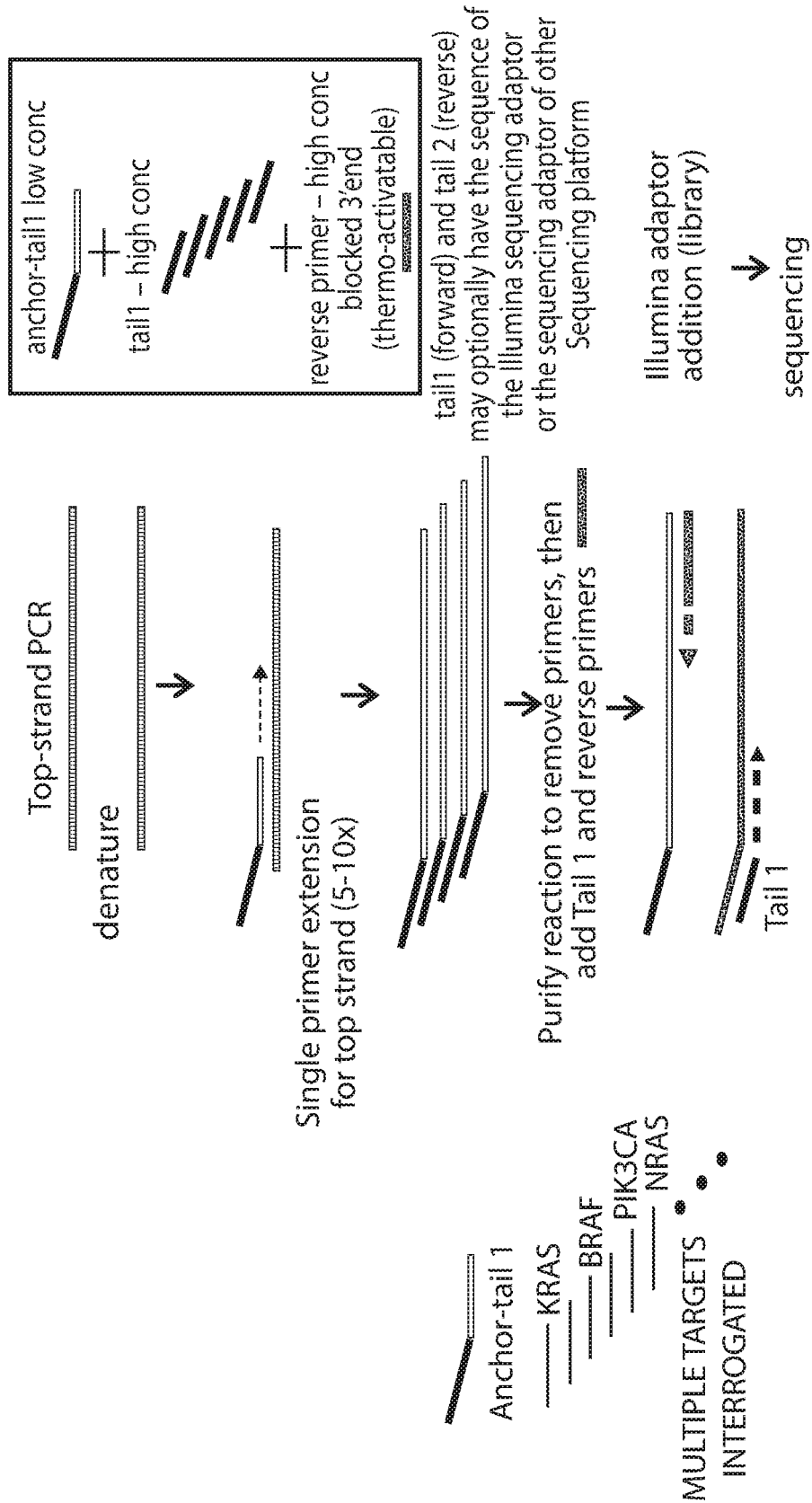
FIG. 5 illustrates multiplexed top and bottom strand ddPCR/qPCR/sequencing (mTaB-PCR) in which amplification of the top strand occurs by using anchor-tails that bind to different targets but all have the same tail on the 5-end. A corresponding reaction can be done to amplify the bottom strand in a multiplexed-target manner. Genomic DNA, FFPE or circulating DNA are split in two halves. Tail 1 (forward) and tail 2 (reverse) may optionally have the sequence of the Illumina sequencing adaptor or the sequencing adaptor of other sequencing platform.
Figure 6:
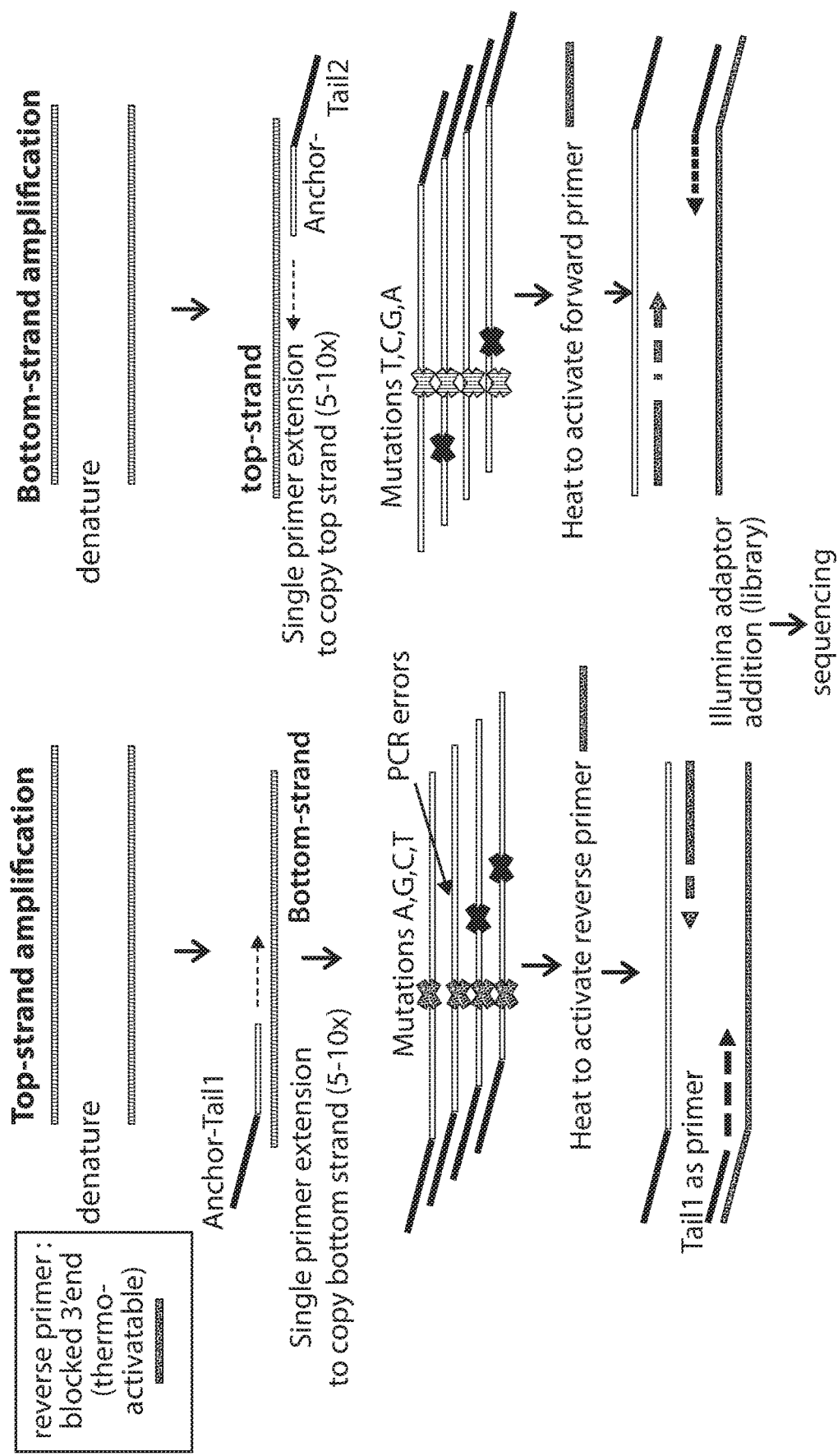
FIG. 6 shows single-tube top and bottom strand amplification, in which either the top or the bottom strand is amplified directly from genomic DNA. Genomic DNA, FFPE or circulating DNA are split in two halves, and two distinct reactions are performed, one for each strand. Errors are distinguished from top strand synthesis vs. errors from bottom strand synthesis. The presence of top strand mutations and simultaneous presence of bottom strand mutations at same position are checked by running two reactions in parallel. 'Mutations' (errors) are sequenced, compared and eliminated if not present in both.
Figure 7:
FIG. 7 illustrates relative concentrations of various primers in single tube reaction. Tail 1 (forward) and tail 2 (reverse) may optionally have the sequence of the Illumina sequencing adaptor or the sequencing adaptor for other sequencing platform.
Figure 7:
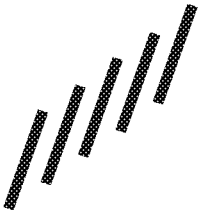
Figure 7:

Multiple targets (e.g., 2, 3, 4, 5, 6, 7, 8, 9, 10 or more targets) can be detected using the approach described above wherein an aliquot of a sample is used to detect a target in a sense strand which another aliquot is used to detect a target in the antisense strand. In some embodiments, sense and antisense strands are separated by denaturation, after which a sense or antisense assay (e.g., single primer extension by PCR) is used to amplify the region of nucleic acid in which various targets are expected to be found (see e.g., FIGS. 5-7).

Regents and Kits for Denaturation-Enhanced Absolute Quantification by Digital Methods Contemplated herein are also reagents and kits for performing any one of the methods disclosed herein. In some embodiments, a kit comprises one or more containers comprising reagents for denaturation of double-stranded nucleic acid (e.g., NaOH, or salt) either together in one container or in separate containers. In some embodiments, a kit as contemplated herein comprises a container comprising reagents for denaturation of double-stranded nucleic acid, and a one or more containers comprising assay reagents (e.g., PCR reagents or isothermal amplification reagents). In some embodiments, any one of the kits disclosed herein comprises one or more containers comprising reagents for end-repair of double-stranded nucleic acid.

EXAMPLES

Example 1

In the era of personalized medicine, DNA mutation or DNA copy number detection methods that target DNA sites known to influence therapy response or clinical outcome entice a great interest. For example, there is mounting evidence that tumor mutations identified in circulating-free DNA (cfDNA) can potentially act as a powerful liquid biopsy based diagnostic tool[1-5]. Similarly, DNA copy number differences can reveal crucial aspects of tumor biology and can be predictive, and DNA copy number differences in cfDNA can reveal the fraction of circulating DNA coming from the tumor. Clinical studies indicate the use of cfDNA to complement[6] or replace[2] tissue biopsies. Rare mutations identified in cfDNA via digital droplet PCR (ddPCR) or massively parallel sequencing (MPS) can lead to changes in clinical practice[7]. Interest in digital PCR is rising in view of the unique aspects of the technology and the emergence of commercial droplet digital PCR (ddPCR) platforms. ddPCR has been implemented in a variety of fields such as cancer biomarker and viral load detection, fetal screening or library quantification for next generation sequencing. One of the most common ddPCR applications is in the detection of known DNA variants present within a large excess of wild type DNA, for instance in DNA from heterogeneous samples that harbor sub-clonal populations of mutated tumor cells. Despite its promise, technical hurdles persist. The limited amount of cfDNA obtained from a standard blood draw and the excess amount of circulating wild-type (WT) DNA are persistent issues that often compromise the diagnostic results. For example, a ddPCR reaction for detection of a mutant DNA target (e.g., KRAS) requires at least 10 ng input DNA. If two or three targets (e.g., BRAF, KRAS, NRAS) are to be tested for mutations, three times the amount of DNA is required. And yet, frequently the amount of circulating DNA collected from a standard blood draw does not exceed 10 ng, thus limiting the amount of information that can be obtained for mutation-based diagnostic purposes. While in principle it may be possible to first amplify the original material and then test multiple targets from the amplified product, amplification methods such as polymerase chain reaction are known to occasionally introduce errors via mis-incorporation, resulting to false positive mutations.

A simple method that would allow an increase in the number of assays that can be performed from a limited clinical sample without introducing errors and without many additional steps would be of high utility in the burgeoning field of liquid biopsy and mutation-testing using circulating DNA or when using DNA from any other source like a fine-needle biopsy (FNA), urine, etc.

This disclosure provides a simple and effective method to double the information obtained from a DNA sample interrogated for mutations or for DNA copy number differences. DNA Contains Redundant Information on Two Strands as Regards to Mutations: A Given Mutation is Contained on Both Strands The disclosed technology is based, at least in part, on the realization that the information sought (DNA mutations) is present on both top and bottom strands and that this 'double record of mutations' is not necessarily needed for genetic testing. Given that just a single strand containing the mutation is enough to identify presence of the DNA alteration of interest, it is possible to separate the two DNA strands via denaturation, thereby doubling the original DNA molecules that can provide information. Accordingly, as an example, following denaturation, one may divide the sample in two portions that will contain an equal number of (singly) mutated DNA targets as the original, non-denatured sample which contained 'doubly mutated' targets. Then one may screen each portion for a distinct DNA target (e.g., BRAF and KRAS), thereby doubling the amount of information obtained from a sample that would otherwise only suffice for screening of a single target (e.g., BRAF only).

Similarly, for DNA copy number difference estimation, applying DNA denaturation prior to droplet generation doubles the data points out of which one infers these differences; by doubling the data points the accuracy for calculating copy number differences increases. For example, the relative error out of N observations when Poisson statistics apply is $\sqrt{N}/N$. Thus if one has 10 data points the relative error is higher than if one has 20 data points, etc. Accordingly, by doubling the droplets that provide positive events out of each DNA nanogram tested one obtains higher accuracy in copy number estimation.

Application in Digital PCR

Figure 1B:
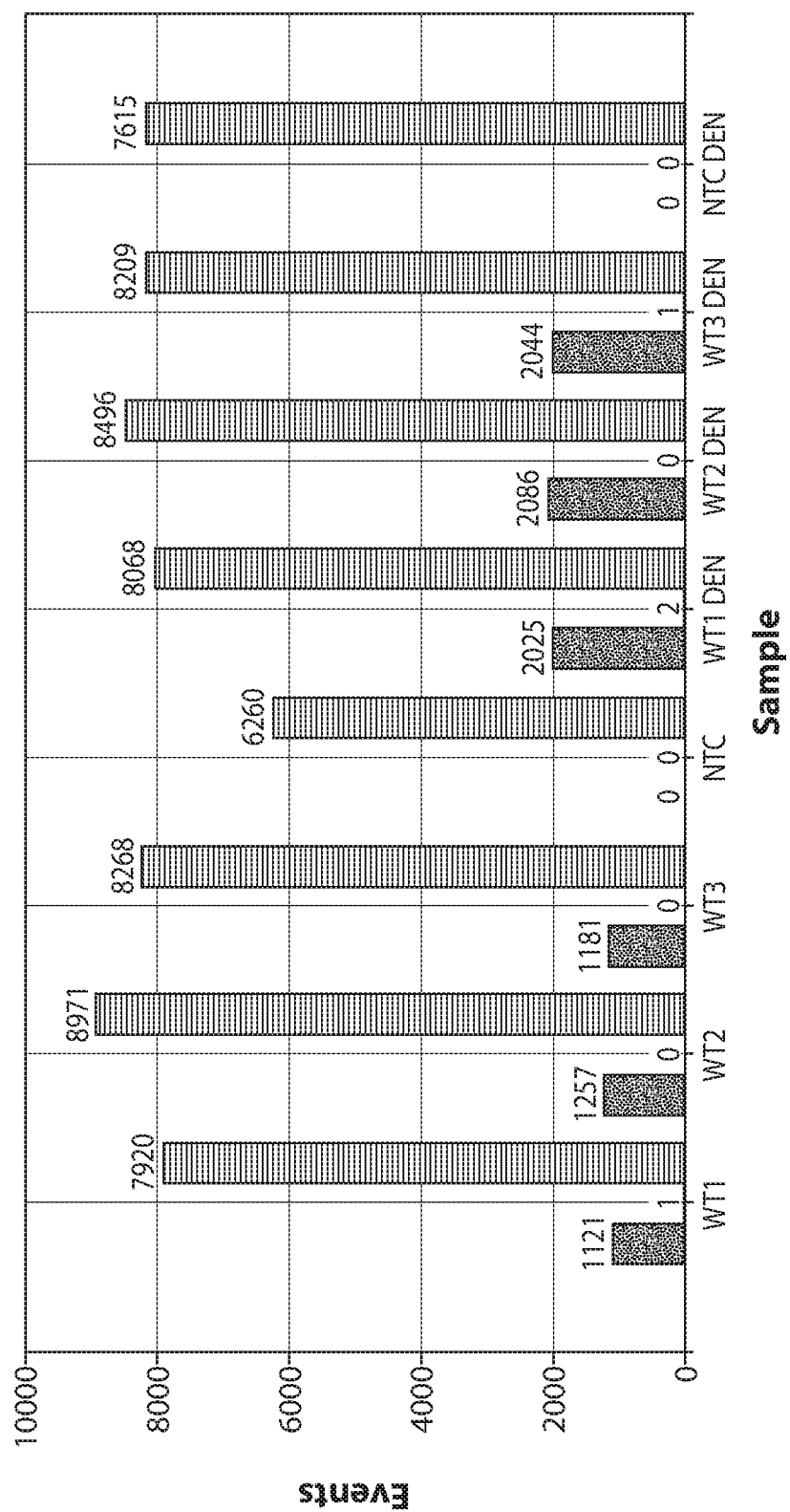
Figure 1C:
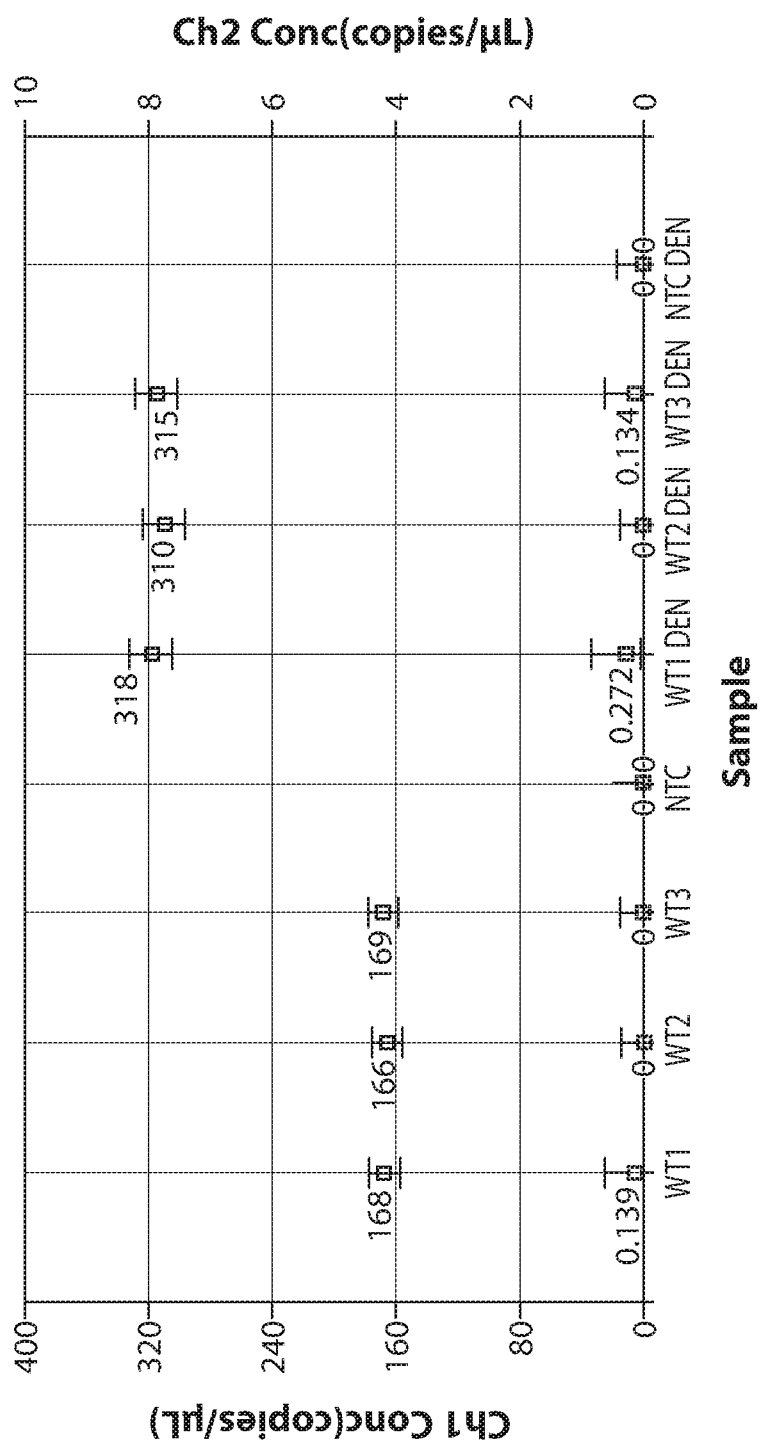

As of its inception, digital PCR places a single double stranded DNA molecule in a separate amplification reaction (FIGS. 1A-1C) by compartmentalizing the sample. For example, in digital droplet PCR (ddPCR) the amplification reaction is compartmentalized into microscopic emulsion-based droplets containing one or zero double stranded DNA molecules per droplet. The number of droplets that contain one double stranded molecule is directly related to the amount of DNA contained in the original clinical sample (e.g., the nanograms of DNA input). For example, if 6 ng of DNA input is obtained from circulating DNA, this corresponds to about 1000 copies of the diploid genome, hence one expects about 1000 droplets to PCR amplify DNA and produce signal during ddPCR. The number of positive droplets is important as it directly defines the lowest number of mutations that can be detected (in this case being 0.1% or 1 in 1000). The present invention applies DNA denaturation immediately prior to droplet generation, thereby doubling the number of DNA target molecules that are present in droplets. In the same example, following denaturation and droplet generation one obtains 2000 positive droplets and the limit of detection becomes 0.05% or 1 in 2000.

Doubling the Targets that can be Detected Via ddPCR.

As an alternative, one can split the original sample of 6 ng in two equal halves (3 ng each), and then apply DNA denaturation to each half, thereby obtaining 6000 single stranded molecules from each. If these denatured samples are used as input in droplets, one obtains 6000 positive droplets from each of the two halves, thereby doubling the number of assays that can be performed. For example, one may use the first half of the sample to examine BRAF mutations at a limit of 1 mutant in 1000 alleles, which is equivalent to using the original, non-denatured sample in a conventional ddPCR approach; and also, use the second half of the sample to examine KRAS mutations. The doubling of the information comes at almost no additional cost or effort as compared to the existing process.

Application to Next Generation Sequencing or Other DNA Testing Platforms.

Figure 2:
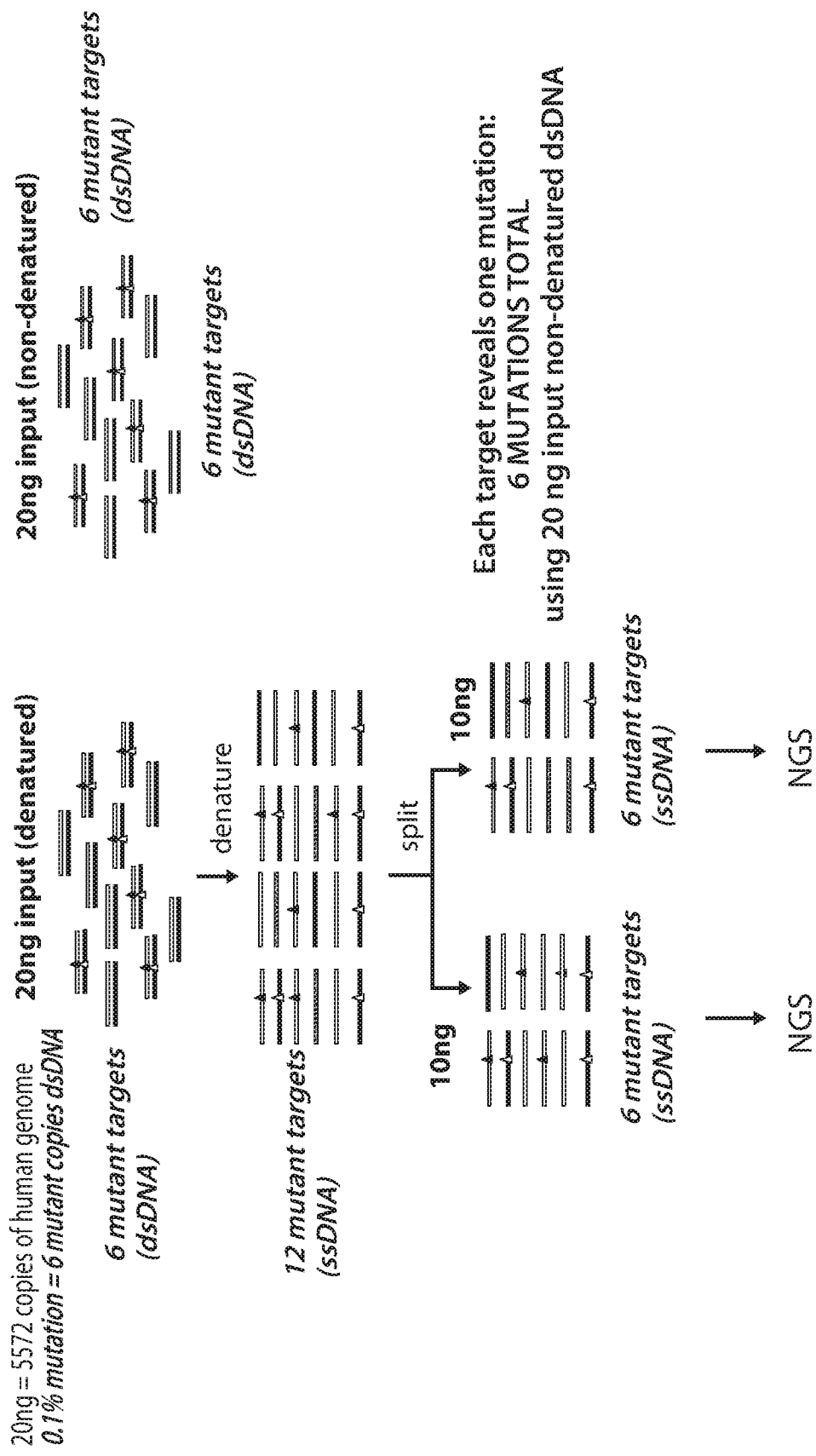
FIG. 2 illustrates the effect of denaturing nucleic acid prior to target detection compared to when the same amount of dsDNA is inputted without denaturation. As shown, denaturation doubles the number of molecules that can supply the information. In the right column, each target reveals one mutation and there are six mutations total using 20 ng input non-denatured dsDNA. 20 ng=5572 copies of the human genome; 0.1% mutation=6 mutant copies of dsDNA.
Figure 3:
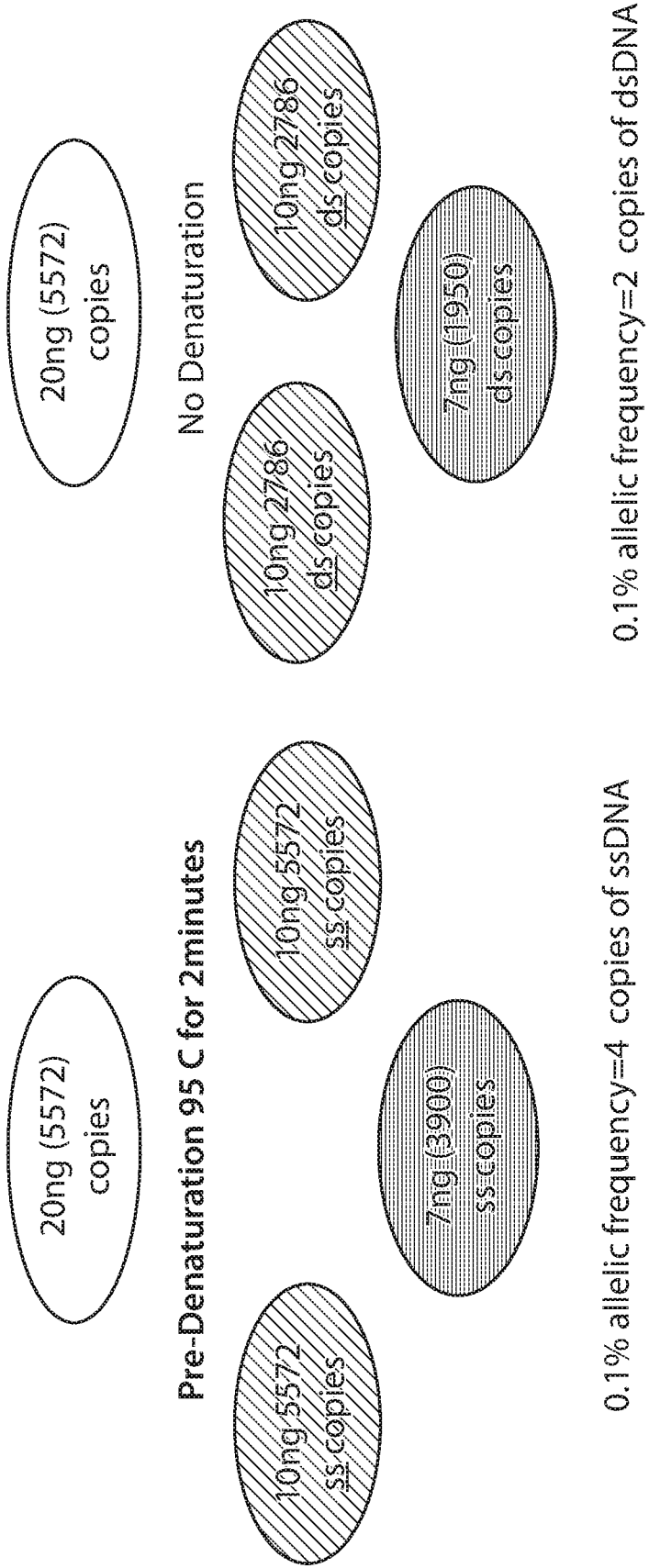
FIG. 3 illustrates that DNA denaturation increases the chances of detecting the mutation when sample has low mutation copies. With 7 ng 0.1% has 2× increased chances of being detected following PCR. 0.1% allelic frequency=four copies of ssDNA (left); 0.1% allelic frequency=two copies of dsDNA (right).

The concept described above can also be applied to any other mutation detection strategy to enable doubling of the information obtained from limited DNA samples. For example, the starting DNA amount is always directly related to the lowest mutation level that can be detected in a circulating DNA sample. If an assay currently requires a minimum of 20 ng of starting double-stranded DNA for mutation detection, by applying the described denaturation procedure one may use 10 ng of denatured DNA and obtain equivalent results as 20 ng of non-denatured DNA (FIG. 2; FIG. 3). FIGS. 4, 5, 6, and 7 illustrate methods of denaturing a sample of double-stranded nucleic acid and using portions of the denatured nucleic acid to perform separate tom and bottom strand analyses.

Convenient Methods for Denaturation

These include thermal denaturation; pH-based denaturation via NaOH; organic buffers such as formamide, DMSO and others; enzymes like helicases that denature the DNA.

Therefore, the presently disclosed concept is a simple change in practice that can be used in conjunction with PCR (e.g., digital PCR), next generation sequencing, or other types of mutation testing. Accordingly, disclosed herein are products and kits that contain simple reagents that generate DNA denaturation at room temperature prior to generating digital PCR droplets or prior to sample preparation for other mutation testing technologies.

REFERENCES FOR EXAMPLE 1

[1] Diehl F, Schmidt K, Choti M A, Romans K, Goodman S, Li M, Thornton K, Agrawal N, Sokoll L, Szabo S A, Kinzler K W, Vogelstein B, Diaz L A, Jr.: Circulating mutant DNA to assess tumor dynamics. Nature medicine 2008, 14:985-90.

[2] Thierry A R, Mouliere F, El Messaoudi S, Mollevi C, Lopez-Crapez E, Rolet F, Gillet B, Gongora C, Dechelotte P, Robert B, Del Rio M, Lamy P J, Bibeau F, Nouaille M, Loriot V, Jarrousse A S, Molina F, Mathonnet M, Pezet D, Ychou M: Clinical validation of the detection of KRAS and BRAF mutations from circulating tumor DNA. Nature medicine 2014, 20:430-5.

[3] Newman A M, Bratman S V, To J, Wynne J F, Eclov N C, Modlin L A, Liu C L, Neal J W, Wakelee H A, Merritt R E, Shrager J B, Loo B W, Jr., Alizadeh A A, Diehn M: An ultrasensitive method for quantitating circulating tumor DNA with broad patient coverage. Nature medicine 2014, 20:548-54.

[4] Bettegowda C, Sausen M, Leary R J, Kinde I, Wang Y, Agrawal N, Bartlett B R, Wang H, Luber B, Alani R M, Antonarakis E S, Azad N S, Bardelli A, Brem H, Cameron J L, Lee C C, Fecher L A, Gallia G L, Gibbs P, Le D, Giuntoli R L, Goggins M, Hogarty M D, Holdhoff M, Hong S M, Jiao Y, Juhl H H, Kim J J, Siravegna G, Laheru D A, Lauricella C, Lim M, Lipson E J, Marie S K, Netto G J, Oliner K S, Olivi A, Olsson L, Riggins G J, Sartore-Bianchi A, Schmidt K, Shih 1 M, Oba-Shinjo S M, Siena S, Theodorescu D, Tie J, Harkins T T, Veronese S, Wang T L, Weingart J D, Wolfgang C L, Wood L D, Xing D, Hruban R H, Wu J, Allen P J, Schmidt C M, Choti M A, Velculescu V E, Kinzler K W, Vogelstein B, Papadopoulos N, Diaz L A, Jr.: Detection of circulating tumor DNA in early- and late-stage human malignancies. Sci Transl Med 2014, 6:224ra24.

[5] Diehl F, Li M, Dressman D, He Y, Shen D, Szabo S, Diaz L A, Jr., Goodman S N, David K A, Juhl H, Kinzler K W, Vogelstein B: Detection and quantification of mutations in the plasma of patients with colorectal tumors. Proc Natl Acad Sci USA 2005, 102:16368-73.

[6] Schwaederle M, Husain H, Fanta P T, Piccioni D E, Kesari S, Schwab R B, Patel S P, Harismendy O, Ikeda M, Parker B A, Kurzrock R: Use of Liquid Biopsies in Clinical Oncology: Pilot Experience in 168 Patients. Clinical cancer research: an official journal of the American Association for Cancer Research 2016, 22:5497-505.

[7] Roschewski M, Dunleavy K, Pittaluga S, Moorhead M, Pepin F, Kong K, Shovlin M, Jaffe E S, Staudt L M, Lai C, Steinberg S M, Chen C C, Zheng J, Willis T D, Faham M, Wilson W H: Circulating tumour DNA and CT monitoring in patients with untreated diffuse large B-cell lymphoma: a correlative biomarker study. The Lancet Oncology 2015, 16:541-9.

[8] Milbury C A, Li J, Makrigiorgos G M: PCR-based methods for the enrichment of minority alleles and mutations. Clin Chem 2009, 55:632-40.

[9] Newton C R, Graham A, Heptinstall L E, Powell S J, Summers C, Kalsheker N, Smith J C, Markham A F: Analysis of any point mutation in DNA. The amplification refractory mutation system (ARMS). Nucleic acids research 1989, 17:2503-16.

[10] Sun X, Hung K, Wu L, Sidransky D, Guo B: Detection of tumor mutations in the presence of excess amounts of normal DNA. Nat Biotechnol 2002, 20:186-9.

[11] Li J, Wang L, Mamon H, Kulke M H, Berbeco R, Makrigiorgos G M: Replacing PCR with COLD-PCR enriches variant DNA sequences and redefines the sensitivity of genetic testing. Nature medicine 2008, 14:579-84.

[12] Wu L R, Wang J S, Fang J Z, Evans E R, Pinto A, Pekker I, Boykin R, Ngouenet C, Webster P J, Beechem J, Zhang D Y: Continuously tunable nucleic acid hybridization probes. Nat Methods 2015, 12:1191-6.

[13] Guha M, Castellanos-Rizaldos E, Liu P, Mamon H, Makrigiorgos G M: Differential strand separation at critical temperature: a minimally disruptive enrichment method for low-abundance unknown DNA mutations. Nucleic acids research 2013, 41:e50.

[14] Milbury C A, Li J, Makrigiorgos G M: Ice-COLD-PCR enables rapid amplification and robust enrichment for low-abundance unknown DNA mutations. Nucleic acids research 2011, 39:e2.

[15] How Kit A, Mazaleyrat N, Daunay A, Nielsen H M, Terris B, Tost J: Sensitive detection of KRAS mutations using enhanced-ice-COLD-PCR mutation enrichment and direct sequence identification. Human mutation 2013, 34:1568-80.
[16] Galbiati S, Brisci A, Lalatta F, Seia M, Makrigiorgos G M, Ferrari M, Cremonesi L: Full COLD-PCR protocol for noninvasive prenatal diagnosis of genetic diseases. Clin Chem 2011, 57:136-8.
[17] Li J, Milbury C A, Li C, Makrigiorgos G M: Two-round coamplification at lower denaturation temperature-PCR (COLD-PCR)-based sanger sequencing identifies a novel spectrum of low-level mutations in lung adenocarcinoma. Human mutation 2009, 30:1583-90.
[18] Li J, Berbeco R, Distel R J, Janne P A, Wang L, Makrigiorgos G M: s-RT-MELT for rapid mutation scanning using enzymatic selection and real time DNA-melting: new potential for multiplex genetic analysis. Nucleic acids research 2007, 35:e84.
[19] Murphy D M, Bejar R, Stevenson K, Neuberg D, Shi Y, Cubrich C, Richardson K, Eastlake P, Garcia-Manero G, Kantarjian H, Ebert B L, Mike Makrigiorgos G: NRAS mutations with low allele burden have independent prognostic significance for patients with lower risk myelodysplastic syndromes. Leukemia 2013, 27:2077-81.
[20] Castellanos-Rizaldos E, Richardson K, Lin R, Wu G, Makrigiorgos M G: Single-tube, highly parallel mutation enrichment in cancer gene panels by use of temperature-tolerant COLD-PCR. Clin Chem 2015, 61:267-77.
[21] Mauger F, Daunay A, Deleuze J F, Tost J, How-Kit A: Multiplexing of E-ice-COLD-PCR Assays for Mutation Detection and Identification. Clin Chem 2016, 62:1155-8.

Example 2

Figure 8:
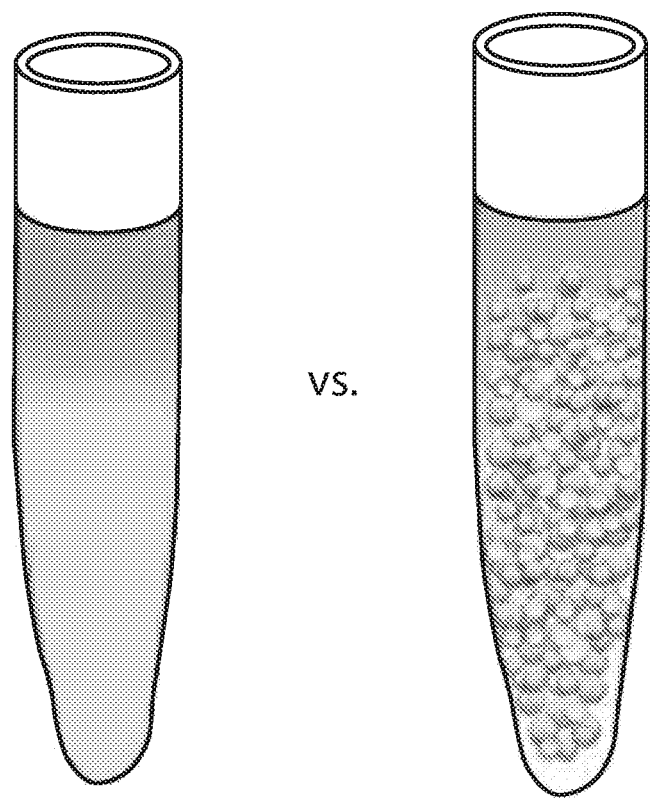
FIG. 8 shows a comparison of traditional PCR (left), which is characterized by one fluorescence measurement and digital PCR (right), which is characterized by partitioning of a PCR reaction mixture into thousands of distinct compartments and making fluorescence measurements on each compartment.

Ability to accurately and efficiently detect rare mutations is valuable and can be used to determine course of therapy and monitor efficacy of therapy over time. Known rare mutations can be identified in cfDNA via liquid biopsy using advanced PCR methods such as digital PCR (dPCR) and digital droplet (ddPCR) methods. In standard PCR, one reaction is carried out per single sample whereas for digital PCR the sample is separated into a large number of partitions, or compartments, and the reaction is carried out in each partition individually (see FIG. 8). This separation allows for a more reliable collection and more sensitive measurement of nucleic acid amounts.

Despite advances over regular PCR, diagnostic results are often comprised in digital PCR. For example, limited amount of cfDNA can be obtained from a blood draw, excess amount of WT DNA in the sample limits the amount/accuracy of information, testing for multiple targets requires larger amounts of cfDNA, and amplifying original sample via PCR introduces errors.

A simple and effective method to double the information obtained from a DNA sample is provided herein. DNA contains redundant information on both strands i.e. any mutation is on both strands. Therefore both strands aren't needed to detect mutations. Separating the two strands via denaturation, doubles the DNA sample and can provide information for more than one target. This allows more assays to be performed from a small sample without introducing errors.

In real life random fragmentation of DNA occurs. Top strand ends up shorter than the lower strand. During sequencing, a repair enzyme is often used to fix this. Adding this repair enzyme before denaturing the DNA mends the strands making them blunt ended. This 2-step process increases the data points after digital PCR.

Example 3. Denaturation-Enhanced Digital Droplet PCR for Liquid Biopsies

The following demonstrates that by applying complete denaturation of double-stranded nucleic acid to form single-stranded nucleic acid prior to partitioning (e.g., by droplet formation in ddPCR) of the nucleic acid sample, the number of positive partitions (e.g., droplets) increase. Denaturation-enhanced dPCR (e.g., denaturation-enhanced ddPCR (dddPCR)) was applied using circulating-DNA from volunteers and cancer patients for commonly-used mutations. dddPCR using genomic-DNA results in a 1.9-2-fold-increase in data-positive droplets, while dddPCR applied on highly-fragmented circulating-DNA results to 1.6-1.7-fold increase. Moreover, end-repair of circulating-DNA before denaturation enables circulating-DNA to display 1.9-2-fold increase in data-positive signals, like genomic-DNA. The data indicate that doubling of data-positive droplets from a given DNA input doubles the number of potential ddPCR assays and improves ddPCR accuracy for cfDNA mutation-detection.

This simple and fundamental modification in ddPCR enables extraction of more information from low-input clinical samples with minor change in protocols, and is applicable to all ddPCR platforms for mutation detection and, potentially, for gene copy-number analysis in cancer and prenatal-screening.

Figure 9A:
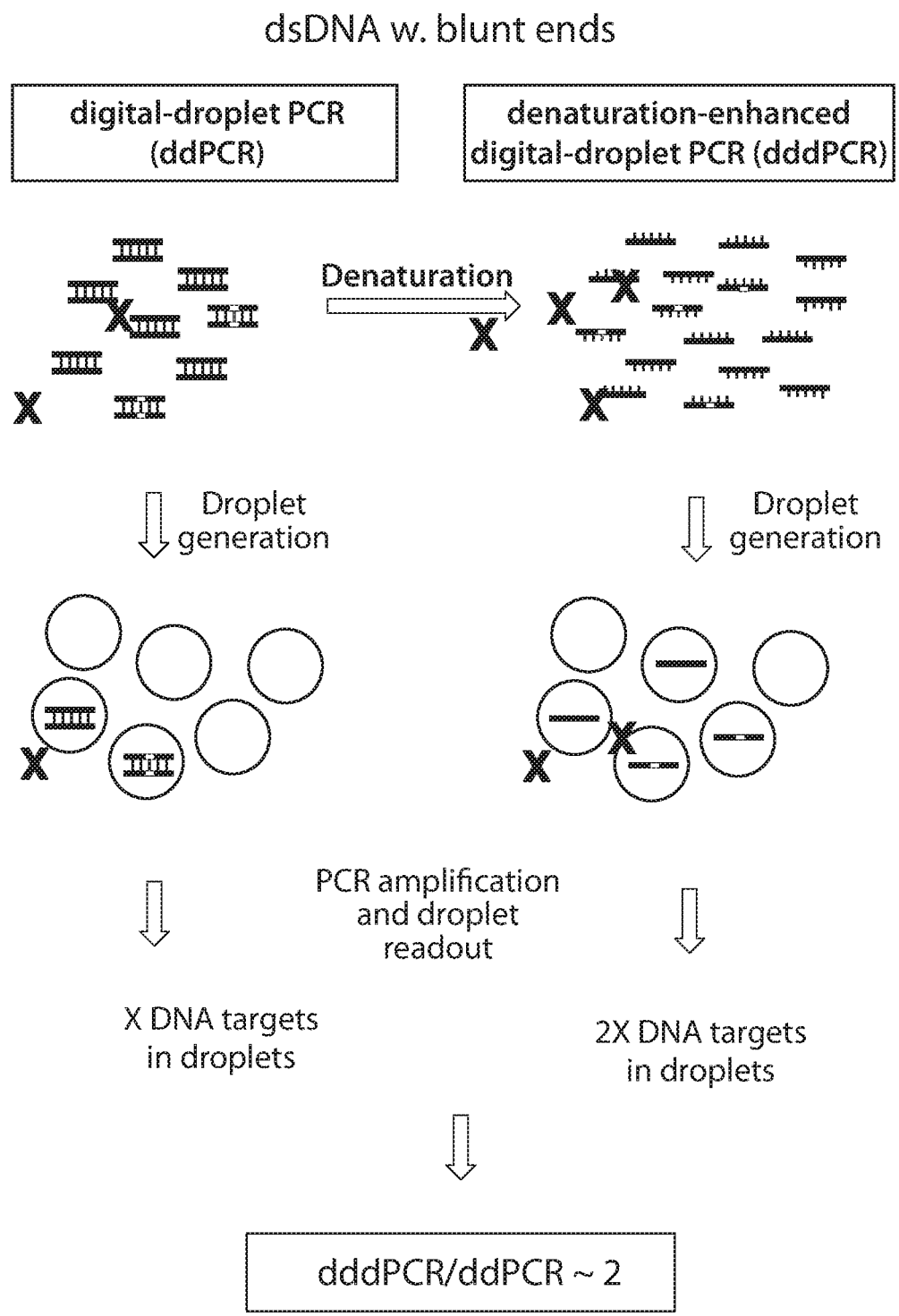
FIGS. 9A-9B illustrate a concept and workflow of denaturation-enhanced digital-droplet PCR (dddPCR) as compared to standard ddPCR.
Figure 9B:
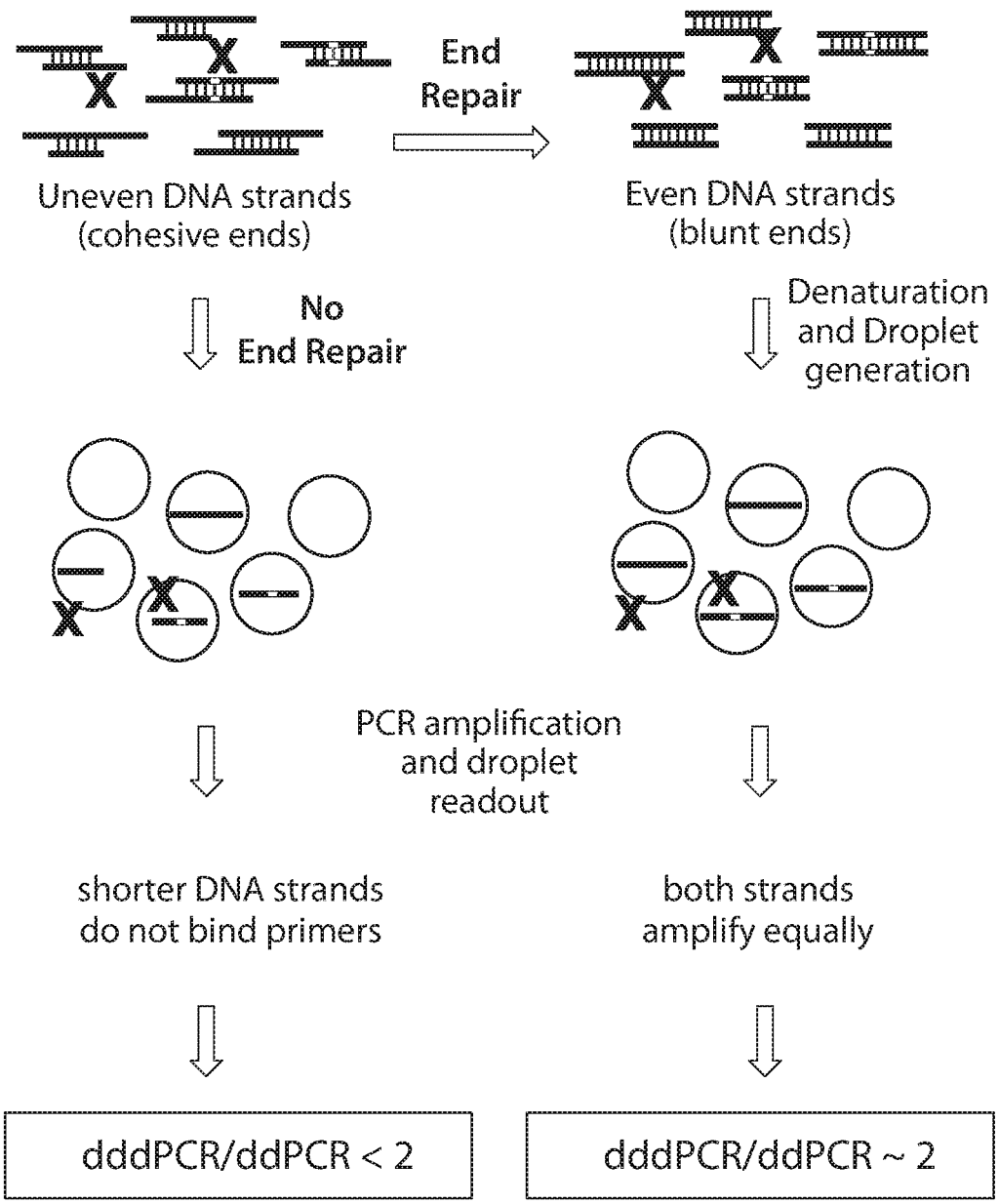

Indeed, amplification using just a sense or anti-sense DNA strand in a droplet is likely to produce the same number of positive droplets as the corresponding double stranded molecule, provided the two strands are of equal size to begin with (blunt-ended DNA, FIG. 9A). If, on the other hand, DNA is randomly fragmented with unequal strands, e.g., as in circulating DNA, then placing each strand in a separate droplet may not double the ddPCR signal, since the shorter strand may not bind the primers. It is demonstrated that a DNA end-repair step performed just prior to denaturation and droplet formation restores the ability to double the ddPCR signal, FIG. 9B. This simple and fundamental modification, denaturation-enhanced digital droplet PCR (dddPCR), enables extraction of more information from small input clinical samples without substantial change in existing digital PCR protocols.

Materials and Methods

Genomic DNA and Circulating Cell-Free DNA Samples

Genomic DNA from cell-line MDA-MB-435S (HTB-129D, ATCC) and the Tru-Q1 Reference Standard (HD728, Horizon Discovery) were used as mutated DNA controls for BRAF p.V600E and NRAS p.Q61K. Human male genomic DNA (G1471, Promega) was employed as a WT control and mixed with mutant DNA to create serially diluted samples. Genomic DNA was digested prior to ddPCR reactions, using 10 units of HindIII-HF restriction enzyme (New England Biolabs) per 1 μg of gDNA according with manufacturer's instructions, with 15 minutes incubation at 37° C.

Plasma and serum samples from cancer patients and normal volunteers were obtained from Massachusetts General Hospital, Dana Farber Cancer Institute and Brigham and Women's Hospital under consent and Institutional Review Boards approval. Cell-free circulating DNA (cfDNA) was isolated from plasma and serum using the QIAamp MinElute Mini Kit or QIAamp Circulating Nucleic Acids Kit (Qiagen), and cfDNA was quantified on a Qubit 3.0 fluorometer using a dsDNA HS assay kit (Thermo Fisher Scientific).

Denaturation-Enhanced Digital-Droplet PCR (dddPCR)

(a) dddPCR without DNA End-Repair

A QX100 Droplet Digital PCR System (Bio-Rad) was used for detection of BRAF p.V600E, BRAF p.V600K, NRAS p.Q61K and EGFR p.L858R mutations. Primers and probe sequences are described elsewhere (12, 26, 31). The amplicon sizes were 78-111 bp for all assays. For each reaction, 1× ddPCR Supermix for probes (Bio-Rad) was mixed with 1 µM forward and reverse primers, 250 nM 6-FAM and HEX or VIC hydrolysis probes (IDT Technologies), and DNA template (5 to 30 ng input) to a final volume of 20 µL. The samples containing the reaction components and DNA already mixed were placed in a Mastercycler Nexus Thermal Cycler (Eppendorf) for DNA denaturation at 95° C. for 1 minute. The temperature was then reduced to 37° C. and the samples were loaded onto an eight-channel cartridge (Bio-Rad) along with 70 µL of droplet generation oil (Bio-Rad). Following emulsion generation on the QX100 Droplet Generator (Bio-Rad), the samples were transferred to a 96-well PCR plate, heat-sealed with foil, and amplified in a Mastercycler Nexus Thermal Cycler. The thermal cycling conditions comprised initial denaturation and polymerase activation for 10 minutes at 95° C., followed by 50 cycles of 94° C. for 30 s and 56° C. for 1 minute, enzyme deactivation at 98° C. for 10 minutes and infinite hold at 10° C.

Alternatively, to decrease the chance of ssDNA damage by prolonged heating, a modified cycling protocol comprising 2 minutes of pre-activation at 95° C. followed by 3 cycles of PCR, for generating dsDNA before proceeding to full polymerase activation at 95° C. for 10 minutes and 50 cycles of amplification.

Regular ddPCR was performed in parallel for each sample, using the same cycling conditions described above, but omitting DNA denaturation prior to droplet generation. The fluorescence signal for each probe was simultaneously measured by QX100 Droplet Reader (Bio-Rad) and results were analyzed with QuantaSoft™ v.1.3.2.0.

(b) dddPCR with DNA End-Repair for Circulating-DNA

In preliminary experiments, circulating cell-free DNA end-repair to produce blunt ends was performed as follows: cfDNA was treated with 1×NEBNext® Ultra™ II End Prep Enzyme Mix in 1×NEBNext® Ultra™ II End Prep Reaction Buffer (New England Biolabs) in a total of 60 µL reaction. Tris-HCl 10 mM was added to complete the total volume and the samples were incubated at 20° C. for 30 minutes and 65° C. for 30 minutes as recommended by the manufacturer. The end-repaired cfDNA was purified with the QIAquick PCR Purification Kit (Qiagen) and then 1 to 10 ng of purified end-repaired cfDNA was used either for dddPCR or for standard ddPCR reactions as described above.

Subsequently a homogeneous, single-tube protocol was developed. 5 ng of extracted cfDNA was mixed with 10 µL of 2×ddPCR Supermix for probes (Bio-Rad) and 0.5 µL of 20×NEBNext® Ultra™ II End Prep Enzyme Mix was added in a total of 17.9 µL reaction. The mixture was incubated at 20° C. for 30 minutes for end-repair and 65° C. for 30 minutes for enzyme inactivation; then 1 µM forward and reverse primers and 250 nM 6-FAM and HEX or VIC hydrolysis probes (for BRAF p.V600E and EGFR p.L858R) or 1× TaqMan® SNP Genotyping Assay for EGFR rs1050171 (ThermoFisher) were added, completing the final 20 µL volume. The samples were denatured at 95° C. for 1 minute for dddPCR denaturation, cooled down to 37° C. and then proceeded to droplet generation. Thermo-cycling conditions were as described above. Experiments using cfDNA were repeated in independent days, with at least three replicas each time.

Statistical Analysis

Results were reported as copies per µL of reaction, determined by the QuantaSoft™ software (Bio-Rad). Error bars represent the 95% confidence intervals using Poisson distribution. For merged wells, the outer bars represent the standard error of the mean for the replicates and the inner ones are the Poisson error bars. The relative standard error in Table 1 was calculated by dividing the square root of the concentration value by the concentration estimate. The Welch's t-test (2-tailed, unpaired) was applied for comparison between groups of droplets in FIGS. 10A-10B. Statistical analysis was performed with GraphPad Prism7.

Results dddPCR Applied on Genomic DNA (a) Single Target Analysis

Figure 11A:
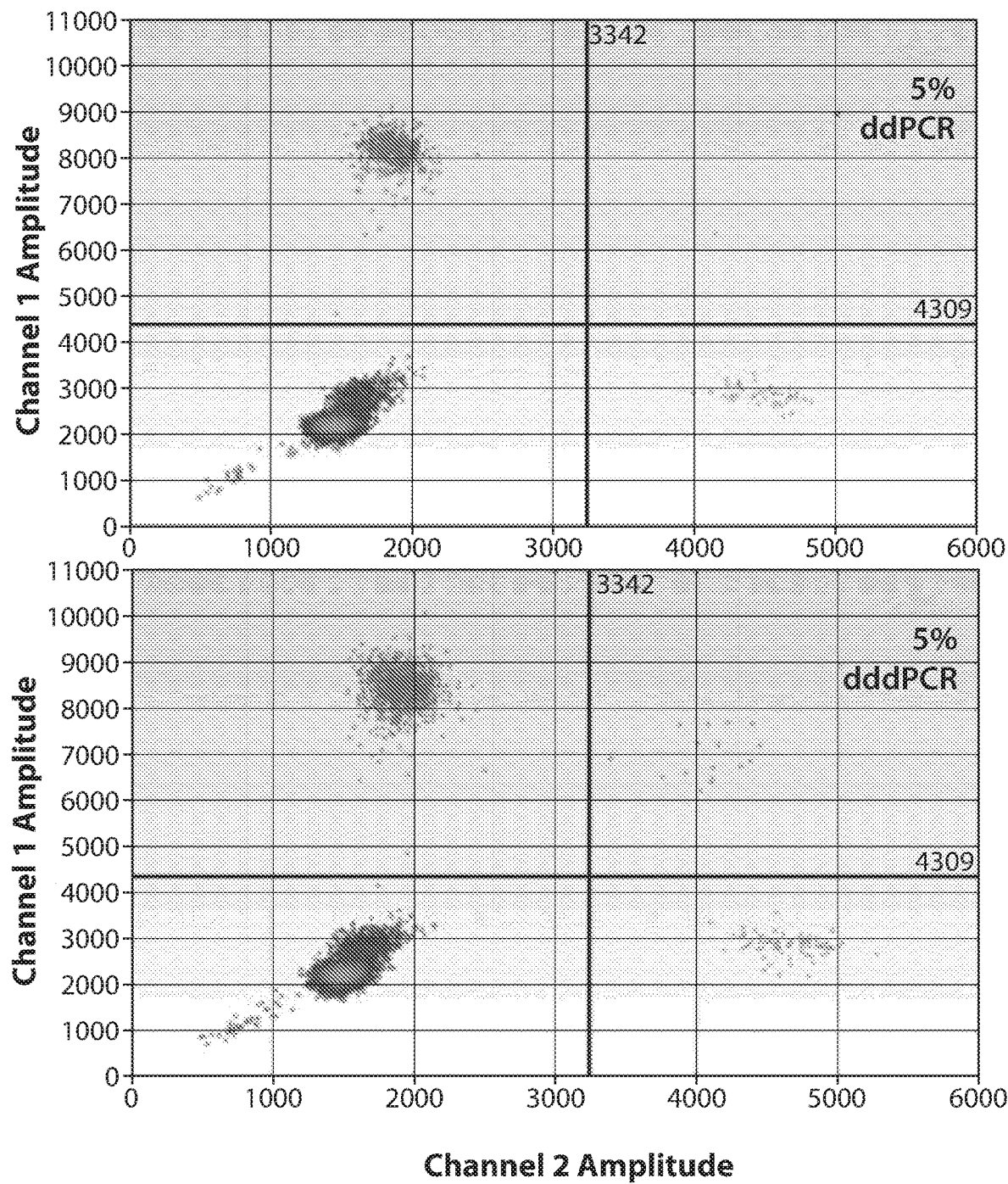
FIGS. 11A-11D show the effect of DNA denaturation prior to droplet formation on wild-type (WT) DNA and 5% mutated gDNA using BRAF p.V600E assay.
Figure 11B:
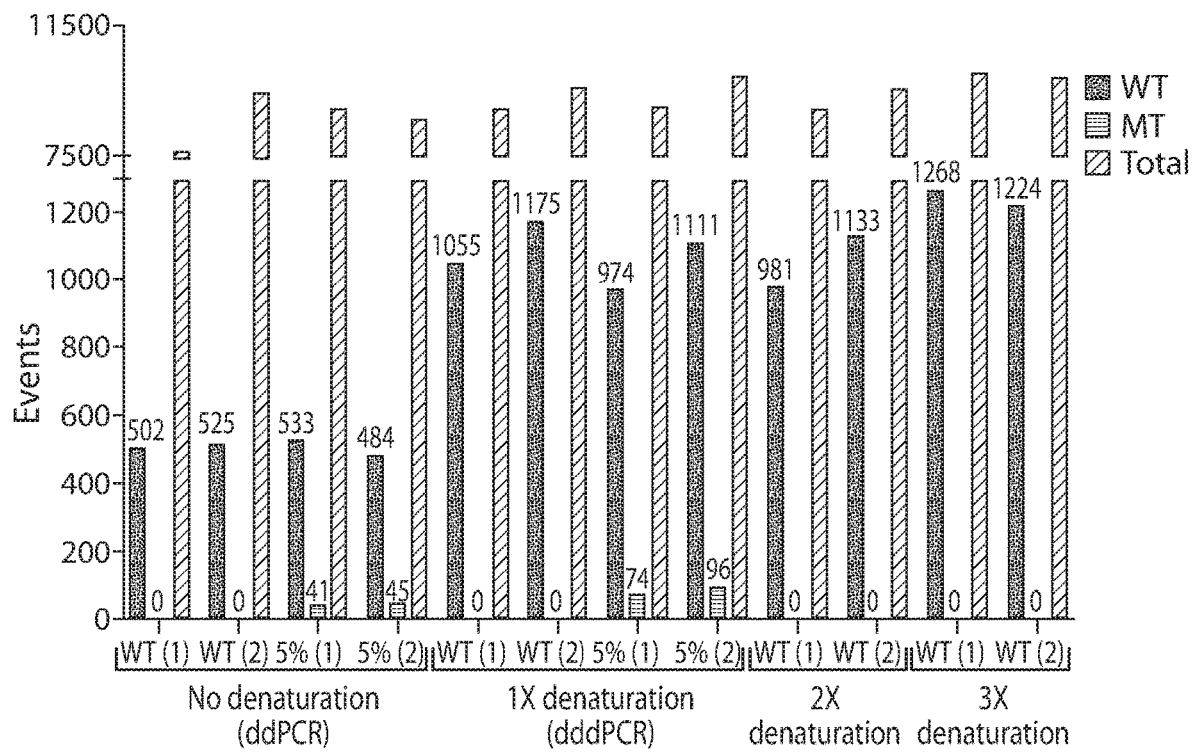
Figure 11C:
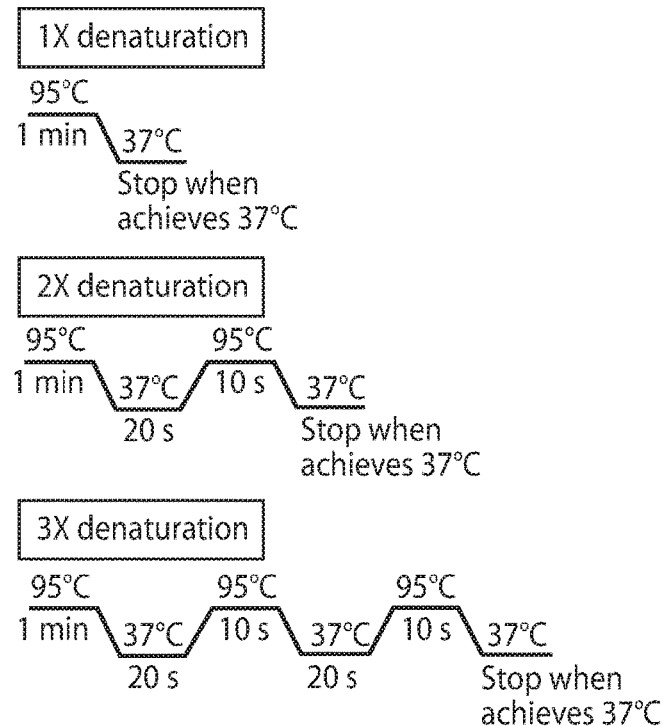
Figure 11D:
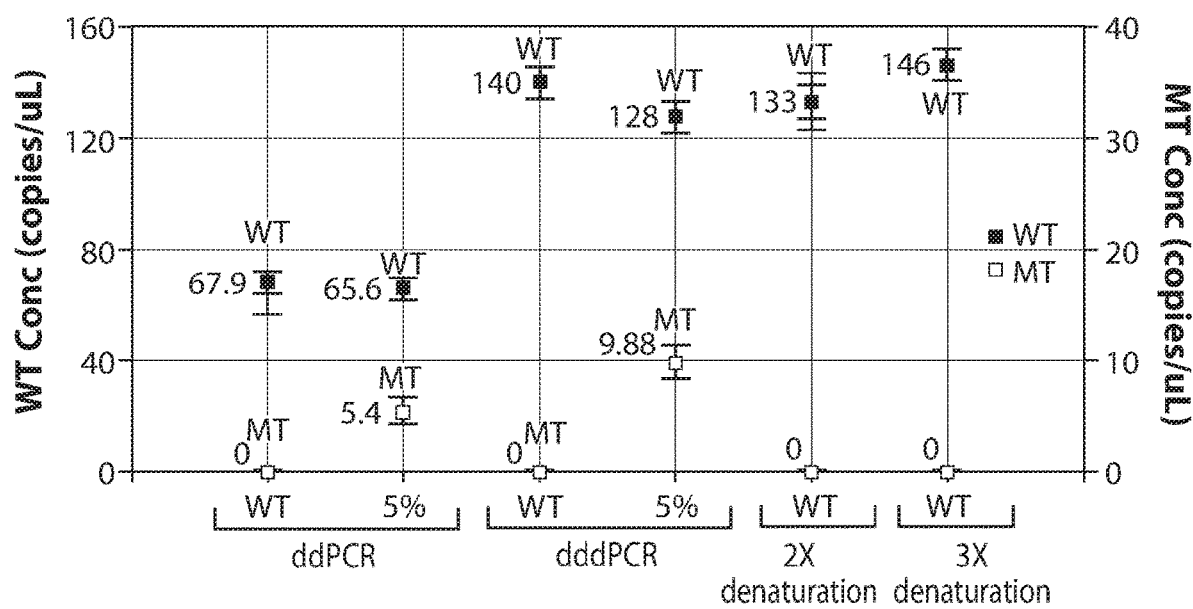

In preliminary experiments, genomic DNA digested with a restriction enzyme, was used to analyze the effect of DNA denaturation prior to droplet formation. dddPCR was employed on 5 ng gDNA containing 5% BRAF p.V600E mutation abundance and using hydrolysis TaqMan probes that distinguish the mutation from WT DNA. Compared with standard ddPCR, no difference in the clustering pattern on the 2D-plots was observed (FIG. 11A) while the number of WT and mutant positive events approximately doubled using dddPCR (FIG. 11B). In control experiments, wild-type samples were also subjected to 2 or 3 consecutive rounds of the denaturation protocol, 1 minute denaturation followed by cooling to 37° C., prior to droplet formation (FIG. 11C). This was done to investigate whether the increase in the positive events is due in part to polymerase synthesis following partial activation of the 'hot-start' polymerase. If polymerase synthesis occurs following the first denaturation step, then additional rounds of denaturation prior to droplet generation would be expected to cause proportional increase in the positive events. However, the number of positive events is similar for 1-3 rounds of denaturation (FIGS. 11B, 11D), indicating that the doubling of data points is related to denaturation and segregation of single-stranded DNA into droplets and not to amplification prior to droplet partitioning.

Figure 12A:
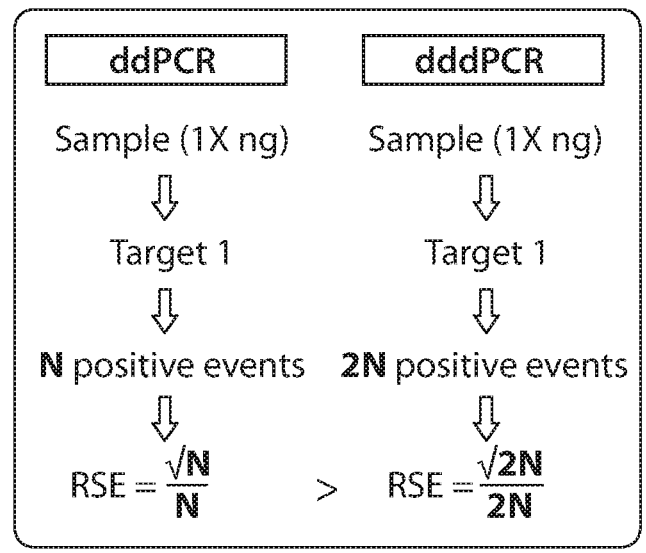
FIGS. 12A-12B show that for a given DNA input, the number of positive events using dddPCR is twice that of ddPCR, thus improving the relative standard error in the analysis.
Figure 12B:
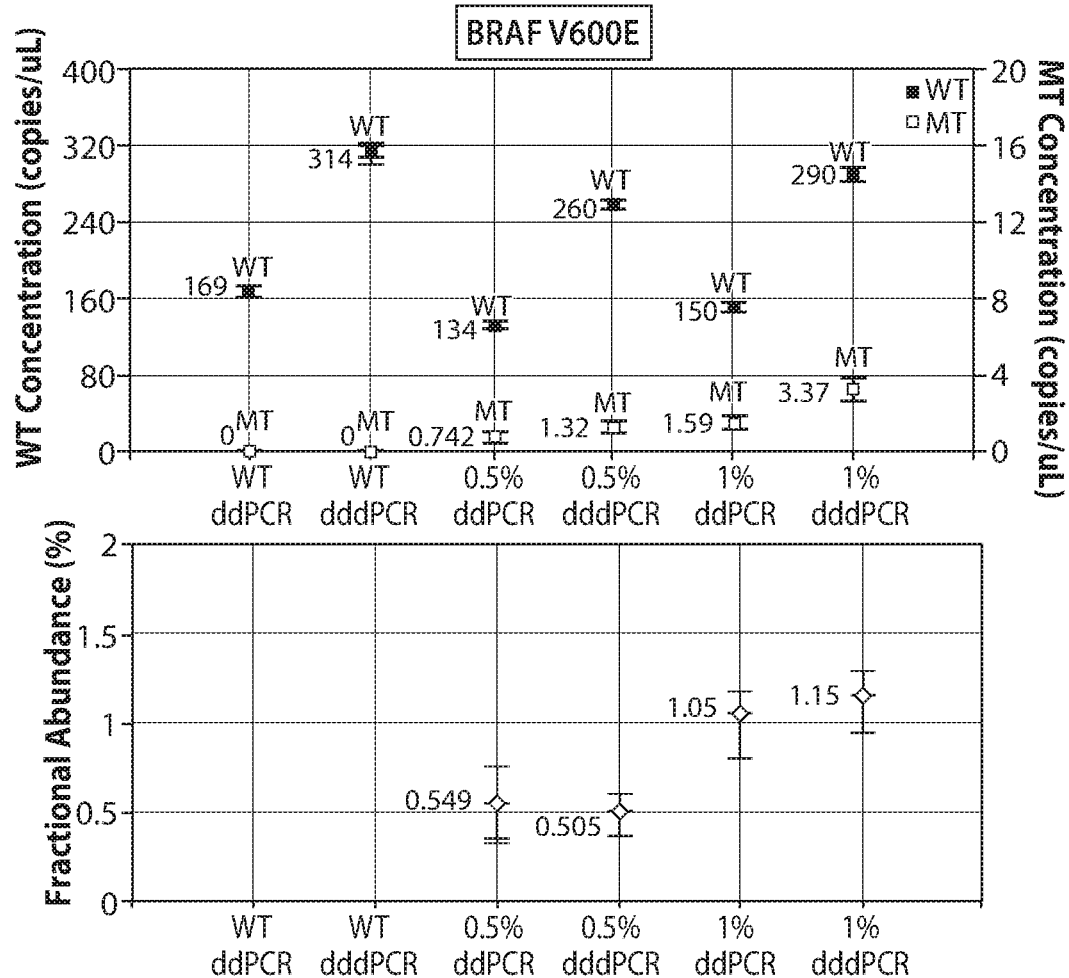
Figure 13:
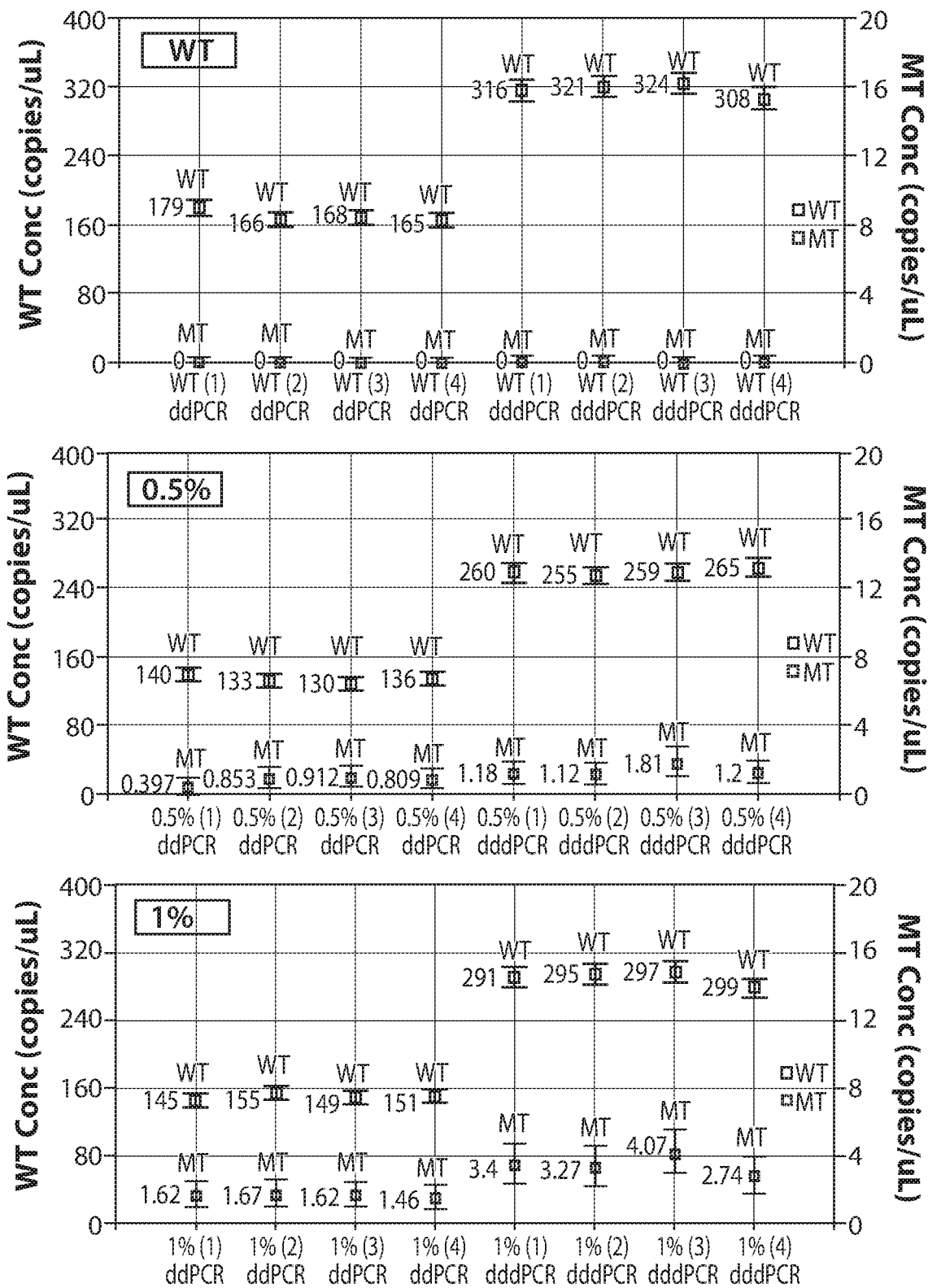
FIG. 13 depicts individual replicas of BRAF V600E analysis using 10 ng of gDNA HTB-19 serially diluted into WT. Merged values are shown in FIGS. 12A-12B.

Next, dddPCR and standard ddPCR were applied to 10 ng of genomic DNA harboring BRAF p.V600E mutation at 1% and 0.5% allele fractions. The samples were run in quadruplicate, following the workflow depicted in FIG. 12A. The number of copies per µL of reaction and the fractional abundance for the merged replicates are shown in FIG. 12B, while the values for individual replicates are shown in FIG. 13. The fold-change of the copies/µL, as calculated by dividing the merged copies/µL, values of dddPCR by the values of ddPCR, ranged from 1.8 to 2.1-fold (Table 1), indicating that DNA was fully denatured prior to droplet formation, in the dddPCR protocol. Moreover, the calculated relative standard error (RSE) of concentration for WT and MT copies was smaller for dddPCR than for standard ddPCR (Table 1), thus improving measurement accuracy.

| | Fold change | Relative Standard Error, RSE | | | |
|---|---|---|---|---|---|
| | (dddPCR/ddPCR) | ddPCR | | dddPCR | |
| Sample | WT MT | WT | MT | WT | MT |
| WT | 1.9 N/A | 0.077 | N/A | 0.056 | N/A |
| MT 0.5% | 1.9 1.8 | 0.086 | 1.161 | 0.062 | 0.870 |
| MT 1% | 1.9 2.1 | 0.082 | 0.793 | 0.059 | 0.545 |

Figure 10A:
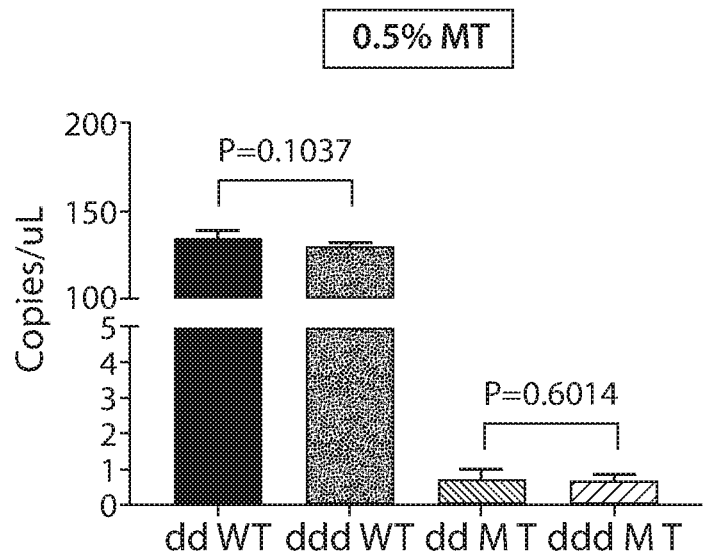
FIGS. 10A-10B show that for absolute quantification of gDNA, the concentration values obtained by dddPCR are divided by 2. There is no significant difference on copies/µL, determination between ddPCR and dddPCR if the dddPCR values are divided by 2.
Figure 10B:
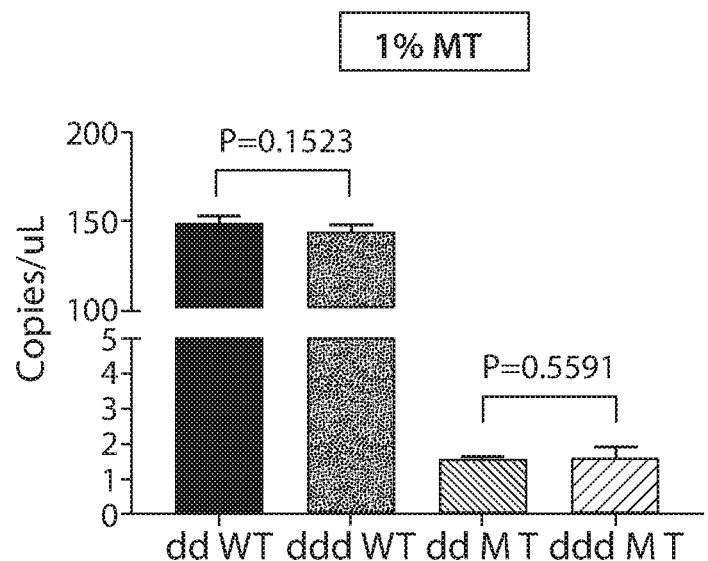

In dddPCR, DNA is denatured and ssDNA molecules are partitioned into droplets. Thus, the measured concentration reflects number of ssDNA copies. Accordingly, to quantify the original genomic DNA input the concentration values were divided by 2. The WT and MT copies/µL values of gDNA samples analyzed by standard ddPCR were compared with the concentration values divided by 2 for samples analyzed by dddPCR. There was no significant difference between the two methods (P>0.05; FIGS. 10A-10B). Thus, if gDNA is fully denatured before droplet generation and the concentration values derived by the current commercial software are divided by 2, the absolute quantification is preserved using dddPCR.

Figure 14A:
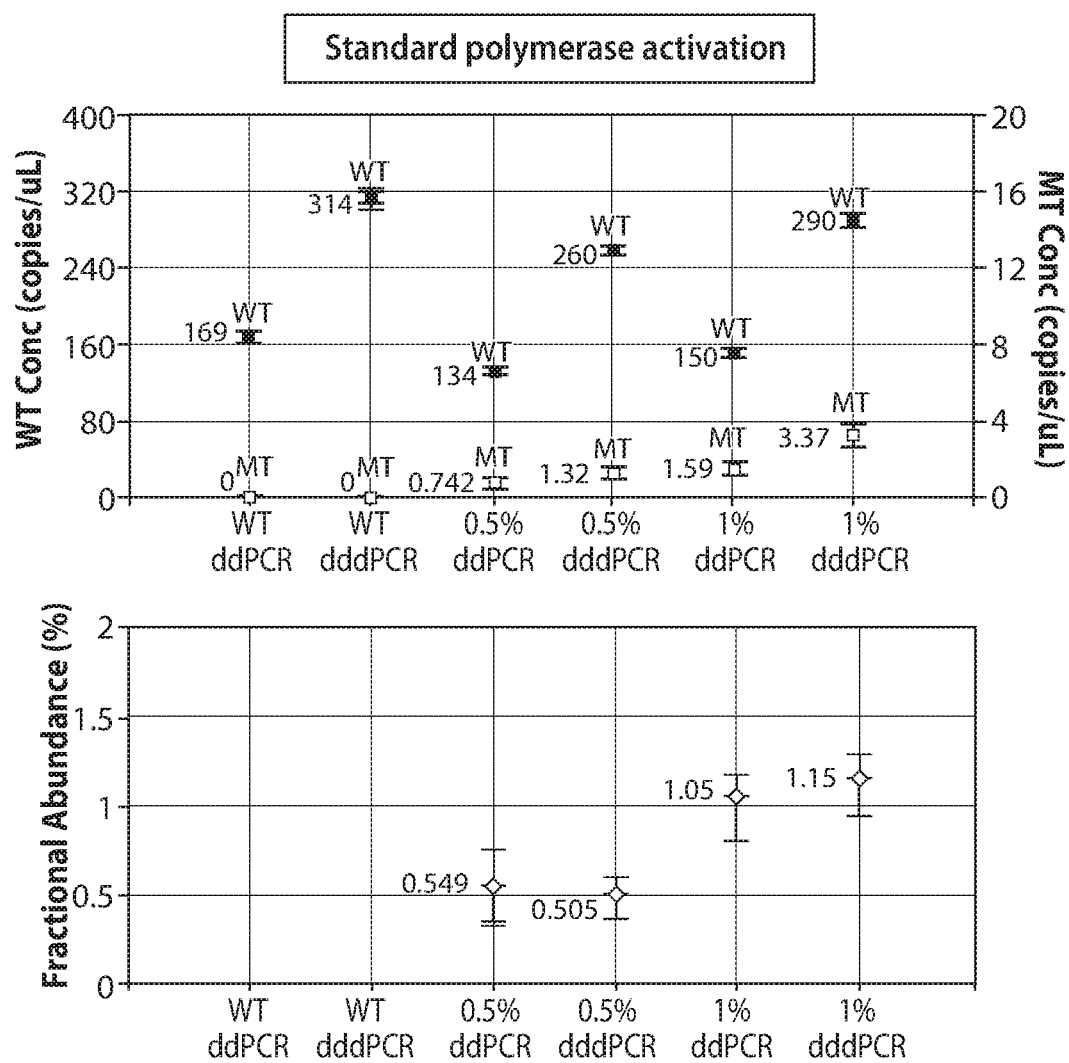
FIGS. 14A-14B show a comparison of cycling programs used for ddPCR and dddPCR of BRAF V600E analysis using 10 ng of mutant gDNA serially diluted into WT, performed with two different cycling programs.
Figure 14B:
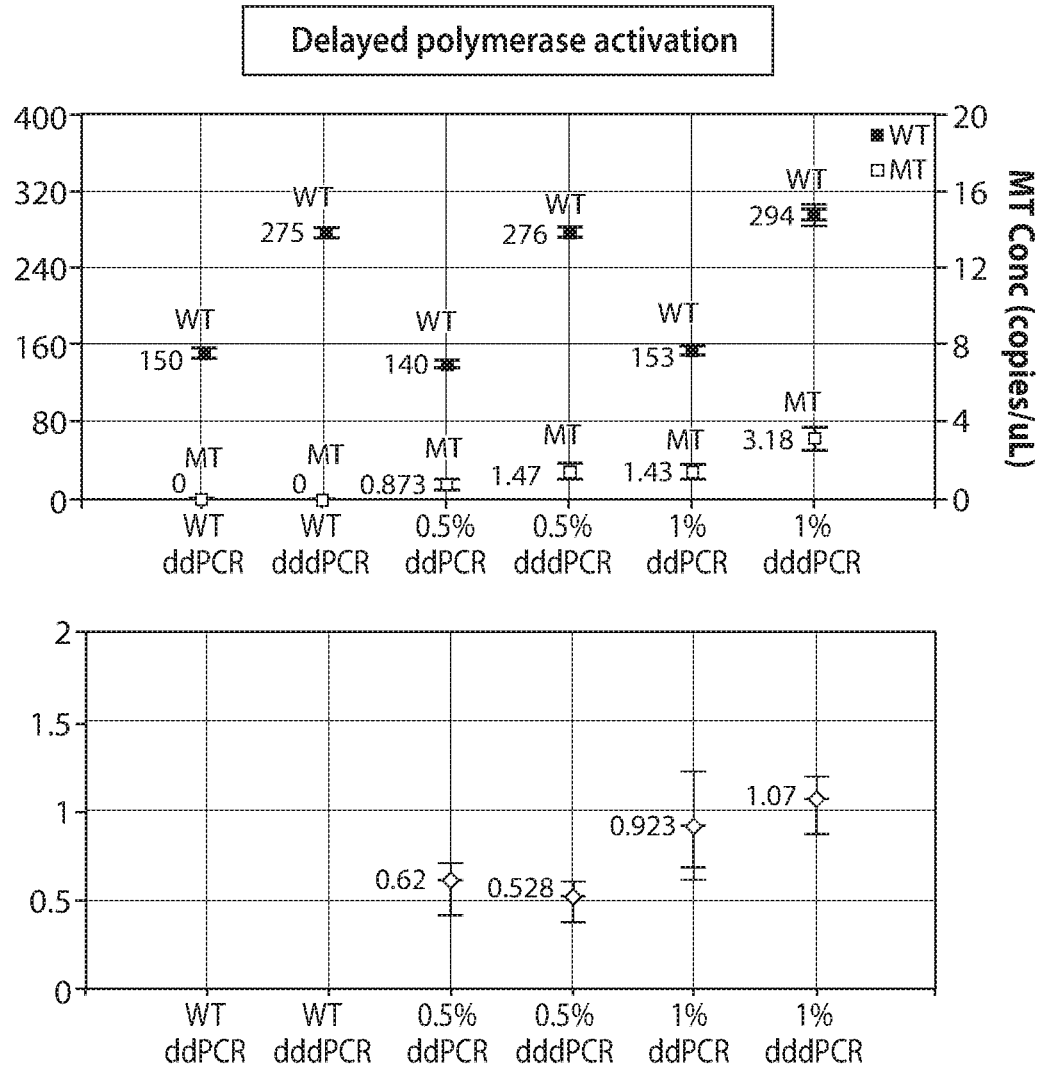

Prolonged exposure of DNA to elevated temperatures, in TE buffer, could lead to DNA damage, introducing bias in ddPCR measurements, although damage is not significant in the commercial ddPCR mastermix (32). As a pre-caution, a modified cycling protocol applied after droplet generation was implemented, which includes 2 minutes polymerase pre-activation at 95° C. followed by 3 cycles of PCR to generate dsDNA before proceeding with the regular protocols of 10 minutes activation at 95° C.and 50 cycles of PCR. This modified protocol was compared side by side with the standard cycling for both ddPCR and dddPCR and the results were found to be equivalent (FIGS. 14A-14B). This modified protocol was adopted for further experiments.

Figures 15A, 15B:
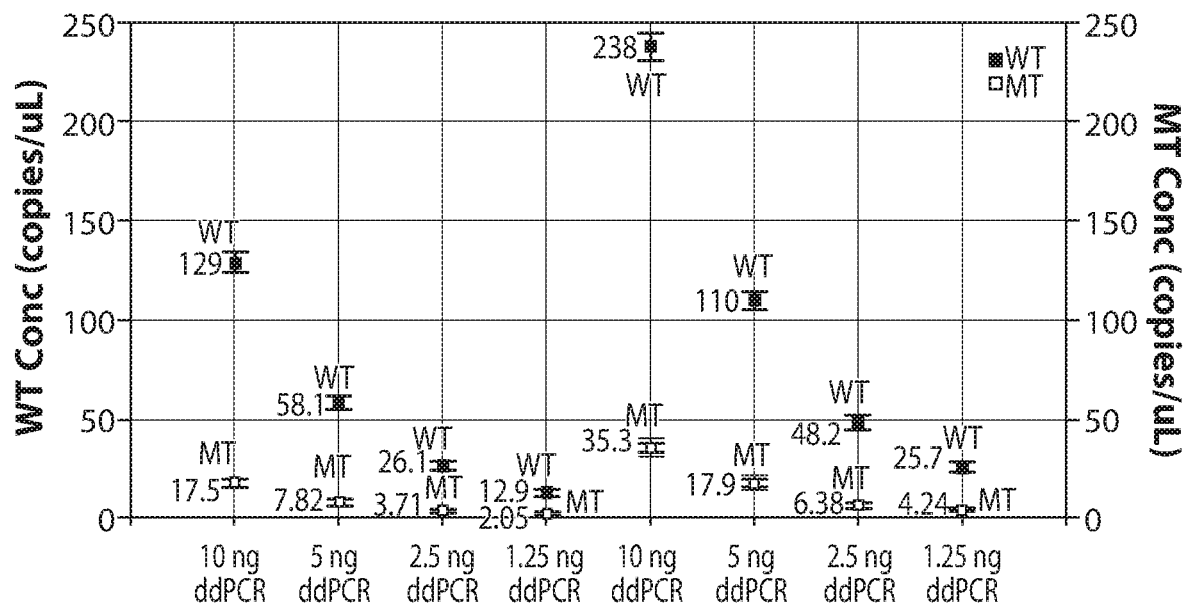
FIGS. 15A-15B show concentration fold-change between dddPCR and standard ddPCR for a gradient of gDNA input.

Next, dddPCR and ddPCR were applied to gDNA containing BRAF p.V600E mutation at 10% allelic fraction at DNA input of 10, 5, 2.5 and 1.25 ng. The fold-change in concentration (copies/µL) as obtained by dividing dddPCR values by ddPCR values was not significantly different across various gDNA input amounts (FIGS. 15A, 15B), indicating that dddPCR can be applied with variable input DNA quantities.

(b) Analysis of Two Targets with Half the Initial Input Each

Figure 16A:
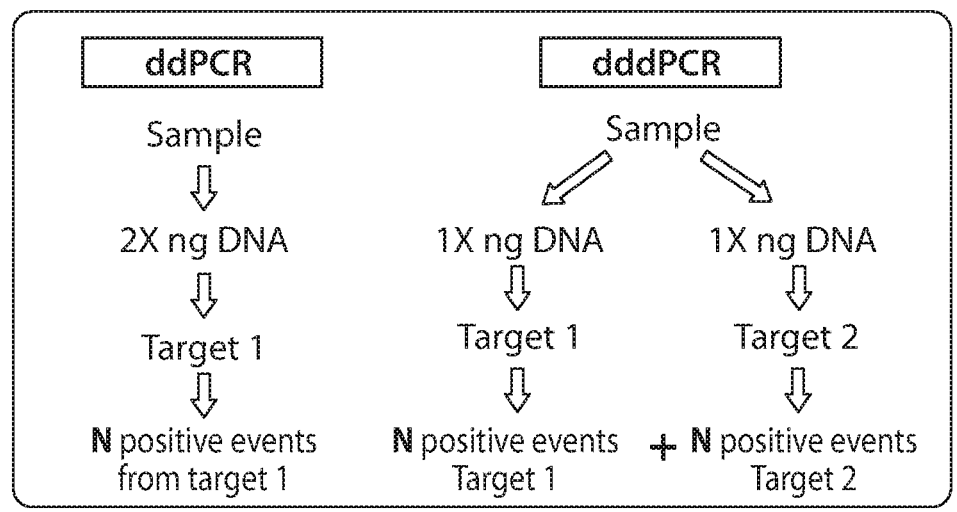
FIGS. 16A-16C illustrate that dddPCR allows the analysis of 2 different targets in independent reactions using the same quantity of DNA used for a single ddPCR reaction and producing similar number of WT and MT copies in each reaction.
Figure 16B:
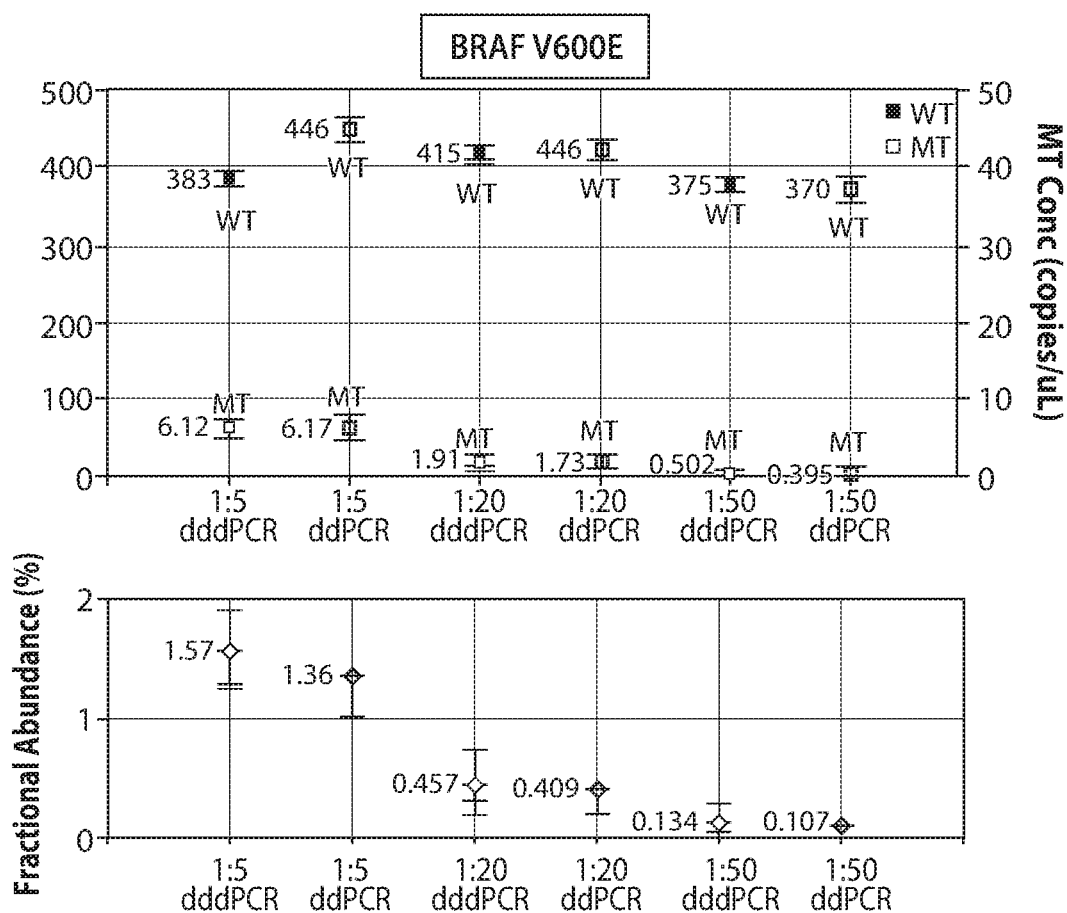
Figure 16C:
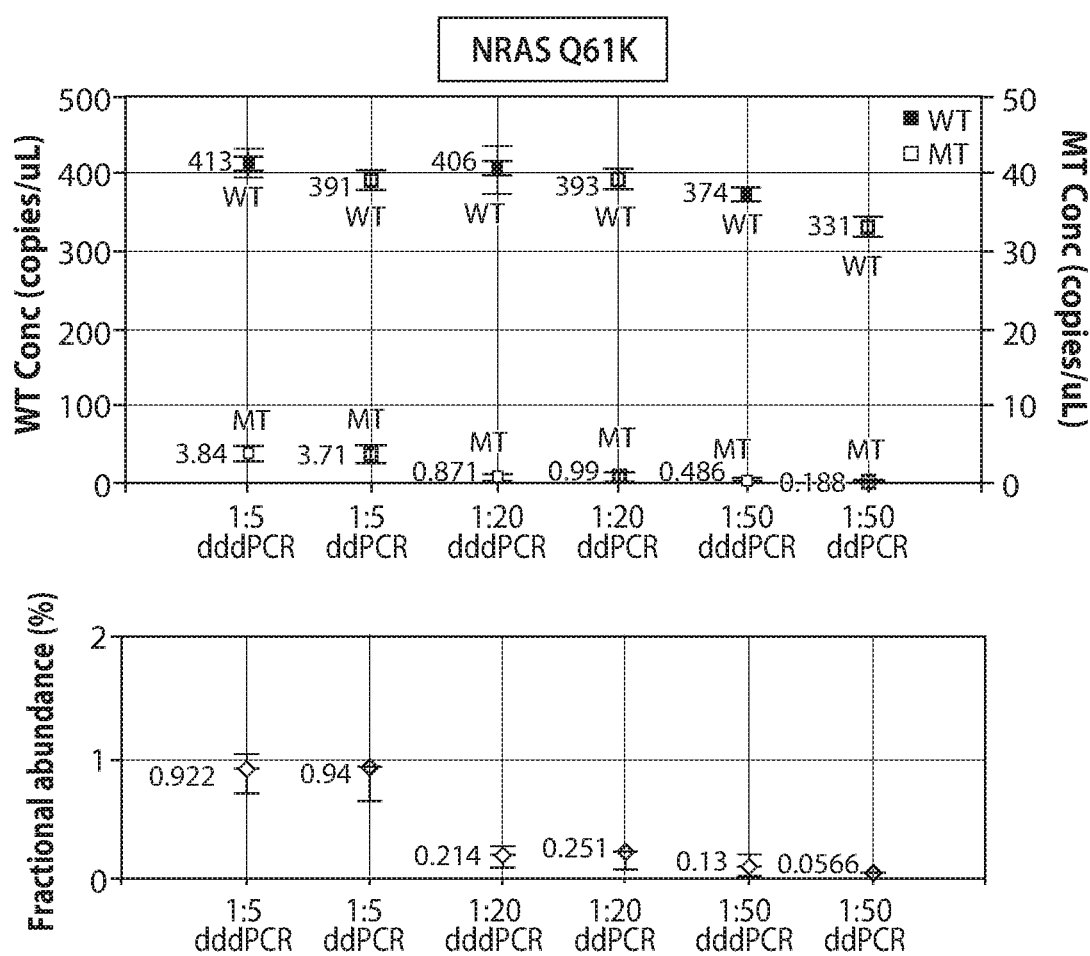
Figure 17A:
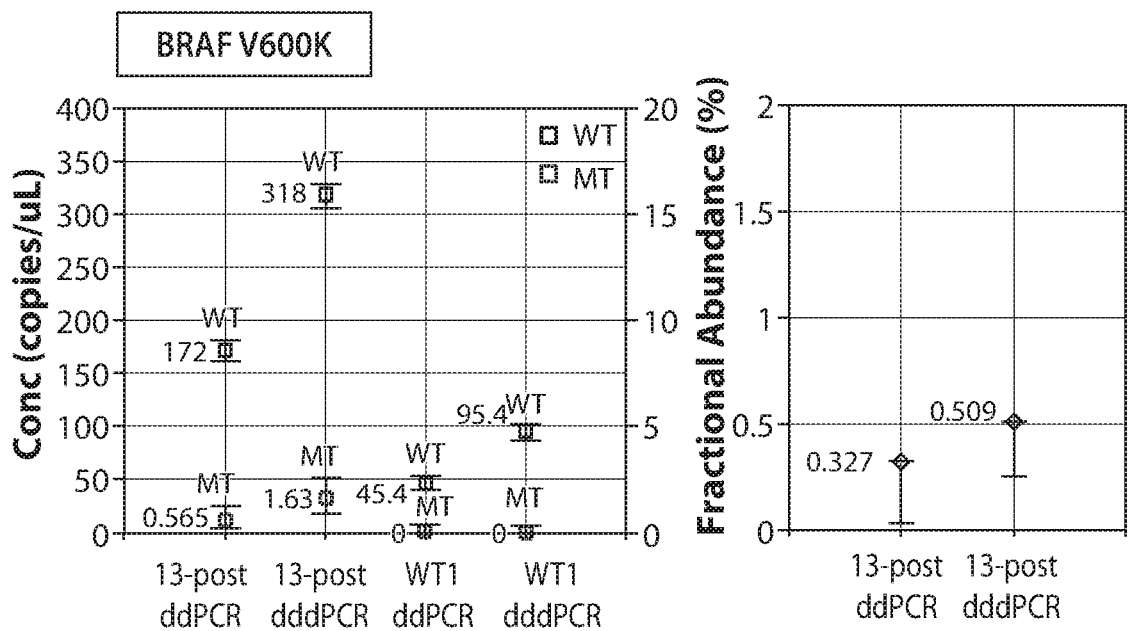
FIGS. 17A-17C show ddPCR and dddPCR applied to cfDNA samples from cancer patients. The sample 13-post was genotyped for BRAF V600K (FIG. 17A), sample 148-post for BRAF V600E (FIG. 17B), and samples C11, C8, scr for EGFR L858R (FIG. 17C). The BRAF V600K assay was performed with 15 ng of cfDNA input. The BRAF V600E assay was performed with 10 ng input. The EGFR L858R assay was performed with a fixed sample volume since the expected concentration of those samples was very low. The error bars represent the 95% confidence interval for the Poisson distribution.
Figure 17B:
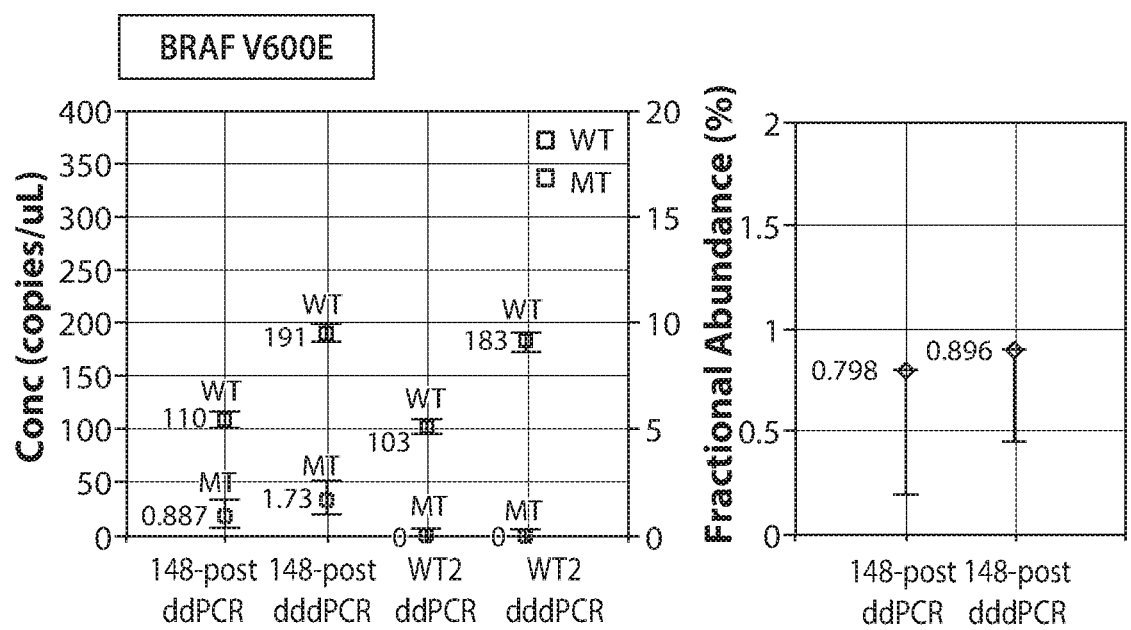
Figure 17C:
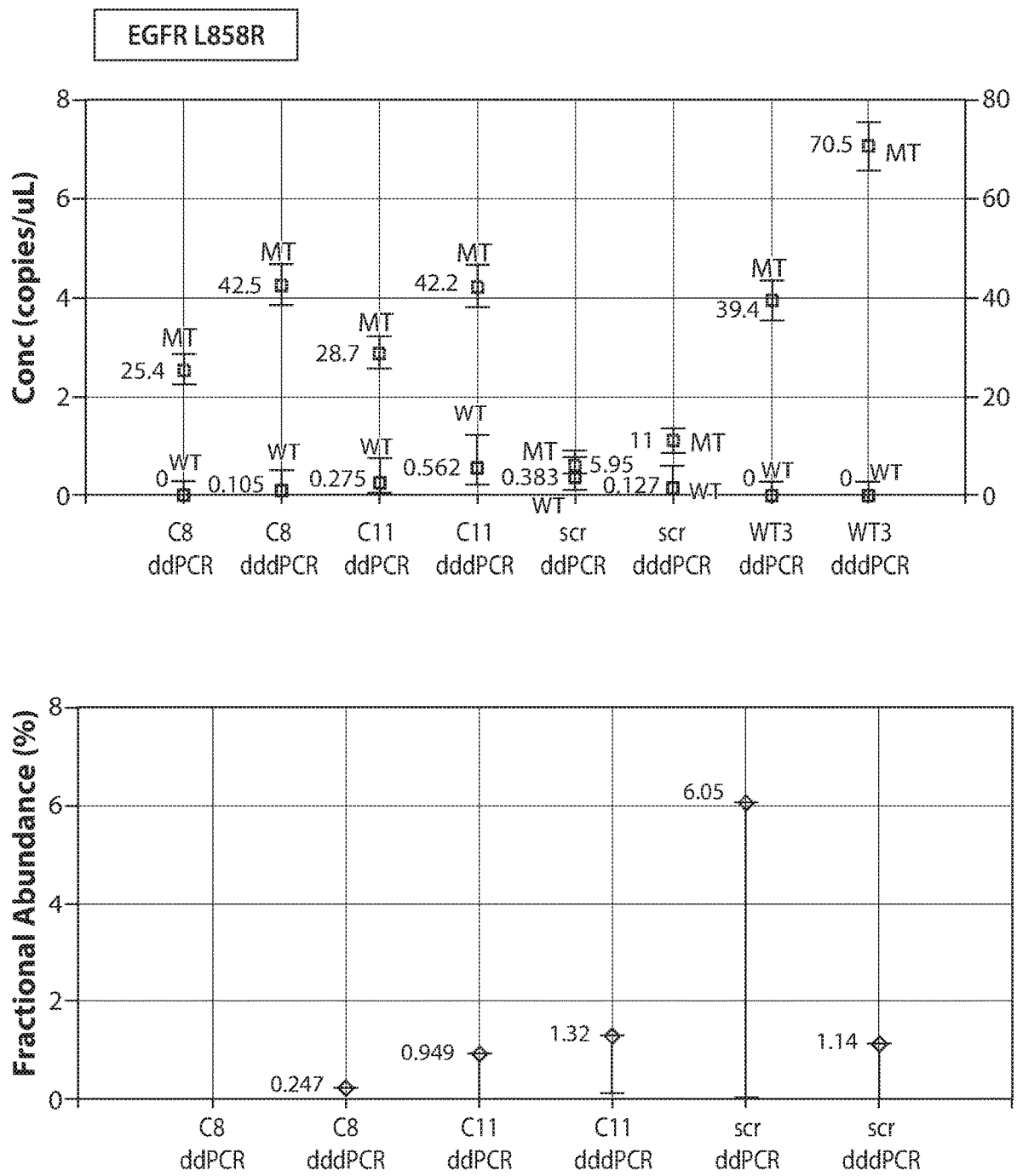

Since dddPCR can double the number of positive events for a gDNA sample when compared to ddPCR, it should be possible to split the original sample in two reactions; thereby analyzing two different targets independently, each target resulting in similar number of positive droplets as a ddPCR applied on the entire sample (FIG. 16A). To test this, HD728 gDNA reference mutation standard was used, which contains BRAF p.V600E (8% allelic frequency) and NRAS p.Q61K (5% allelic frequency). This sample was serially diluted to 1:5, 1:20 and 1:50-fold into WT gDNA. 15 ng DNA was used for dddPCR, and 30 ng DNA for standard ddPCR. The number of positive events and the concentration of WT and MT copies obtained were similar for both dddPCR and ddPCR (FIGS. 16B, 16C). Further, the resulting fractional mutation abundance was similar between protocols for all dilutions tested. While caution would be required when splitting samples that contain just 1-2 copies of mutated alleles, the data indicate that in general, samples can be interrogated for 2 mutations by dddPCR using the same quantity of DNA needed for analysis of only one mutation by standard ddPCR. Therefore, the number of potential assays is doubled by replacing ddPCR with dddPCR.

dddPCR Applied on cfDNA from Clinical Samples cfDNA samples from cancer patients previously screened for mutations were comparatively analyzed by dddPCR and ddPCR. Samples 13-post and 148-post represent plasma collected from two cancer patients post treatment, and harbor BRAF p.V600K and p.V600E, respectively. Samples SCR, C8 and C11 represent plasma collected at three different chemotherapy treatment cycles from a single patient, harbor EGFR p.L858R and have relatively low amount of cfDNA collected from plasma. WT cfDNA samples obtained from healthy donors were run in parallel as controls for all assays. The results are summarized in FIGS. 17A-17C and Table 2.

The data indicate that, for two out of five cfDNA samples tested, there is increased confidence in calling a mutation when dddPCR is applied instead of standard ddPCR. For example, the 95% confidence limits for sample 13-post do not overlap with the WT control limits, when analyzed via dddPCR (Table 2 and FIG. 17A). In contrast, there is overlap in confidence limits using standard ddPCR. Similar results are also shown for sample 148-post (Table 2 and FIG. 17B).

Across all cfDNA clinical samples tested, an increased number of positive droplets was obtained when applying dddPCR as opposed to ddPCR on cfDNA. However, the ratio of dddPCR/ddPCR copies/0 was in the range 1.5-1.8 rather than 1.9-2.0 observed for gDNA. In view of this, an additional step was developed to increase further the positive events obtained with dddPCR for cfDNA (see below).

TABLE 2

Measured concentration of mutant copies in cfDNA from clinical samples analyzed by dddPCR and ddPCR

| | | | MT concen- | Poisson error (95% confidence interval) | |
|---|---|---|---|---|---|
| Sample | Target | Method | tration (copies/uL) | Upper error bar | Lower error bar |
| 13-post | BRAF V600K | ddPCR | 0.565 | 1.23 | 0.199 |
| | | dddPCR | 1.63 | 2.57 | 0.951 |
| WT1 | BRAF V600K | ddPCR | 0 | 0.414 | 0 |
| | | dddPCR | 0 | 0.354 | 0 |
| 148-post | BRAF V600E | ddpCR | 0.887 | 1.73 | 0.377 |
| | | dddPCR | 1.73 | 2.72 | 1.01 |
| WT2 | BRAF V600E | ddPCR | 0 | 0.327 | 0 |
| | | dddPCR | 0 | 0.346 | 0 |
| C8 | EGFR L858R | ddPCR | 0 | 0.269 | 0 |
| | | dddPCR | 0.105 | 0.503 | 0.00443 |
| C11 | EGFR L858R | ddPCR | 0.275 | 0.728 | 0.0652 |
| | | dddPCR | 0.562 | 1.22 | 0.198 |
| Scr | EGFR L858R | ddPC8 | 0.383 | 0.903 | 0.116 |
| | | dddPCR | 0.127 | 0.606 | 0.00532 |
| WT3 | EGFR L858R | ddPCR | 0 | 0.292 | 0 |
| | | dddPCR | 0 | 0.265 | 0 | dddPCR applied to end-repaired cfDNA

Figure 18A:
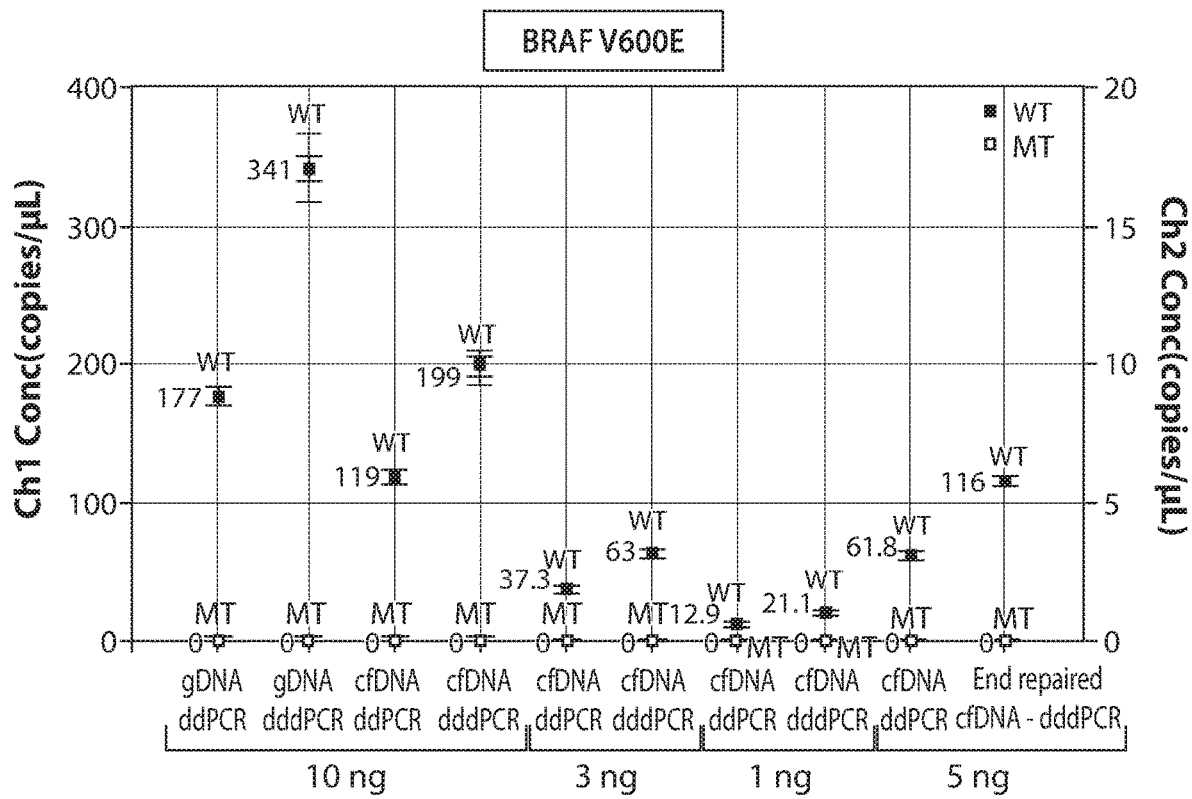
FIGS. 18A-18D shows dddPCR applied to randomly fragmented cfDNA and end-repaired cfDNA.

It was hypothesized that when randomly fragmented, small size DNA (e.g. cfDNA) is denatured and partitioned in droplets, some ssDNA copies can bind the PCR primers while others cannot due to their size. Consequently, dddPCR does not result in doubling of positive droplets when compared to ddPCR. To enable application of dddPCR on randomly fragmented cfDNA while retaining a ratio of 1.9-2, like that obtained with large-fragment genomic DNA or blunt ended DNA, an end-repair step was added prior to denaturation.

dddPCR using the current protocol was first applied multiple times on WT cfDNA obtained from normal volunteers to obtain a dddPCR/ddPCR ratio baseline for non-repaired cfDNA. BRAF p.V600E dddPCR assay was applied to 10, 3 and 1 ng WT cell-free DNA and the concentration of copy numbers was compared to standard ddPCR (FIG. 18A). The ratio dddPCR/ddPCR copies/µl was on average 1.65 irrespective of the initial input, lower than 1.9-2.0 observed for gDNA (FIG. 18B). ddPCR and dddPCR protocols were also applied for additional ddPCR assays, designed to interrogate mutations BRAF p.V600K, EGFR p.L858R, and EGFR polymorphism rs1050171, that employ amplicons 78-111 bp and similar results were obtained (data not shown). Overall, in the absence of end-repair the ratio of dddPCR to ddPCR for cfDNA is about 1.65 for amplicon sizes of 78-111 bp long that are used frequently.

Figure 19A:
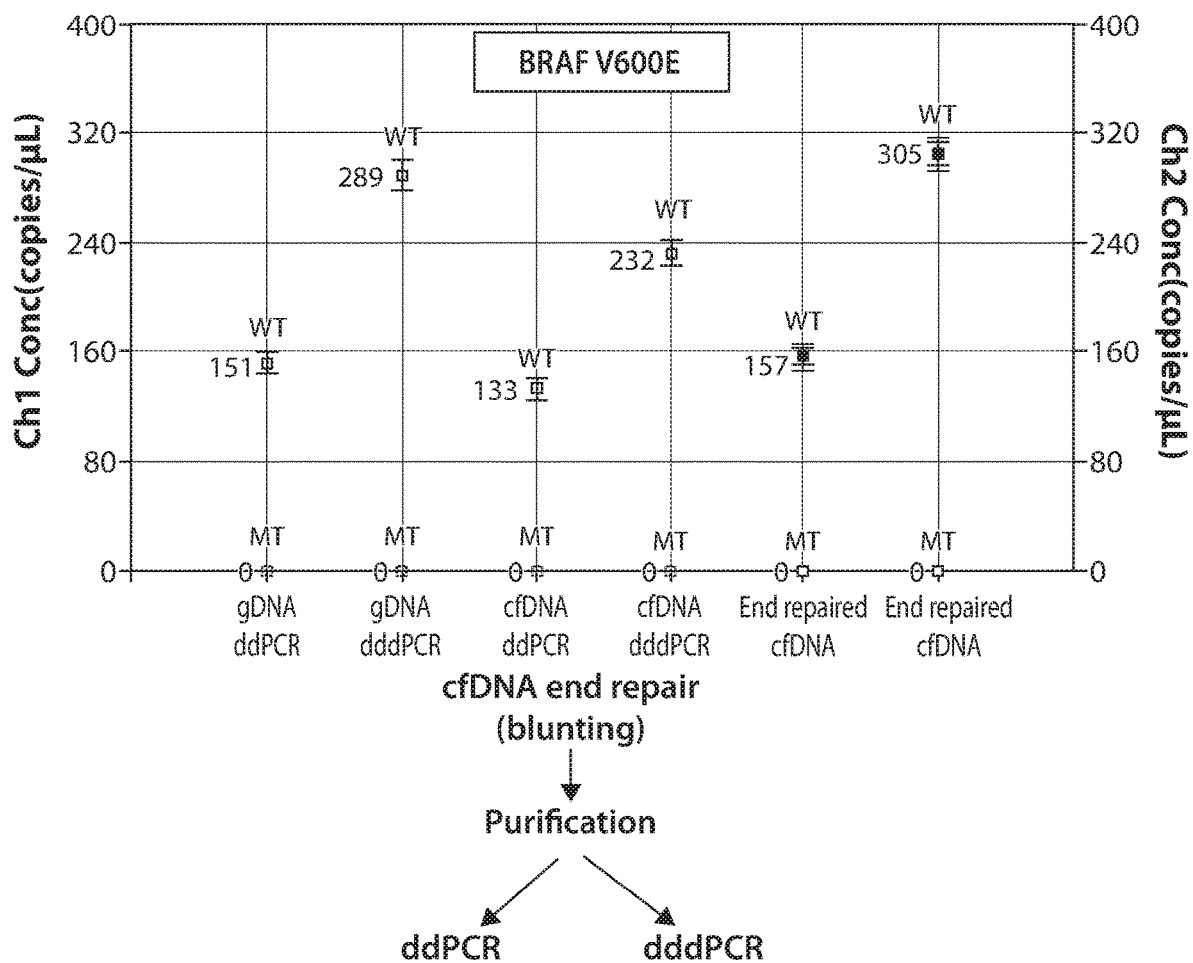
Figure 19B:
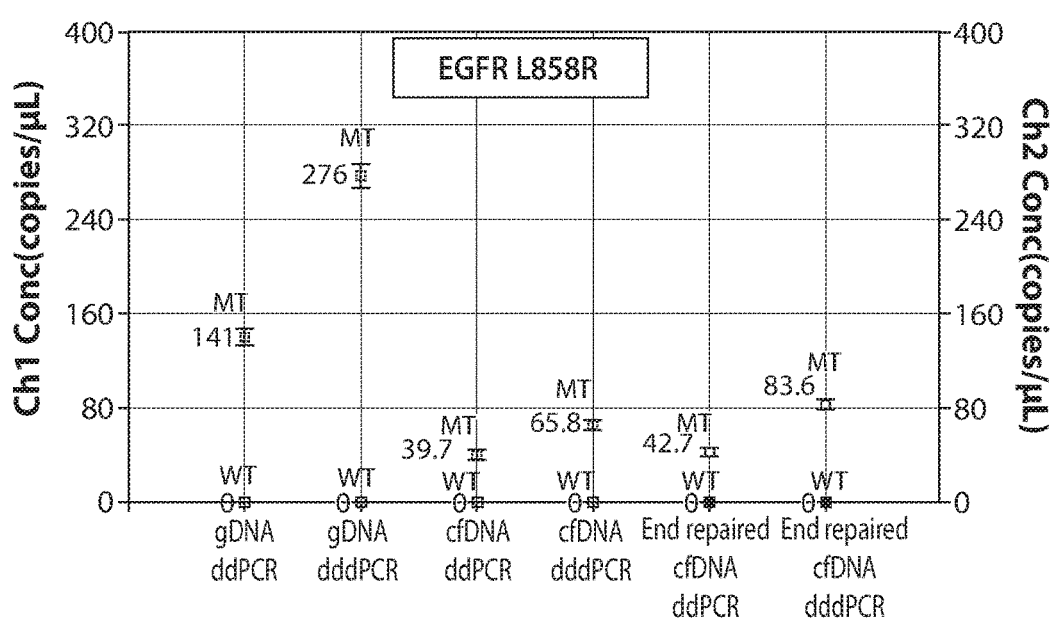

Next, end-repair was performed on WT cfDNA samples just prior to denaturation and droplet formation. Initially cfDNA was blunted with end-repair enzyme in the manufacturer supplied buffer. The blunted cfDNA was then purified and analyzed via ddPCR or dddPCR in parallel, using two different assays, BRAF p.V600E and EGFR p.L858R (FIGS. 19A, 19B). For both assays, the concentration fold-change for end-repaired cfDNA was higher than for not repaired cfDNA and similar to genomic DNA, ~1.9-2 (FIG. 19C).

Figure 18B:
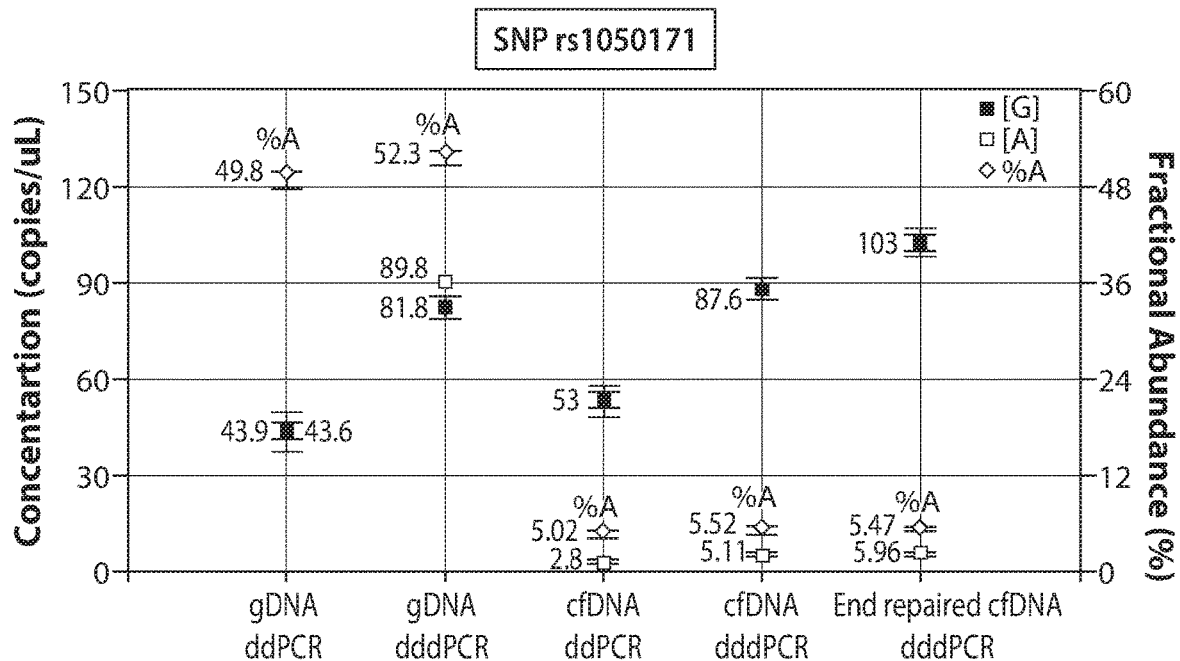
Figure 18C:
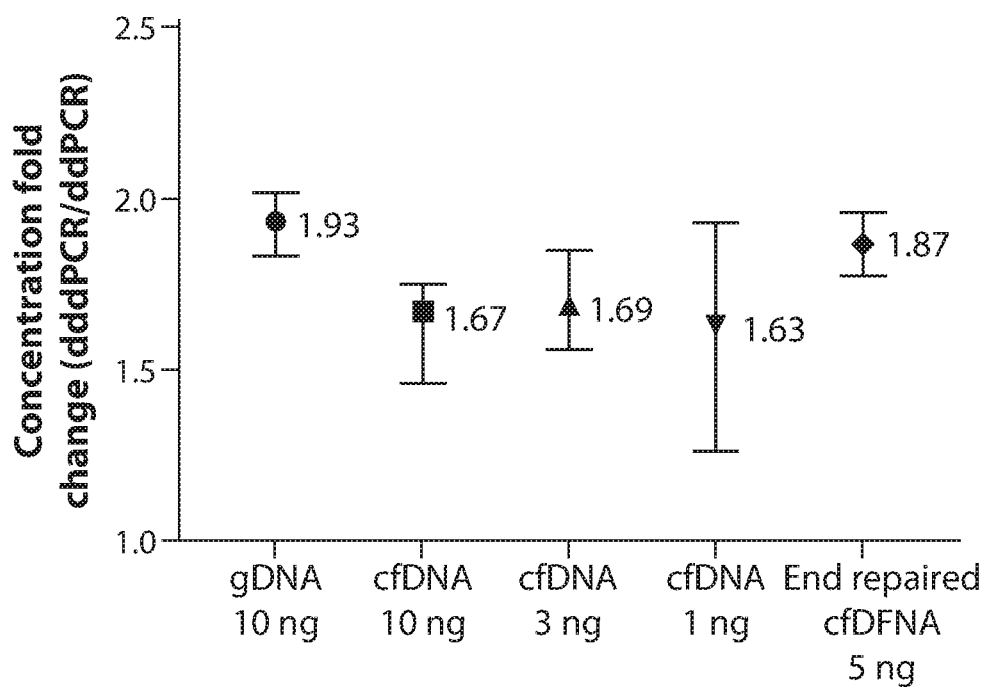
Figure 18D:
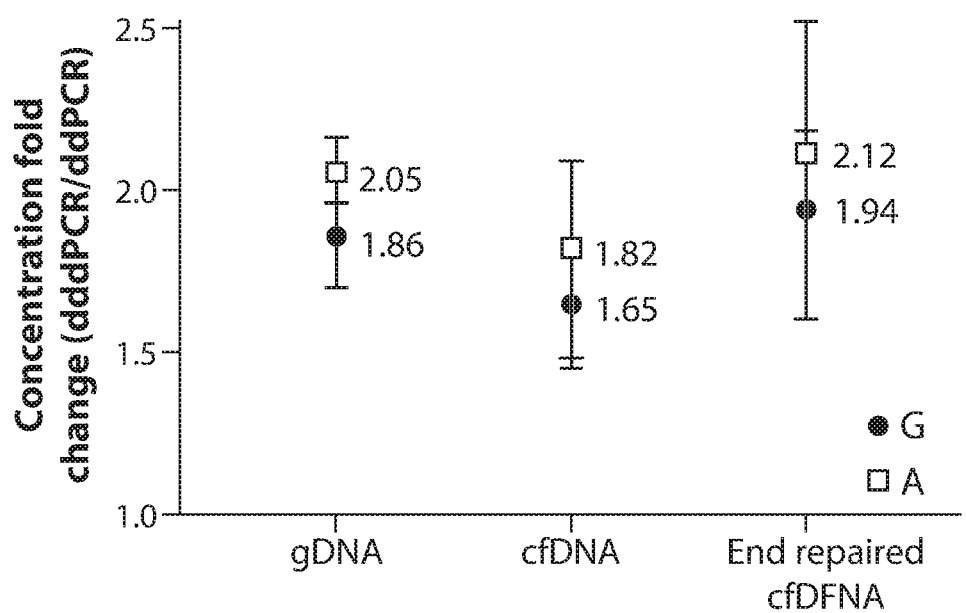

Subsequently a single-tube, homogeneous protocol for end-repair and dddPCR was developed (see Materials hereinabove), by adding the end-repair enzyme directly into the ddPCR buffer. The single-tube end-repair dddPCR protocol was applied to 5 ng cfDNA using two different assays, BRAF p.V600E and EGFR SNP rs1050171. The concentration fold-change was obtained by dividing the end-repair dddPCR values by standard ddPCR values (FIGS. 18A-18D). The BRAF assay was tested using WT cfDNA, resulting in increased fold change for blunted cfDNA of 1.9-2, like gDNA (FIGS. 18A, 18C). A SNP rs1050171 assay was then used to test the end-repair dddPCR protocol on cfDNA. A cfDNA sample with 5% minority allele was prepared and the concentration fold change was compared for repaired vs. non-repaired cfDNA. Genomic DNA (G1471), heterozygous for the same G/A polymorphism, was analyzed in parallel (FIGS. 18B, 18D). Similar fold-changes were observed for the 5% variant (allele A) and the 95% variant (allele G), for each condition. The data indicate that, by applying end-repair to cfDNA, the ratio of dddPCR to ddPCR is restored to 1.9-2.0, equal to that obtained for large fragments of genomic DNA or blunt DNA.

The limited amount of DNA obtained from liquid biopsies restricts the number of targets that can be examined via ddPCR or real time PCR and reduces the ability to identify rare mutations (23,33). It is possible to apply a DNA pre-amplification step prior to mutation detection and ddPCR to increase the material available (29,34). However, pre-amplification eliminates one of the main advantages of digital PCR, the absolute quantification of DNA copies, while the possibility for polymerase-introduced errors increases. Further, pre-amplification may introduce measurement bias and decrease the precision of digital PCR (29) and entails an extra step that increases cost, complexity and the risk for cross-contamination.

Applying complete denaturation just before droplet formation, as proposed in this work, entails minimal change to the established protocols and doubles the number of positive droplets without reducing the advantages of digital PCR. For cfDNA an additional end-repair step is applied to equalize sense and anti-sense strands and retain the approximate doubling of positive events following denaturation. This single-tube process entails direct addition of repair enzymes into the ddPCR mastermix. While end-repair performed in the same tube is a minor change to the overall protocol, it is also possible to simply omit repair and apply a 1.6-1.7-fold increase in the number of positive droplets, as opposed to 1.9-2-fold obtained after repair, for cfDNA and amplicons between 70-110 bp long. Thus, for absolute quantification purposes a correction of 1.65-fold in the measured copy number concentration could be applied without cfDNA repair while a 1.95-fold can be applied with repair or whenever PCR amplicons are substantially smaller than the interrogated DNA fragments.

Partial denaturation prior to droplet formation was considered to be a potential problem in ddPCR, as it might affect quantification (25), while DNA damage in long templates may reduce the obtained number of positive events (32,35). As FIGS. 9A-9B, 12A-12B, 16A-16C, and 18A-18D demonstrate these concerns are overcome using the current cycling protocol that enables complete denaturation and short (<110 bp) amplicons, while restricting excessive heating at 95° C.

While droplet-based digital PCR is focused on herein, the same approach is applicable to other digital PCR platforms. Further, while emphasis in this work is on mutations, doubling the number of positive droplets in digital PCR may be equally beneficial for copy number and gene amplification analysis via digital PCR (36), as increasing the number of events decreases the overall measurement uncertainty. In addition to applications in cancer, dddPCR application in prenatal diagnosis, in organ transplantation, and others can also be envisioned.

In summary, a process was developed for doubling the number of positive events during digital droplet PCR by partitioning denatured, single DNA strands in droplets, and by applying end-repair prior to denaturation for the specific case of randomly fragmented DNA (cfDNA). This simple modification doubles the potential number of assays from a given amount of input DNA and improves the confidence limits in digital PCR-based mutation detection. The process entails minor departure from established digital-PCR protocols and enables extraction of more information from precious clinical samples and liquid biopsies.

REFERENCES

1. Tyagi, S. and Kramer, F. R. (1996) Molecular beacons: probes that fluoresce upon hybridization. Nat Biotechnol, 14, 303-308.
2. Bernard, P. S. and Wittwer, C. T. (2002) Real-time PCR technology for cancer diagnostics. Clin Chem, 48, 1178-1185.
3. Li, J., Wang, F., Mamon, H., Kulke, M. H., Harris, L., Maher, E., Wang, L. and Makrigiorgos, G. M. (2006) Antiprimer quenching-based real-time PCR and its application to the analysis of clinical cancer samples. Clinical Chemistry, 52, 624-633.
4. Amicarelli, G., Shehi, E., Makrigiorgos, G. M. and Adlerstein, D. (2007) FLAG assay as a novel method for real-time signal generation during PCR: application to detection and genotyping of KRAS codon 12 mutations. Nucleic acids research, 35, e131.
5. Li, J., Wang, L., Janne, P. A. and Makrigiorgos, G. M. (2009) Coamplification at lower denaturation temperature-PCR increases mutation-detection selectivity of TaqMan-based real-time PCR. Clin Chem, 55, 748-756.
6. Sanchez, J. A., Pierce, K. E., Rice, J. E. and Wangh, L. J. (2004) Linear-after-the-exponential (LATE)-PCR: an advanced method of asymmetric PCR and its uses in quantitative real-time analysis. Proceedings of the National Academy of Sciences of the United States of America, 101, 1933-1938.
7. Li, J., Wang, L., Mamon, H., Kulke, M. H., Berbeco, R. and Makrigiorgos, G. M. (2008) Replacing PCR with COLD-PCR enriches variant DNA sequences and redefines the sensitivity of genetic testing. Nat Med, 14, 579-584.
8. Milbury, C. A., Li, J. and Makrigiorgos, G. M. (2011) Ice-COLD-PCR enables rapid amplification and robust enrichment for low-abundance unknown DNA mutations. Nucleic acids research, 39, e2.
9. How Kit, A., Mazaleyrat, N., Daunay, A., Nielsen, H. M., Terris, B. and Tost, J. (2013) Sensitive detection of KRAS mutations using enhanced-ice-COLD-PCR mutation enrichment and direct sequence identification. Hum Mutat, 34, 1568-1580.
10. Liu, Y., Song, C., Ladas, I., Fitarelli-Kiehl, M. and Makrigiorgos, G. M. (2017) Methylation-sensitive enrichment of minor DNA alleles using a double-strand DNA-specific nuclease. Nucleic acids research, 45, e39.
11. Hindson, C. M., Chevillet, J. R., Briggs, H. A., Gallichotte, E. N., Ruf, I. K., Hindson, B. J., Vessella, R. L. and Tewari, M. (2013) Absolute quantification by droplet digital PCR versus analog real-time PCR. Nat Methods, 10, 1003-1005.
12. Song, C., Liu, Y., Fontana, R., Makrigiorgos, A., Mamon, H., Kulke, M. H. and Makrigiorgos, G. M. (2016) Elimination of unaltered DNA in mixed clinical samples via nuclease-assisted minor-allele enrichment. Nucleic acids research, 44, e146.
13. Ladas, I., Yu, F., Leong, K. W., Fitarelli-Kiehl, M., Song, C., Ashtaputre, R., Kulke, M., Mamon, H. and Makrigiorgos, G. M. (2018) Enhanced detection of microsatellite instability using pre-PCR elimination of wild-type DNA homo-polymers in tissue and liquid biopsies. Nucleic acids research.
14. Wu, L. R., Chen, S. X., Wu, Y., Patel, A. A. and Zhang, D. Y. (2017) Multiplexed enrichment of rare DNA variants via sequence-selective and temperature-robust amplification. Nat Biomed Eng, 1, 714-723.
15. Adalsteinsson, V. A., Ha, G., Freeman, S. S., Choudhury, A. D., Stover, D. G., Parsons, H. A., Gydush, G., Reed, S. C., Rotem, D., Rhoades, J., Loginov, D., Livitz, D., Rosebrock, D., Leshchiner, I., Kim, J., Stewart, C., Rosenberg, M., Francis, J. M., Zhang, C. Z., Cohen, O., Oh, C., Ding, H., Polak, P., Lloyd, M., Mahmud, S., Helvie, K., Merrill, M. S., Santiago, R. A., O'Connor, E. P., Jeong, S. H., Leeson, R., Barry, R. M., Kramkowski, J. F., Zhang, Z., Polacek, L., Lohr, J. G., Schleicher, M., Lipscomb, E., Saltzman, A., Oliver, N. M., Marini, L., Waks, A. G., Harshman, L. C., Tolaney, S. M., Van Allen, E. M., Winer, E. P., Lin, N. U., Nakabayashi, M., Taplin, M. E., Johannessen, C. M., Garraway, L. A., Golub, T. R., Boehm, J. S., Wagle, N., Getz, G., Love, J. C. and Meyerson, M. (2017) Scalable whole-exome sequencing of cell-free DNA reveals high concordance with metastatic tumors. Nat Commun, 8, 1324.
16. Thomas, R. K., Nickerson, E., Simons, J. F., Janne, P. A., Tengs, T., Yuza, Y., Garraway, L. A., Laframboise, T., Lee, J. C., Shah, K., O'Neill, K., Sasaki, H., Lindeman, N., Wong, K. K., Borras, A. M., Gutmann, E. J., Dragnev, K. H., Debiasi, R., Chen, T. H., Glatt, K. A., Greulich, H., Desany, B., Lubeski, C. K., Brockman, W., Alvarez, P., Hutchison, S. K., Leamon, J. H., Ronan, M. T., Turenchalk, G. S., Egholm, M., Sellers, W. R., Rothberg, J. M. and Meyerson, M. (2006) Sensitive mutation detection in heterogeneous cancer specimens by massively parallel picoliter reactor sequencing. Nat Med, 12, 852-855.
17. Milbury, C. A., Correll, M., Quackenbush, J., Rubio, R. and Makrigiorgos, G. M. (2012) COLD-PCR enrichment of rare cancer mutations prior to targeted amplicon resequencing. Clin Chem, 58, 580-589.
18. Narayan, A., Carriero, N. J., Gettinger, S. N., Kluytenaar, J., Kozak, K. R., Yock, T. I., Muscato, N. E., Ugarelli, P., Decker, R. H. and Patel, A. A. (2012) Ultrasensitive measurement of hotspot mutations in tumor DNA in blood using error-suppressed multiplexed deep sequencing. Cancer Res, 72, 3492-3498.
19. Vogelstein, B. and Kinzler, K. W. (1999) Digital PCR. Proceedings of the National Academy of Sciences of the United States of America, 96, 9236-9241.
20. Taly, V., Pekin, D., Benhaim, L., Kotsopoulos, S. K., Le Corre, D., Li, X., Atochin, I., Link, D. R., Griffiths, A. D., Pallier, K., Blons, H., Bouche, O., Landi, B., Hutchison, J. B. and Laurent-Puig, P. (2013) Multiplex picodroplet digital PCR to detect KRAS mutations in circulating DNA from the plasma of colorectal cancer patients. Clin Chem, 59, 1722-1731.
21. Day, E., Dear, P. H. and McCaughan, F. (2013) Digital PCR strategies in the development and analysis of molecular biomarkers for personalized medicine. Methods, 59, 101-107.
22. Castellanos-Rizaldos, E., Paweletz, C., Song, C., Oxnard, G. R., Mamon, H., Janne, P. A. and Makrigiorgos, G. M. (2015) Enhanced ratio of signals enables digital mutation scanning for rare allele detection. The Journal of molecular diagnostics: JMD, 17, 284-292.
23. Huggett, J. F., Cowen, S. and Foy, C. A. (2015) Considerations for digital PCR as an accurate molecular diagnostic tool. Clin Chem, 61, 79-88.
24. Laurent-Puig, P., Pekin, D., Normand, C., Kotsopoulos, S. K., Nizard, P., Perez-Toralla, K., Rowell, R., Olson, J., Srinivasan, P., Le Corre, D., Hor, T., El Harrak, Z., Li, X., Link, D. R., Bouche, O., Emile, J. F., Landi, B., Boige, V., Hutchison, J. B. and Taly, V. (2015) Clinical relevance of KRAS-mutated subclones detected with picodroplet digital PCR in advanced colorectal cancer treated with anti-EGFR therapy. Clin Cancer Res, 21, 1087-1097.
25. Huggett, J. F., Foy, C. A., Benes, V., Emslie, K., Garson, J. A., Haynes, R., Hellemans, J., Kubista, M., Mueller, R. D., Nolan, T., Pfaffl, M. W., Shipley, G. L., Vandesompele, J., Wittwer, C. T. and Bustin, S. A. (2013) The digital MIQE guidelines: Minimum Information for Publication of Quantitative Digital PCR Experiments. Clin Chem, 59, 892-902.
26. Oxnard, G. R., Paweletz, C. P., Kuang, Y., Mach, S. L., O'Connell, A., Messineo, M. M., Luke, J. J., Butaney, M., Kirschmeier, P., Jackman, D. M. and Janne, P. A. (2014) Noninvasive Detection of Response and Resistance in EGFR-Mutant Lung Cancer Using Quantitative Next-Generation Genotyping of Cell-Free Plasma DNA. Clin Cancer Res.
27. Diehl, F., Schmidt, K., Choti, M. A., Romans, K., Goodman, S., Li, M., Thornton, K., Agrawal, N., Sokoll, L., Szabo, S. A., Kinzler, K. W., Vogelstein, B. and Diaz, L. A., Jr. (2008) Circulating mutant DNA to assess tumor dynamics. Nat Med, 14, 985-990.

28. Postel, M., Roosen, A., Laurent-Puig, P., Taly, V. and Wang-Renault, S. F. (2018) Droplet-based digital PCR and next generation sequencing for monitoring circulating tumor DNA: a cancer diagnostic perspective. Expert Rev Mol Diagn, 18, 7-17.
29. Whale, A. S., Cowen, S., Foy, C. A. and Huggett, J. F. (2013) Methods for applying accurate digital PCR analysis on low copy DNA samples. PLoS One, 8, e58177.
30. Hindson, B. J., Ness, K. D., Masquelier, D. A., Belgrader, P., Heredia, N. J., Makarewicz, A. J., Bright, I. J., Lucero, M. Y., Hiddessen, A. L., Legler, T. C., Kitano, T. K., Hodel, M. R., Petersen, J. F., Wyatt, P. W., Steenblock, E. R., Shah, P. H., Bousse, L. J., Troup, C. B., Mellen, J. C., Wittmann, D. K., Erndt, N. G., Cauley, T. H., Koehler, R. T., So, A. P., Dube, S., Rose, K. A., Montesclaros, L., Wang, S., Stumbo, D. P., Hodges, S. P., Romine, S., Milanovich, F. P., White, H. E., Regan, J. F., Karlin-Neumann, G. A., Hindson, C. M., Saxonov, S. and Colston, B. W. (2011) High-throughput droplet digital PCR system for absolute quantitation of DNA copy number. Anal Chem, 83, 8604-8610.
31. Herrmann, M. G., Durtschi, J. D., Bromley, L. K., Wittwer, C. T. and Voelkerding, K. V. (2006) Amplicon DNA melting analysis for mutation scanning and genotyping: cross-platform comparison of instruments and dyes. Clin Chem, 52, 494-503.
32. Bhat, S., McLaughlin, J. L. and Emslie, K. R. (2011) Effect of sustained elevated temperature prior to amplification on template copy number estimation using digital polymerase chain reaction. Analyst, 136, 724-732.
33. Milbury, C. A., Li, J. and Makrigiorgos, G. M. (2009) PCR-Based Methods for the Enrichment of Minority Alleles and Mutations. Clin Chem.
34. Murphy, D. M., Bejar, R., Stevenson, K., Neuberg, D., Shi, Y., Cubrich, C., Richardson, K., Eastlake, P., Garcia-Manero, G., Kantarjian, H., Ebert, B. L. and Mike Makrigiorgos, G. (2013) NRAS mutations with low allele burden have independent prognostic significance for patients with lower risk myelodysplastic syndromes. Leukemia, 27, 2077-2081.
35. Bhat, S., Curach, N., Mostyn, T., Bains, G. S., Griffiths, K. R. and Emslie, K. R. (2010) Comparison of methods for accurate quantification of DNA mass concentration with traceability to the international system of units. Anal Chem, 82, 7185-7192.
36. Gevensleben, H., Garcia-Murillas, I., Graeser, M. K., Schiavon, G., Osin, P., Parton, M., Smith, I. E., Ashworth, A. and Turner, N. C. (2013) Noninvasive detection of HER2 amplification with plasma DNA digital PCR. Clin Cancer Res, 19, 3276-3284.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

What is claimed is:

1. A method for increasing the number of compartments in which a target sequence is identified by an assay, comprising:
   (a) obtaining a sample comprising double-stranded DNA comprising a target sequence, wherein the sample comprises double-stranded DNA comprising complementary strands of unequal length;
   (b) producing blunt ends on the double-stranded DNA;
   (c) denaturing the double-stranded DNA in a sample to form single-stranded DNA;
   (d) partitioning the sample of formed single-stranded DNA into a multitude of compartments, wherein a majority of the compartments contain either one or no single-stranded DNAs comprising the target sequence; and
   (e) assaying to identify compartments containing target sequences;
   wherein the producing blunt ends of step (b) and denaturing of step (c) increases the number of compartments in which the target sequence is identified by the assaying of step (e) compared to a method that does not comprise the producing blunt ends of step (b) and denaturing of step (c).

2. The method of claim 1, wherein the assaying comprises applying isothermal amplification conditions or polymerase chain reaction (PCR) conditions in each of the compartments.

3. The method of claim 2, wherein the assaying comprises applying isothermal amplification conditions, further comprising adding one or more of the following isothermal amplification reagents to the sample: a DNA-nicking nuclease, a strand-displacing polymerase, and deoxynucleotide triphosphates (dNTPs).

4. The method of claim 2, wherein the assaying comprises applying PCR conditions, further comprising adding one or more of the following PCR reagents to the sample: forward and reverse primers, a polymerase, hydrolysis probes, and deoxynucleotide triphosphates (dNTPs).

5. The method of claim 4, wherein the one or more PCR reagents are added to the sample prior to denaturing the double-stranded DNA.

6. The method of claim 1, wherein the denaturing of the double-stranded DNA is performed by exposing the sample to a temperature of at least 95° C.

7. The method of claim 1, wherein the compartments are micro well plates, capillaries, oil-in-water emulsion droplets, nano-fluidic devices, or arrays of miniaturized chambers.

8. The method of claim 2, wherein prior to performing PCR, double stranded DNA comprising the target sequence is generated from the single stranded target sequence in each compartment, and the PCR comprises:
   (a) activating a polymerase;
   (b) denaturing the generated double stranded target DNA to generate a plurality of single stranded sequences;
   (c) annealing of primers to the generated plurality of single-stranded DNA comprising a target;
   (d) extending the primers to form double-strand DNA; and
   (e) repeating steps (b)-(d) at least once.

9. The method of claim 8, wherein the polymerase is activated by exposing the compartment to a temperature of 90-97° C. for 0.1-10 minutes, denaturing the DNA comprises exposing the compartment to a temperature of 90-98° C. for 2-120 seconds, and annealing of primers to single-stranded DNA and extending the primers to form double-stranded DNA comprises exposing the compartment to a temperature of 50-70° C. for 5 seconds to 2 minutes.

10. The method of claim 1, further comprising reducing the damage of single-stranded DNA prior to assaying for the target in each of the compartments, wherein reducing damage of formed single-stranded DNA comprises:

partially activating polymerase by exposing each compartment to a temperature of 90-97° C. for between 0.1-2 (inclusive) minutes; and generating double-stranded DNA by performing 2-8 cycles of PCR.

11. The method of claim 1, wherein the double-stranded DNA in the sample is genomic DNA or cDNA.

12. The method of claim 11, wherein the genomic DNA is cell-free circulating DNA.

13. The method of claim 11, wherein the genomic DNA is obtained from a biological sample.

14. The method of claim 2, wherein the size of amplicons formed during PCR in each of the compartments is 50-120 bp.

15. The method of claim 1, further comprising determining the quantity of single-stranded target sequences in the sample by determining the number of compartments that contain a target sequence and applying a mathematical correlation.

16. The method of claim 15, further comprising determining the quantity of double-stranded target sequences in the sample by dividing the quantity of single-stranded target sequences by two.

17. The method of claim 1, wherein the sample of formed single-stranded DNA is divided into two or more reactions to measure two or more target sequences.

18. The method of claim 1, wherein denaturing the double-stranded DNA to form single-stranded DNA prior to partitioning the sample into a multitude of compartments results in a 1.9-2 fold increase in the number of compartments in which a target is identified compared to the number of compartments in which a target is identified when assaying is performed on the same amount of double-stranded DNA under the same conditions but without denaturing the double-stranded DNA to form single-stranded DNA prior to partitioning the sample into a multitude of compartments.

19. The method of claim 1, wherein the assaying for the target comprises applying PCR, and wherein denaturing the double-stranded DNA to form single-stranded DNA prior to partitioning the sample into a multitude of compartments results in a 1.6-1.7 fold increase in the number of compartments in which a target is identified compared to the number of compartments in which a target is identified when PCR is performed on the same amount of double-stranded DNA under the same conditions but without denaturing the double-stranded DNA prior to partitioning the sample into a multitude of compartments.

20. The method of claim 1, wherein producing the blunt ends comprises treatment with an end-repair enzyme.

21. The method of claim 1, further comprising purifying the end-repaired double-stranded DNA prior to denaturing the double-stranded DNA.

* * * * *